US006872700B1

(12) United States Patent
Young et al.

(10) Patent No.: US 6,872,700 B1
(45) Date of Patent: Mar. 29, 2005

(54) METHODS FOR GLUCAGON SUPPRESSION

(75) Inventors: Andrew A. Young, La Jolla, CA (US); Bronislava Gedulin, San Diego, CA (US)

(73) Assignee: Amylin Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/889,331

(22) PCT Filed: Jan. 14, 2000

(86) PCT No.: PCT/US00/00942

§ 371 (c)(1),
(2), (4) Date: Dec. 18, 2001

(87) PCT Pub. No.: WO00/41548

PCT Pub. Date: Jul. 20, 2000

Related U.S. Application Data

(60) Provisional application No. 60/116,380, filed on Jan. 14, 1999, provisional application No. 60/132,017, filed on Apr. 30, 1999, and provisional application No. 60/175,365, filed on Jan. 10, 2000.

(51) Int. Cl.$^7$ .......................... A61K 38/02; A61K 38/26
(52) U.S. Cl. .......................... 514/2; 530/308; 530/322; 530/33; 530/402; 530/421; 424/278.1
(58) Field of Search ............................. 514/2; 530/308, 530/322, 33, 402, 421, 333, 344; 424/278.1

(56) References Cited

U.S. PATENT DOCUMENTS

| 4,179,337 A | * | 12/1979 | Davis et al. ................. 435/181 |
| 5,264,372 A | | 11/1993 | Beaumont et al. |
| 5,424,286 A | * | 6/1995 | Eng .............................. 514/2 |
| 5,686,511 A | | 11/1997 | Bobo |
| 6,051,557 A | * | 4/2000 | Drucker ......................... 514/2 |
| 6,268,343 B1 | * | 7/2001 | Knudsen et al. ............. 514/12 |
| 6,376,549 B1 | * | 4/2002 | Fine et al. ................... 514/635 |

FOREIGN PATENT DOCUMENTS

| AU | 723694 B2 | | 1/1998 |
| AU | 199731732 | | 1/1998 |
| WO | WO 95/07098 | | 3/1995 |
| WO | WO 97/46584 A1 | | 12/1997 |
| WO | WO 98/05351 | | 2/1998 |
| WO | WO 98/30231 | | 7/1998 |
| WO | WO9830231 | * | 7/1998 |
| WO | WO 99/07404 | | 2/1999 |
| WO | WO 99/25727 | | 5/1999 |
| WO | WO 99/25728 | | 5/1999 |
| WO | WO 99/40788 | | 8/1999 |
| WO | WO 00/41546 | | 7/2000 |
| WO | WO 00/41548 | | 7/2000 |

OTHER PUBLICATIONS

Bloom, S. R. et al. (1987) "Glucagonoma syndrome" Am. J. Med. vol. 82, pp. 25–36.*
Parhes, D. G. et al. (2001) "Insulinotropic actions of exendin–4 and glucagon–like peptide–1 in vivo and in vitro" Metabolis, vol. 50, p. 583–589.*
Drucker, D. J. (1998) "Glucagon–like peptides" Diabetes, vol. 47, pp. 159–169.*
Bloom, S. R. (1987) Glucagonoma syndrome. Am. J. Med. vol. 82(5B), pp. 25–36. Review.*
Carlsson, A. et al. (2000) Insulin and glucagon secretion in patients with slowly progressing autoimmune diabetes (LADA).☐☐J. Clin. Endocrinol. Metab. vol. 85, pp. 76–80.*
Marketletter, Aug. 24, 1998 (p. N/A).*
4, an Exendin–3 Analogue, from *Heloderma suspectum* Venom, *J. Biol. Chem.*, 267(11):7402–05 (1992).
Francis, et al., "PEGylation of Cytokines and Other Therapeutic Proteins and Peptides: the Importance of Biological Optimisation of Coupling Techniques," *International Journal of Hematology*, 68(1):1–18 (1998).
Goke, et al. "Exendin–4 Is a High Potency Agonist and Truncated Exendin–(9–39)–amide an Antagonist at the Glucagon–like Peptide 1–(7–36)–amide Receptor of Insulin–secreting β–Cells," *J. Biol. Chem.*, 268(26):19650–55 (1993).
Raufman, et al. "Truncated Glucagon–like Peptide–1 Interacts with Exendin Receptors in Dispersed Acini from Guinea Pig Pancreas," *J. Biol. Chem.*, 267(30):21432–37 (1992).
Chen, Y.E., et al., "Tissue–specific Expression of Unique mRNAs That Encode Proglucagon–derived Peptides or Exendin 4 in the Lizard," *Journal of Biological Chemistry*, 272(7): 4108–4115 (1997).
Creutzfeldt, W.O.C., et al., "Glucagonostatic Actions and Reduction of Fasting Hyperglycemia by Exogenous Glucagon–like Peptide I(7–36) Amide in Type I Diabetic Patients," *Diabetes Care* 19(6):580–6 (1996).
D'Alessio, et al., "Elimination of the Action of Glucagon–like Peptide 1 Causes an Impairment of Glucose Tolerance after Nutrient Ingestion by Healthy Baboons," *J. Clin. Invest.*, 97:133–38 (1996).
Eng, J., et al., "Purification and Structure of Exendin–3, a New Pancreatic Secretagogue Isolated from *Heloderma horridum* Venom," *J. Biol. Chem.*, 265(33):20259–62 (1990).

(Continued)

Primary Examiner—Karen Cochrane Carlson
Assistant Examiner—Samuel Wei Liu
(74) Attorney, Agent, or Firm—Arnold & Porter LLP

(57) ABSTRACT

Methods for use of an exendin, an exendin agonist, or a modified exendin or exendin agonist having an exendin or exendin agonist linked to one or more polyethylene glycol polymers, for example, for lowering glucagon levels and/or suppressing glucagon secretion in a subject are provide. These methods are useful in treating hyperglucagonemia and other conditions that would be benefited by lowering plasma glucagon or suppressing glucagon secretion.

24 Claims, 26 Drawing Sheets

OTHER PUBLICATIONS

Thorens, "Expression Cloning of the Pancreatic β Cell Receptor for the Gluco–Incretin Hormone Glucagon–like Peptide 1," *Proc. Natl. Acad. Sci. USA,* 89:8641–45 (1992).

Byrne, M.M., et al., "Lessons from Human Studies with Glucagon–like Peptide–1: Potential of the Gut Hormone for Clinical Use," *Front. Diabetes,* 13:219–33 (1997).

Egan, J.M., et al., "Glucagon–like Peptide–1 Restores Acute Phase Insulin Release to Aged Rats," *Diabetologia,* 40(Supp 1):A130 abstract 505 (1997).

Daniel, O. et al., "Use of Glucagon in the Treatment of Acute Diverticultis," *British Medical Journal,* 3:720–2, (1974).

Eissele, et al., "Rat Gastric Somatostation and Gastrin Release: Interactions of Exendin–4 and Truncated Glucagon–like Peptide–1 (GLP–1) Amide," *Life Sci.,* 55(8):629–34 (1994).

Eng, J., "Prolonged Effect of Exendin–4 on Hyperglycemia of db/db mice," *Diabetes,* 45(Supp 2):152A (abstract 554) (1996).

Glauser, et al., "Intravenous Glucagon in the Management of Esophageal Food Obstruction," JACEP, 8:228–231 (1979).

Malhotra, et al., "Exendin–4, a New Peptide from *Heloderma Suspectum* Venom, Potentiates Cholecystokinin–Induced Amylase Release from Rat Pancreatic Acini," *Regulatory Peptides,* 41:149–56 (1992).

O'Halloran, et al., "Glucagon–like Peptide–1 (7–36)–NH$_2$: A Physiological Inhibitor of Gastic Acid Secretion in Man," J. Endocrinol. 126(1):169–73 (1990).

Ørskov, et al., "Biological Effects and Metabolic Rates of Glucagonlike Peptide–1 7–36 Amide and Glucagonlike Peptide–1 7–37 in Healthy Subjects Are Indistinguishable," *Diabetes* 42:658–61 (1993).

Passa, P., et al., "Mechanisms Suppressing Glucagon Secretion in Glucagonomas," *Diabetologia,* 19(3):305 [abstract 298 ] (1980).

Schepp, et al., "Exendin–4 and Exendin–(9–39)NH$_2$: Agonist and Antagonist, Respectively, at the Rat Parietal Cell Receptor for Glucagon–like Peptide–1–(7–36)NH$_2$," *Eur. J. Pharm.,* 269:183–91 (1994).

Schjoldager, et al., "GLP–1 (Glucagon–like Peptide 1) and Truncated GLP–1, Fragments of Human Proglucagon, Inhibit Gastric Acid Secretion in Humans," *Dig. Dis. Sci.,* 34(5):703–8 (1989).

Singh, et al., "Use of $^{125}$I–[Y$^{39}$] exendin–4 to Characterize Exendin Receptors on Dispersed Pancreatic Acini and Gastric Chief Cells from Guinea Pig," Regul. Pep., 53:47–59 (1994).

Stower, et al., "A Trial of Glucagon in the Treatment of Painful Biliary Tract Disease," *Br. J. Surg.,* 69:591–2 (1982).

Turton, M.D., et al., "A Role for Glucagon–like Peptide–1 in the Central Regulation of Feeding," *Nature,* 379:69–72 (1996).

Wettergren, et al., "Truncated GLP–1 (Proglucagon 78–107–Amide Inhibits Gastric and Pancreatic Functions in Man," *Dig. Dis. Sci.,* 38(4):665–73 (1993).

Willms et al., "Gastric Emptying, Glucose Responses, and Insulin Secretion after a Liquid Test Mal: Effects of Exogenous Glucagon–Like Peptide–1 (GLF–1)–(7–36) Amide in Type 2 (Noninsulin–Dependent) Diabetic Patients," *J. Clin. Endocrinol. Metab.,* 81(1):327–32 (1996).

* cited by examiner

His Ser Asp Gly Thr Phe Thr Ser Asp Leu Ser Lys Gln Met Glu Glu
1                       5                      10                     15
Glu Ala Val Arg Leu Phe Ile Glu Trp Leu Lys Asn Gly Gly Pro Ser
                        20                      25                     30
Ser Gly Ala Pro Pro Ser-NH₂
             35

Fig. 1

His Gly Glu Gly Thr Phe Thr Ser Asp Leu Ser Lys Gln Met Glu Glu
1                       5                      10                     15
Glu Ala Val Arg Leu Phe Ile Glu Trp Leu Lys Asn Gly Gly Pro Ser
                        20                      25                     30
Ser Gly Ala Pro Pro Ser-NH₂
             35

Fig. 2

Xaa₁ Xaa₂ Xaa₃ Gly Thr Xaa₄ Xaa₅ Xaa₆ Xaa₇ Xaa₈ Ser Lys Gln Xaa₉ Glu Glu Ala Val Arg Leu
Xaa₁₀ Xaa₁₁ Xaa₁₂ Xaa₁₃ Leu Lys Asn Gly Gly Xaa₁₄ Ser Ser Gly Ala Xaa₁₅ Xaa₁₆ Xaa₁₇ Xaa₁₈-Z

| Compound (SEQ ID NO) | Xaa₁ | Xaa₂ | Xaa₃ | Xaa₄ | Xaa₅ | Xaa₆ | Xaa₇ | Xaa₈ | Xaa₉ | Xaa₁₀ | Xaa₁₁ | Xaa₁₂ | Xaa₁₃ | Xaa₁₄ | Xaa₁₅ | Xaa₁₆ | Xaa₁₇ | Xaa₁₈ | Z |
|---|---|---|---|---|---|---|---|---|---|---|---|---|---|---|---|---|---|---|---|
| 1 [10] | His | Gly | Glu | Phe | Thr | Ser | Asp | Leu | Leu | Phe | Ile | Glu | Phe | Pro | Pro | Pro | Pro | Ser | NH₂ |
| 2 [11] | His | Gly | Glu | Phe | Thr | Ser | Asp | Leu | Leu | Phe | Ile | Glu | Trp | Pro | Pro | Pro | Pro | Ser | NH₂ |
| 3 [12] | His | Gly | Glu | Phe | Thr | Ser | Asp | Leu | Met | Phe | Ile | Glu | Phe | Pro | Pro | Pro | Pro | Ser | NH₂ |
| 4 [13] | Tyr | Gly | Glu | Phe | Thr | Ser | Asp | Leu | Met | Phe | Ile | Glu | Trp | Pro | Pro | Pro | Pro | Ser | NH₂ |
| 5 [14] | His | Gly | Glu | Phe | Thr | Ser | Asp | Leu | Met | Phe | Ile | Glu | Trp | Pro | Pro | Pro | Pro | Tyr | NH₂ |
| 6 [15] | His | Gly | Asp | Phe | Thr | Ser | Asp | Leu | Met | Phe | Ile | Glu | Trp | Pro | Pro | Pro | Pro | Ser | NH₂ |
| 7 [16] | His | Gly | Glu | naph | Thr | Ser | Asp | Leu | Met | Phe | Ile | Glu | Trp | Pro | Pro | Pro | Pro | Ser | NH₂ |
| 8 [17] | His | Gly | Glu | Phe | Ser | Ser | Asp | Leu | Met | Phe | Ile | Glu | Trp | Pro | Pro | Pro | Pro | Ser | NH₂ |
| 9 [18] | His | Gly | Glu | Phe | Thr | Thr | Asp | Leu | Met | Phe | Ile | Glu | Trp | Pro | Pro | Pro | Pro | Ser | NH₂ |
| 10 [19] | His | Gly | Glu | Phe | Thr | Ser | Glu | Leu | Met | Phe | Ile | Glu | Trp | Pro | Pro | Pro | Pro | Ser | NH₂ |
| 11 [20] | His | Gly | Glu | Phe | Thr | Ser | Asp | Leu | Met | Phe | Ile | Glu | Phe | Pro | Pro | Pro | Pro | Ser | NH₂ |
| 12 [21] | His | Gly | Glu | Phe | Thr | Ser | Asp | pGly | Met | Phe | Ile | Glu | Trp | Pro | Pro | Pro | Pro | Ser | NH₂ |
| 13 [22] | His | Gly | Glu | Phe | Thr | Ser | Asp | pGly | Leu | Phe | Ile | Glu | Phe | Pro | Pro | Pro | Pro | Ser | NH₂ |
| 14 [23] | His | Gly | Glu | Phe | Thr | Ser | Asp | Leu | pGly | Phe | Ile | Glu | Trp | Pro | Pro | Pro | Pro | Ser | NH₂ |
| 15 [24] | His | Gly | Glu | Phe | Thr | Ser | Asp | Leu | pGly | Phe | Ile | Glu | Phe | Pro | Pro | Pro | Pro | Ser | NH₂ |
| 16 [25] | His | Gly | Glu | Phe | Thr | Ser | Asp | Leu | Met | naph | Ile | Glu | Trp | Pro | Pro | Pro | Pro | Ser | NH₂ |
| 17 [26] | His | Gly | Glu | Phe | Thr | Ser | Asp | Leu | Met | Phe | Val | Glu | Trp | Pro | Pro | Pro | Pro | Ser | NH₂ |

Fig. 3A

| Compound [SEQ.ID.NO] | Xaa₁ | Xaa₂ | Xaa₃ | Xaa₄ | Xaa₅ | Xaa₆ | Xaa₇ | Xaa₈ | Xaa₉ | Xaa₁₀ | Xaa₁₁ | Xaa₁₂ | Xaa₁₃ | Xaa₁₄ | Xaa₁₅ | Xaa₁₆ | Xaa₁₇ | Xaa₁₈ | Z |
|---|---|---|---|---|---|---|---|---|---|---|---|---|---|---|---|---|---|---|---|
| 18 [27] | His | Gly | Glu | Phe | Thr | Ser | Asp | Leu | Leu | Phe | Val | Glu | Phe | Pro | Pro | Pro | Pro | Ser | NH₂ |
| 19 [28] | His | Gly | Glu | Phe | Thr | Ser | Asp | Leu | Leu | Phe | tBuG | Glu | Trp | Pro | Pro | Pro | Pro | Ser | NH₂ |
| 20 [29] | His | Gly | Glu | Phe | Thr | Ser | Asp | Leu | Met | Phe | tBuG | Glu | Phe | Pro | Pro | Pro | Pro | Ser | NH₂ |
| 21 [30] | His | Gly | Glu | Phe | Thr | Ser | Asp | Leu | Met | Phe | Ile | Asp | Trp | Pro | Pro | Pro | Pro | Ser | NH₂ |
| 22 [31] | His | Ala | Glu | Phe | Thr | Ser | Asp | Leu | Leu | Phe | Ile | Glu | Phe | Pro | Pro | Pro | Pro | Ser | NH₂ |
| 23 [32] | His | Gly | Glu | Phe | Thr | Ser | Asp | Leu | Met | Phe | Ile | Glu | Trp | tPro | tPro | tPro | Pro | Ser | NH₂ |
| 24 [33] | His | Gly | Glu | Phe | Thr | Ser | Asp | Leu | Met | Phe | Ile | Glu | Trp | Pro | tPro | tPro | tPro | Ser | NH₂ |
| 25 [34] | His | Gly | Glu | Phe | Thr | Ser | Asp | Leu | Met | Phe | Ile | Glu | Trp | hPro | hPro | hPro | Pro | Ser | NH₂ |
| 26 [35] | His | Gly | Glu | Phe | Thr | Ser | Asp | Leu | Leu | Phe | Ile | Glu | Phe | Pro | hPro | hPro | Pro | Ser | NH₂ |
| 27 [36] | His | Gly | Glu | Phe | Thr | Ser | Asp | Leu | Met | Phe | Ile | Glu | Phe | tPro | tPro | tPro | Pro | Ser | NH₂ |
| 28 [37] | His | Gly | Glu | Phe | Thr | Ser | Asp | Leu | Leu | Phe | Ile | Glu | Phe | hPro | hPro | hPro | Pro | Ser | NH₂ |
| 29 [38] | His | Gly | Glu | Phe | Thr | Ser | Asp | Leu | Met | Phe | Ile | Glu | Trp | MeAla | MeAla | MeAla | MeAla | Ser | NH₂ |
| 30 [39] | His | Gly | Glu | Phe | Thr | Ser | Asp | Leu | Met | Phe | Ile | Glu | Trp | Pro | MeAla | MeAla | MeAla | Ser | NH₂ |
| 31 [40] | His | Gly | Glu | Phe | Thr | Ser | Asp | Leu | Leu | Phe | Ile | Glu | Phe | MeAla | MeAla | MeAla | MeAla | Ser | NH₂ |

Fig. 3B

| Amino Acid Position | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| Compound 1 | His | Gly | Glu | Gly | Thr | Phe | Thr | Ser | Asp | Leu | Ser | Lys | Gln | Met | Glu | Glu | Glu | Ala | Val | Arg |
| Compound 2 | His | Gly | Glu | Gly | Thr | Phe | Thr | Ser | Asp | Leu | Ser | Lys | Gln | Met | Glu | Glu | Glu | Ala | Val | Arg |
| Compound 3 | His | Gly | Glu | Gly | Thr | Phe | Thr | Ser | Asp | Leu | Ser | Lys | Gln | Leu | Glu | Glu | Glu | Ala | Val | Arg |
| Compound 4 | His | Ala | Glu | Gly | Thr | Phe | Thr | Ser | Asp | Leu | Ser | Lys | Gln | Leu | Glu | Glu | Glu | Ala | Val | Arg |
| Compound 5 | His | Gly | Glu | Gly | Ala | Phe | Thr | Ser | Asp | Leu | Ser | Lys | Gln | Leu | Glu | Glu | Glu | Ala | Val | Arg |
| Compound 6 | His | Gly | Glu | Gly | Thr | Ala | Thr | Ser | Asp | Leu | Ser | Lys | Gln | Leu | Glu | Glu | Glu | Ala | Val | Arg |
| Compound 7 | His | Gly | Glu | Gly | Thr | Phe | Ala | Ser | Asp | Leu | Ser | Lys | Gln | Leu | Glu | Glu | Glu | Ala | Val | Arg |
| Compound 8 | His | Gly | Glu | Gly | Thr | Phe | Thr | Ala | Asp | Leu | Ser | Lys | Gln | Leu | Glu | Glu | Glu | Ala | Val | Arg |
| Compound 9 | His | Gly | Glu | Gly | Thr | Phe | Thr | Ser | Asp | Ala | Ser | Lys | Gln | Leu | Glu | Glu | Glu | Ala | Val | Arg |
| Compound 10 | His | Gly | Glu | Gly | Thr | Phe | Thr | Ser | Asp | Leu | Ala | Lys | Gln | Leu | Glu | Glu | Glu | Ala | Val | Arg |
| Compound 11 | His | Gly | Glu | Gly | Thr | Phe | Thr | Ser | Asp | Leu | Ser | Ala | Gln | Leu | Glu | Glu | Glu | Ala | Val | Arg |
| Compound 12 | His | Gly | Glu | Gly | Thr | Phe | Thr | Ser | Asp | Leu | Ser | Lys | Ala | Leu | Glu | Glu | Glu | Ala | Val | Arg |
| Compound 13 | His | Gly | Glu | Gly | Thr | Phe | Thr | Ser | Asp | Leu | Ser | Lys | Gln | Ala | Glu | Glu | Glu | Ala | Val | Arg |
| Compound 14 | His | Gly | Glu | Gly | Thr | Phe | Thr | Ser | Asp | Leu | Ser | Lys | Gln | Leu | Ala | Glu | Glu | Ala | Val | Arg |
| Compound 15 | His | Gly | Glu | Gly | Thr | Phe | Thr | Ser | Asp | Leu | Ser | Lys | Gln | Leu | Glu | Ala | Glu | Ala | Val | Arg |
| Compound 16 | His | Gly | Glu | Gly | Thr | Phe | Thr | Ser | Asp | Leu | Ser | Lys | Gln | Leu | Glu | Glu | Ala | Ala | Val | Arg |
| Compound 17 | His | Gly | Glu | Gly | Thr | Phe | Thr | Ser | Asp | Leu | Ser | Lys | Gln | Leu | Glu | Glu | Glu | Ala | Val | Arg |
| Compound 18 | His | Gly | Glu | Gly | Thr | Phe | Thr | Ser | Asp | Leu | Ser | Lys | Gln | Leu | Glu | Glu | Glu | Ala | Ala | Arg |
| Compound 19 | His | Gly | Glu | Gly | Thr | Phe | Thr | Ser | Asp | Leu | Ser | Lys | Gln | Leu | Glu | Glu | Glu | Ala | Val | Ala |
| Compound 20 | His | Gly | Glu | Gly | Thr | Phe | Thr | Ser | Asp | Leu | Ser | Lys | Gln | Leu | Glu | Glu | Glu | Ala | Val | Arg |

Fig. 4A1

| Amino Acid Position | 21 | 22 | 23 | 24 | 25 | 26 | 27 | 28 | 29 | 30 | 31 | 32 | 33 | 34 | 35 | 36 | 37 | 38 | 39 |
|---|---|---|---|---|---|---|---|---|---|---|---|---|---|---|---|---|---|---|---|
| Compound 1 | Leu | Phe | Ile | Glu | Trp | Leu | Lys | Asn | Gly | Gly | NH2 | | | | | | | | |
| Compound 2 | Leu | Phe | Ile | Glu | Trp | Leu | Lys | Asn | NH2 | | | | | | | | | | |
| Compound 3 | Leu | Phe | Ile | Glu | Phe | Leu | Lys | Asn | NH2 | | | | | | | | | | |
| Compound 4 | Leu | Phe | Ile | Glu | Phe | Leu | Lys | Asn | NH2 | | | | | | | | | | |
| Compound 5 | Leu | Phe | Ile | Glu | Phe | Leu | Lys | Asn | NH2 | | | | | | | | | | |
| Compound 6 | Leu | Phe | Ile | Glu | Phe | Leu | Lys | Asn | NH2 | | | | | | | | | | |
| Compound 7 | Leu | Phe | Ile | Glu | Phe | Leu | Lys | Asn | NH2 | | | | | | | | | | |
| Compound 8 | Leu | Phe | Ile | Glu | Phe | Leu | Lys | Asn | NH2 | | | | | | | | | | |
| Compound 9 | Leu | Phe | Ile | Glu | Phe | Leu | Lys | Asn | NH2 | | | | | | | | | | |
| Compound 10 | Leu | Phe | Ile | Glu | Phe | Leu | Lys | Asn | NH2 | | | | | | | | | | |
| Compound 11 | Leu | Phe | Ile | Glu | Phe | Leu | Lys | Asn | NH2 | | | | | | | | | | |
| Compound 12 | Leu | Phe | Ile | Glu | Phe | Leu | Lys | Asn | NH2 | | | | | | | | | | |
| Compound 13 | Leu | Phe | Ile | Glu | Phe | Leu | Lys | Asn | NH2 | | | | | | | | | | |
| Compound 14 | Leu | Phe | Ile | Glu | Phe | Leu | Lys | Asn | NH2 | | | | | | | | | | |
| Compound 15 | Leu | Phe | Ile | Glu | Phe | Leu | Lys | Asn | NH2 | | | | | | | | | | |
| Compound 16 | Leu | Phe | Ile | Glu | Phe | Leu | Lys | Asn | NH2 | | | | | | | | | | |
| Compound 17 | Leu | Phe | Ile | Glu | Phe | Leu | Lys | Asn | NH2 | | | | | | | | | | |
| Compound 18 | Ala | Phe | Ile | Glu | Phe | Leu | Lys | Asn | NH2 | | | | | | | | | | |
| Compound 19 | Leu | Phe | Ile | Ala | Phe | Leu | Lys | Asn | NH2 | | | | | | | | | | |
| Compound 20 | Leu | Phe | Ile | Glu | Ala | Leu | Lys | Asn | NH2 | | | | | | | | | | |

Fig. 4A2

| Amino Acid Position | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| Compound 21 | His | Gly | Glu | Gly | Thr | Phe | Thr | Ser | Asp | Leu | Ser | Lys | Gln | Leu | Glu | Glu | Glu | Ala | Val | Arg |
| Compound 22 | His | Gly | Glu | Gly | Thr | Phe | Thr | Ser | Asp | Leu | Ser | Lys | Gln | Leu | Glu | Glu | Glu | Ala | Val | Arg |
| Compound 23 | His | Gly | Glu | Gly | Thr | Phe | Thr | Ser | Asp | Leu | Ser | Lys | Gln | Leu | Glu | Glu | Glu | Ala | Val | Arg |
| Compound 24 | His | Gly | Glu | Gly | Thr | Phe | Thr | Ser | Asp | Leu | Ser | Lys | Gln | Met | Glu | Glu | Glu | Ala | Val | Arg |
| Compound 25 | His | Gly | Glu | Gly | Thr | Phe | Thr | Ser | Asp | Leu | Ser | Lys | Gln | Leu | Glu | Glu | Glu | Ala | Val | Arg |
| Compound 26 | His | Gly | Glu | Gly | Thr | Phe | Thr | Ser | Asp | Leu | Ser | Lys | Gln | Met | Glu | Glu | Glu | Ala | Val | Arg |
| Compound 27 | His | Gly | Glu | Gly | Thr | Phe | Thr | Ser | Asp | Leu | Ser | Lys | Gln | Leu | Glu | Glu | Glu | Ala | Val | Arg |
| Compound 28 | His | Gly | Glu | Gly | Thr | Phe | Thr | Ser | Asp | Leu | Ser | Lys | Gln | Met | Glu | Glu | Glu | Ala | Val | Arg |
| Compound 29 | His | Gly | Glu | Gly | Thr | Phe | Thr | Ser | Asp | Leu | Ser | Lys | Gln | Leu | Glu | Glu | Glu | Ala | Val | Arg |
| Compound 30 | His | Gly | Glu | Gly | Thr | Phe | Thr | Ser | Asp | Leu | Ser | Lys | Gln | Met | Glu | Glu | Glu | Ala | Val | Arg |
| Compound 31 | His | Gly | Glu | Gly | Thr | Phe | Thr | Ser | Asp | Leu | Ser | Lys | Gln | Leu | Glu | Glu | Glu | Ala | Val | Arg |
| Compound 32 | His | Gly | Glu | Gly | Thr | Phe | Thr | Ser | Asp | Leu | Ser | Lys | Gln | Met | Glu | Glu | Glu | Ala | Val | Arg |
| Compound 33 | His | Gly | Glu | Gly | Thr | Phe | Thr | Ser | Asp | Leu | Ser | Lys | Gln | Leu | Glu | Glu | Glu | Ala | Val | Arg |
| Compound 34 | His | Gly | Glu | Gly | Thr | Phe | Thr | Ser | Asp | Leu | Ser | Lys | Gln | Met | Glu | Glu | Glu | Ala | Val | Arg |
| Compound 35 | His | Gly | Glu | Gly | Thr | Phe | Thr | Ser | Asp | Leu | Ser | Lys | Gln | Leu | Glu | Glu | Glu | Ala | Val | Arg |
| Compound 36 | His | Gly | Glu | Gly | Thr | Phe | Thr | Ser | Asp | Leu | Ser | Lys | Gln | Met | Glu | Glu | Glu | Ala | Val | Arg |
| Compound 37 | His | Gly | Glu | Gly | Thr | Phe | Thr | Ser | Asp | Leu | Ser | Lys | Gln | Leu | Glu | Glu | Glu | Ala | Val | Arg |
| Compound 38 | His | Gly | Glu | Gly | Thr | Phe | Thr | Ser | Asp | Leu | Ser | Lys | Gln | Met | Glu | Glu | Glu | Ala | Val | Arg |
| Compound 39 | His | Gly | Glu | Gly | Thr | Phe | Thr | Ser | Asp | Leu | Ser | Lys | Gln | Leu | Glu | Glu | Glu | Ala | Val | Arg |
| Compound 40 | His | Gly | Glu | Gly | Thr | Phe | Thr | Ser | Asp | Leu | Ser | Lys | Gln | Leu | Glu | Glu | Glu | Ala | Val | Arg |
| Compound 41 | His | Gly | Glu | Gly | Thr | Phe | Thr | Ser | Asp | Leu | Ser | Lys | Gln | Met | Glu | Glu | Glu | Ala | Val | Arg |

Fig. 4A3

| Amino Acid Position | 21 | 22 | 23 | 24 | 25 | 26 | 27 | 28 | 29 | 30 | 31 | 32 | 33 | 34 | 35 | 36 | 37 | 38 | 39 |
|---|---|---|---|---|---|---|---|---|---|---|---|---|---|---|---|---|---|---|---|
| Compound 21 | Leu | Phe | Ile | Glu | Phe | Ala | Lys | Asn | NH2 | | | | | | | | | | |
| Compound 22 | Leu | Phe | Ile | Glu | Phe | Leu | Ala | Asn | NH2 | | | | | | | | | | |
| Compound 23 | Leu | Phe | Ile | Glu | Phe | Leu | Lys | Ala | NH2 | | | | | | | | | | |
| Compound 24 | Leu | Phe | Ile | Glu | Trp | Leu | Lys | Asn | Gly | Gly | Pro | Ser | Ser | Gly | Ala | Pro | Pro | Pro | NH2 |
| Compound 25 | Leu | Phe | Ile | Glu | Phe | Leu | Lys | Asn | Gly | Gly | Pro | Ser | Ser | Gly | Ala | Pro | Pro | Pro | NH2 |
| Compound 26 | Leu | Phe | Ile | Glu | Trp | Leu | Lys | Asn | Gly | Gly | Pro | Ser | Ser | Gly | Ala | Pro | Pro | NH2 | |
| Compound 27 | Leu | Phe | Ile | Glu | Phe | Leu | Lys | Asn | Gly | Gly | Pro | Ser | Ser | Gly | Ala | Pro | Pro | NH2 | |
| Compound 28 | Leu | Phe | Ile | Glu | Trp | Leu | Lys | Asn | Gly | Gly | Pro | Ser | Ser | Gly | Ala | Pro | NH2 | | |
| Compound 29 | Leu | Phe | Ile | Glu | Phe | Leu | Lys | Asn | Gly | Gly | Pro | Ser | Ser | Gly | Ala | Pro | NH2 | | |
| Compound 30 | Leu | Phe | Ile | Glu | Trp | Leu | Lys | Asn | Gly | Gly | Pro | Ser | Ser | Gly | Ala | NH2 | | | |
| Compound 31 | Leu | Phe | Ile | Glu | Phe | Leu | Lys | Asn | Gly | Gly | Pro | Ser | Ser | Gly | Ala | NH2 | | | |
| Compound 32 | Leu | Phe | Ile | Glu | Trp | Leu | Lys | Asn | Gly | Gly | Pro | Ser | Ser | Gly | NH2 | | | | |
| Compound 33 | Leu | Phe | Ile | Glu | Phe | Leu | Lys | Asn | Gly | Gly | Pro | Ser | Ser | Gly | NH2 | | | | |
| Compound 34 | Leu | Phe | Ile | Glu | Trp | Leu | Lys | Asn | Gly | Gly | Pro | Ser | Ser | NH2 | | | | | |
| Compound 35 | Leu | Phe | Ile | Glu | Phe | Leu | Lys | Asn | Gly | Gly | Pro | Ser | Ser | NH2 | | | | | |
| Compound 36 | Leu | Phe | Ile | Glu | Trp | Leu | Lys | Asn | Gly | Gly | Pro | Ser | NH2 | | | | | | |
| Compound 37 | Leu | Phe | Ile | Glu | Phe | Leu | Lys | Asn | Gly | Gly | Pro | Ser | NH2 | | | | | | |
| Compound 38 | Leu | Phe | Ile | Glu | Trp | Leu | Lys | Asn | Gly | Gly | Pro | NH2 | | | | | | | |
| Compound 39 | Leu | Phe | Ile | Glu | Phe | Leu | Lys | Asn | Gly | Gly | Pro | NH2 | | | | | | | |
| Compound 40 | Leu | Phe | Ile | Glu | Phe | Leu | Lys | Asn | Gly | Gly | NH2 | | | | | | | | |
| Compound 41 | Leu | Phe | Ile | Glu | Trp | Leu | Lys | Asn | Gly | NH2 | | | | | | | | | |

Fig. 4A4

| Amino Acid Position | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| Compound 42 | His | Gly | Glu | Gly | Thr | Phe | Thr | Ser | Asp | Leu | Ser | Lys | Gln | Leu | Glu | Glu | Glu | Ala | Val | Arg |
| Compound 43 | His | Gly | Glu | Gly | Thr | Phe | Thr | Ser | Asp | Leu | Ser | Lys | Gln | Met | Glu | Glu | Glu | Ala | Val | Arg |
| Compound 44 | His | Gly | Glu | Gly | Thr | Phe | Thr | Ser | Asp | Leu | Ser | Lys | Gln | Met | Glu | Glu | Glu | Ala | Val | Arg |
| Compound 45 | His | Gly | Glu | Gly | Thr | Phe | Thr | Ser | Asp | Leu | Ser | Lys | Gln | Met | Glu | Glu | Glu | Ala | Val | Arg |
| Compound 46 | His | Gly | Glu | Gly | Thr | Phe | Thr | Ser | Asp | Leu | Ser | Lys | Gln | Met | Glu | Glu | Glu | Ala | Val | Arg |
| Compound 47 | His | Gly | Glu | Gly | Thr | Phe | Thr | Ser | Asp | Leu | Ser | Lys | Gln | Met | Glu | Glu | Glu | Ala | Val | Arg |
| Compound 48 | His | Gly | Glu | Gly | Thr | Phe | Thr | Ser | Asp | Leu | Ser | Lys | Gln | Met | Glu | Glu | Glu | Ala | Val | Arg |
| Compound 49 | Arg | Gly | Asp | Gly | Thr | Phe | Thr | Ser | Asp | Leu | Ser | Lys | Gln | Met | Glu | Glu | Glu | Ala | Val | Arg |
| Compound 50 | His | Gly | Glu | Gly | Thr | Phe | Thr | Ser | Asp | Leu | Ser | Lys | Gln | Met | Glu | Glu | Glu | Ala | Val | Arg |
| Compound 51 | His | Gly | Glu | Gly | Thr | naph | Thr | Ser | Asp | Leu | Ser | Lys | Gln | Met | Glu | Glu | Glu | Ala | Val | Arg |
| Compound 52 | His | Gly | Glu | Gly | Thr | Phe | Ser | Ser | Asp | Leu | Ser | Lys | Gln | Met | Glu | Glu | Glu | Ala | Val | Arg |
| Compound 53 | His | Gly | Glu | Gly | Thr | Phe | Ser | Thr | Glu | Leu | Ser | Lys | Gln | Met | Ala | Glu | Glu | Ala | Val | Arg |
| Compound 54 | His | Gly | Glu | Gly | Thr | Phe | Thr | Ser | Asp | pGly | Ser | Lys | Gln | Met | Glu | Glu | Glu | Ala | Val | Arg |
| Compound 55 | His | Gly | Glu | Gly | Thr | Phe | Thr | Ser | Asp | Leu | Ser | Lys | Gln | Leu | Glu | Glu | Glu | Ala | Val | Arg |
| Compound 56 | His | Gly | Glu | Gly | Thr | Phe | Thr | Ser | Asp | Leu | Ser | Lys | Gln | Met | Glu | Glu | Glu | Ala | Val | Arg |
| Compound 57 | His | Gly | Glu | Gly | Thr | Phe | Thr | Ser | Asp | Leu | Ser | Lys | Gln | Leu | Glu | Glu | Glu | Ala | Val | Arg |
| Compound 58 | His | Gly | Glu | Gly | Thr | Phe | Thr | Ser | Asp | Leu | Ser | Lys | Gln | Met | Glu | Glu | Glu | Ala | Val | Arg |
| Compound 59 | His | Gly | Glu | Gly | Thr | Phe | Thr | Ser | Asp | Ala | Ser | Lys | Gln | Leu | Glu | Glu | Glu | Ala | Val | Arg |
| Compound 60 | His | Gly | Glu | Gly | Thr | Phe | Thr | Ser | Asp | Ala | Ser | Lys | Gln | Met | Glu | Glu | Glu | Ala | Val | Arg |
| Compound 61 | His | Gly | Glu | Gly | Thr | Phe | Thr | Ser | Asp | Ala | Ser | Lys | Gln | Met | Glu | Glu | Glu | Ala | Val | Arg |

Fig. 4B1

| Amino Acid Position | 21 | 22 | 23 | 24 | 25 | 26 | 27 | 28 | 29 | 30 | 31 | 32 | 33 | 34 | 35 | 36 | 37 | 38 | 39 |
|---|---|---|---|---|---|---|---|---|---|---|---|---|---|---|---|---|---|---|---|
| Compound 42 | Leu | Phe | Ile | Glu | Phe | Leu | Lys | Asn | Gly | NH2 | | | | | | | | | |
| Compound 43 | Leu | Phe | Ile | Glu | Trp | Leu | Lys | Asn | Gly | Gly | tPro | Ser | Ser | Gly | Ala | tPro | tPro | tPro | NH2 |
| Compound 44 | Leu | Phe | Ile | Glu | Trp | Leu | Lys | Asn | Gly | Gly | Pro | Ser | Ser | Gly | Ala | tPro | tPro | tPro | NH2 |
| Compound 45 | Leu | Phe | Ile | Glu | Trp | Leu | Lys | Asn | Gly | Gly | Nme | Ser | Ser | Gly | Ala | Pro | Pro | NH2 | |
| Compound 46 | Leu | Phe | Ile | Glu | Trp | Leu | Lys | Asn | Gly | Gly | Nme | Ser | Ser | Gly | Ala | Nme | Nme | NH2 | |
| Compound 47 | Leu | Phe | Ile | Glu | Trp | Leu | Lys | Asn | Gly | Gly | hPro | Ser | Ser | Gly | Ala | hPro | hPro | NH2 | |
| Compound 48 | Leu | Phe | Ile | Glu | Trp | Leu | Lys | Asn | Gly | Gly | hPro | Ser | Ser | Gly | Ala | hPro | NH2 | | |
| Compound 49 | Leu | Phe | Ile | Glu | Trp | Leu | Lys | Asn | Gly | Gly | Pro | Ser | Ser | Gly | Ala | NH2 | | | |
| Compound 50 | Leu | Phe | Ile | Glu | Trp | Leu | Lys | Asn | Gly | NH2 | | | | | | | | | |
| Compound 51 | Leu | Phe | Ile | Glu | Phe | Leu | Lys | Asn | NH2 | | | | | | | | | | |
| Compound 52 | Leu | Phe | Ile | Glu | Trp | Leu | Lys | Asn | NH2 | | | | | | | | | | |
| Compound 53 | Leu | Phe | Ile | Glu | Trp | Leu | Lys | Asn | NH2 | | | | | | | | | | |
| Compound 54 | Leu | Phe | Ile | Glu | Trp | Leu | Lys | Asn | NH2 | | | | | | | | | | |
| Compound 55 | Leu | Phe | Ile | Glu | Phe | Leu | Lys | Asn | NH2 | | | | | | | | | | |
| Compound 56 | Leu | naph | Ile | Glu | Phe | Leu | Lys | Asn | NH2 | | | | | | | | | | |
| Compound 57 | Leu | Phe | tBug | Glu | Trp | Leu | Lys | Asn | Gly | Gly | | | | | | | | | |
| Compound 58 | Leu | Phe | Ile | Asp | Phe | Leu | Lys | Asn | Gly | Gly | | | | | | | | | |
| Compound 59 | Leu | Phe | Ile | Glu | Phe | Leu | Lys | Asn | Gly | Gly | Pro | Ser | Ser | NH2 | | | | | |
| Compound 60 | Leu | Phe | Ile | Glu | Trp | Leu | Lys | Asn | Gly | NH2 | | | | | | | | | |
| Compound 61 | Leu | Phe | Ile | Glu | Trp | Leu | Lys | Asn | Gly | Gly | hPro | Ser | Ser | Gly | Ala | hPro | hPro | NH2 | |

Fig. 4B2

| Compound No | |
|---|---|
| 62 | 4-Imidazolylpropionyl-Gly Glu Gly Thr Phe Thr Ser Asp Leu Ser Lys Gln Met Glu Glu Glu Ala Val Arg Leu Phe Ile Glu Trp Leu Lys-NH$^E$octanoyl Asn-NH$_2$ |
| 63 | 4-Imidazolylpropionyl-Gly Glu Gly Thr Phe Thr Ser Asp Leu Ser Lys Gln Leu Glu Glu Glu Ala Val Arg Leu Phe Ile Glu Phe Leu Lys-NH$^E$octanoyl Asn-NH$_2$ |
| 64 | 4-Imidazolylpropionyl-Gly Glu Gly Thr Phe Thr Ser Asp Leu Ser Lys Gln Met Glu Glu Glu Ala Val Arg Leu Phe Ile Glu Trp Leu Lys-NH$^E$octanoyl Asn Gly Gly-NH$_2$ |
| 65 | 4-Imidazolylpropionyl-Gly Glu Gly Thr Phe Thr Ser Asp Leu Ser Lys Gln Leu Glu Glu Glu Ala Val Arg Leu Phe Ile Glu Phe Leu Lys-NH$^E$octanoyl Asn Gly Gly-NH$_2$ |
| 66 | 4-Imidazolylpropionyl-Gly Glu Gly Thr Phe Thr Ser Asp Leu Ser Lys Gln Met Glu Glu Glu Ala Val Arg Leu Phe Ile Glu Trp Leu Asn Lys-NH$^E$octanoyl-NH$_2$ |

Fig. 4C

Compound
No.

67  4-Imidazolylpropionyl-Gly Glu Gly Thr Phe Thr Ser Asp Leu Ser Lys Gln Leu Glu Glu Ala Val Arg Leu
    Phe Ile Glu Phe Leu Asn Lys-NH$^E$octanoyl-NH$_2$ 68  4-Imidazolylpropionyl-Gly Glu Gly Thr Phe Thr Ser Asp Leu Ser Lys Gln Met Glu Glu Ala Val Arg Leu
    Phe Ile Glu Trp Leu Asn Lys-NH$^E$octanoyl Gly Gly-NH$_2$ 69  4-Imidazolylpropionyl-Gly Glu Gly Thr Phe Thr Ser Asp Leu Ser Lys Gln Leu Glu Glu Ala Val Arg Leu
    Phe Ile Glu Phe Leu Asn Lys-NH$^E$octanoyl Gly Gly-NH$_2$

Fig. 4D

| Amino Acid Position | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| Compound 70 | Ala | Gly | Glu | Gly | Thr | Phe | Thr | Ser | Asp | Leu | Ser | Lys | Gln | Leu | Glu | Glu | Glu | Ala | Val | Arg |
| Compound 71 | His | Gly | Ala | Gly | Thr | Phe | Thr | Ser | Asp | Leu | Ser | Lys | Gln | Leu | Glu | Glu | Glu | Ala | Val | Arg |
| Compound 72 | His | Gly | Glu | Ala | Thr | Phe | Thr | Ser | Asp | Leu | Ser | Lys | Gln | Leu | Glu | Glu | Glu | Ala | Val | Arg |
| Compound 73 | His | Gly | Glu | Gly | Thr | Phe | Thr | Ser | Ala | Leu | Ser | Lys | Gln | Leu | Glu | Glu | Glu | Ala | Val | Arg |
| Compound 74 | Ala | Gly | Glu | Gly | Thr | Phe | Thr | Ser | Asp | Leu | Ser | Lys | Gln | Met | Glu | Glu | Glu | Ala | Val | Arg |
| Compound 75 | His | Gly | Ala | Gly | Thr | Phe | Thr | Ser | Asp | Leu | Ser | Lys | Gln | Met | Glu | Glu | Glu | Ala | Val | Arg |
| Compound 76 | His | Gly | Glu | Ala | Thr | Phe | Thr | Ser | Asp | Leu | Ser | Lys | Gln | Met | Glu | Glu | Glu | Ala | Val | Arg |
| Compound 77 | His | Gly | Glu | Gly | Thr | Phe | Thr | Ser | Ala | Leu | Ser | Lys | Gln | Met | Glu | Glu | Glu | Ala | Val | Arg |
| Compound 78 | His | Gly | Glu | Gly | Thr | Phe | Thr | Ser | Asp | Leu | Ser | Lys | Gln | Leu | Glu | Glu | Glu | Ala | Val | Arg |
| Compound 79 | Ala | Ala | Glu | Gly | Thr | Phe | Thr | Ser | Asp | Leu | Ser | Lys | Gln | Met | Glu | Glu | Glu | Ala | Val | Arg |
| Compound 80 | Ala | Ala | Glu | Gly | Thr | Phe | Thr | Ser | Asp | Leu | Ser | Lys | Gln | Leu | Glu | Glu | Glu | Ala | Val | Arg |
| Compound 81 | Ala | Gly | Asp | Gly | Thr | Phe | Thr | Ser | Asp | Leu | Ser | Lys | Gln | Met | Glu | Glu | Glu | Ala | Val | Arg |
| Compound 82 | Ala | Gly | Asp | Gly | Thr | Phe | Thr | Ser | Asp | Leu | Ser | Lys | Gln | Leu | Glu | Glu | Glu | Ala | Val | Arg |
| Compound 83 | Ala | Gly | Asp | Gly | Thr | Phe | Thr | Ser | Asp | Leu | Ser | Lys | Gln | Met | Glu | Glu | Glu | Ala | Val | Arg |
| Compound 84 | Ala | Gly | Asp | Gly | Ala | Phe | Thr | Ser | Asp | Leu | Ser | Lys | Gln | Leu | Glu | Glu | Glu | Ala | Val | Arg |
| Compound 85 | Ala | Gly | Asp | Gly | Ala | Phe | Thr | Ser | Asp | Leu | Ser | Lys | Gln | Met | Glu | Glu | Glu | Ala | Val | Arg |
| Compound 86 | Ala | Gly | Asp | Gly | Thr | Nala | Thr | Ser | Asp | Leu | Ser | Lys | Gln | Leu | Glu | Glu | Glu | Ala | Val | Arg |
| Compound 87 | Ala | Gly | Asp | Gly | Thr | Nala | Ser | Ser | Asp | Leu | Ser | Lys | Gln | Met | Glu | Glu | Glu | Ala | Val | Arg |
| Compound 88 | Ala | Gly | Asp | Gly | Thr | Phe | Ser | Ser | Asp | Leu | Ser | Lys | Gln | Leu | Glu | Glu | Glu | Ala | Val | Arg |
| Compound 89 | Ala | Gly | Asp | Gly | Thr | Phe | Thr | Ala | Asp | Leu | Ser | Lys | Gln | Met | Glu | Glu | Glu | Ala | Val | Arg |

Fig. 4E1

| Amino Acid Position | 21 | 22 | 23 | 24 | 25 | 26 | 27 | 28 | 29 | 30 | 31 | 32 | 33 | 34 | 35 | 36 | 37 | 38 | 39 |
|---|---|---|---|---|---|---|---|---|---|---|---|---|---|---|---|---|---|---|---|
| Compound 70 | Leu | Phe | Ile | Glu | Phe | Leu | Lys | Asn | NH2 | | | | | | | | | | |
| Compound 71 | Leu | Phe | Ile | Glu | Phe | Leu | Lys | Asn | NH2 | | | | | | | | | | |
| Compound 72 | Leu | Phe | Ile | Glu | Phe | Leu | Lys | Asn | NH2 | | | | | | | | | | |
| Compound 73 | Leu | Phe | Ile | Glu | Phe | Leu | Lys | Asn | NH2 | | | | | | | | | | |
| Compound 74 | Leu | Phe | Ile | Glu | Trp | Leu | Lys | Asn | NH2 | | | | | | | | | | |
| Compound 75 | Leu | Phe | Ile | Glu | Trp | Leu | Lys | Asn | NH2 | | | | | | | | | | |
| Compound 76 | Leu | Phe | Ile | Glu | Trp | Leu | Lys | Asn | NH2 | | | | | | | | | | |
| Compound 77 | Leu | Phe | Ile | Glu | Trp | Leu | Lys | Asn | NH2 | | | | | | | | | | |
| Compound 78 | Leu | Phe | Ile | Glu | Trp | Leu | Lys | Asn | NH2 | | | | | | | | | | |
| Compound 79 | Leu | Phe | Ile | Glu | Trp | Leu | Lys | Asn | NH2 | | | | | | | | | | |
| Compound 80 | Leu | Phe | Ile | Glu | Phe | Leu | Lys | Asn | NH2 | | | | | | | | | | |
| Compound 81 | Leu | Phe | Ile | Glu | Trp | Leu | Lys | Asn | NH2 | | | | | | | | | | |
| Compound 82 | Leu | Phe | Ile | Glu | Phe | Leu | Lys | Asn | NH2 | | | | | | | | | | |
| Compound 83 | Leu | Phe | Ile | Glu | Trp | Leu | Lys | Asn | NH2 | | | | | | | | | | |
| Compound 84 | Leu | Phe | Ile | Glu | Phe | Leu | Lys | Asn | NH2 | | | | | | | | | | |
| Compound 85 | Leu | Phe | Ile | Glu | Trp | Leu | Lys | Asn | NH2 | | | | | | | | | | |
| Compound 86 | Leu | Phe | Ile | Glu | Trp | Leu | Lys | Asn | NH2 | | | | | | | | | | |
| Compound 87 | Leu | Phe | Ile | Glu | Phe | Leu | Lys | Asn | NH2 | | | | | | | | | | |
| Compound 88 | Leu | Phe | Ile | Glu | Phe | Leu | Lys | Asn | NH2 | | | | | | | | | | |
| Compound 89 | Leu | Phe | Ile | Glu | Trp | Leu | Lys | Asn | NH2 | | | | | | | | | | |

Fig. 4E2

| Amino Acid Position | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| Compound 21 | Ala | Gly | Asp | Gly | Thr | Phe | Thr | Ala | Asp | Leu | Ser | Lys | Gln | Leu | Glu | Glu | Glu | Ala | Val | Arg |
| Compound 22 | Ala | Gly | Asp | Gly | Thr | Phe | Thr | Ser | Ala | Leu | Ser | Lys | Gln | Met | Glu | Glu | Glu | Ala | Val | Arg |
| Compound 23 | Ala | Gly | Asp | Gly | Thr | Phe | Thr | Ser | Ala | Leu | Ser | Lys | Gln | Leu | Glu | Glu | Glu | Ala | Val | Arg |
| Compound 24 | Ala | Gly | Asp | Gly | Thr | Phe | Thr | Ser | Ala | Leu | Ser | Lys | Gln | Met | Glu | Glu | Glu | Ala | Val | Arg |
| Compound 25 | Ala | Gly | Asp | Gly | Thr | Phe | Thr | Ser | Glu | Leu | Ser | Lys | Gln | Leu | Glu | Glu | Glu | Ala | Val | Arg |
| Compound 26 | Ala | Gly | Asp | Gly | Thr | Phe | Thr | Ser | Glu | Leu | Ser | Lys | Gln | Met | Glu | Glu | Glu | Ala | Val | Arg |
| Compound 27 | Ala | Gly | Asp | Gly | Thr | Phe | Thr | Ser | Asp | Ala | Ser | Lys | Gln | Leu | Glu | Glu | Glu | Ala | Val | Arg |
| Compound 28 | Ala | Gly | Asp | Gly | Thr | Phe | Thr | Ser | Asp | Ala | Ser | Lys | Gln | Met | Glu | Glu | Glu | Ala | Val | Arg |
| Compound 29 | Ala | Gly | Asp | Gly | Thr | Phe | Thr | Ser | Asp | Pgly | Ser | Lys | Gln | Leu | Glu | Glu | Glu | Ala | Val | Arg |
| Compound 30 | Ala | Gly | Asp | Gly | Thr | Phe | Thr | Ser | Asp | Pgly | Ser | Lys | Gln | Met | Glu | Glu | Glu | Ala | Val | Arg |
| Compound 31 | Ala | Gly | Asp | Gly | Thr | Phe | Thr | Ser | Asp | Leu | Ala | Lys | Gln | Leu | Glu | Glu | Glu | Ala | Val | Arg |
| Compound 32 | Ala | Gly | Asp | Gly | Thr | Phe | Thr | Ser | Asp | Leu | Ala | Ala | Gln | Met | Glu | Glu | Glu | Ala | Val | Arg |
| Compound 33 | Ala | Gly | Asp | Gly | Thr | Phe | Thr | Ser | Asp | Leu | Ser | Ala | Gln | Leu | Glu | Glu | Glu | Ala | Val | Arg |
| Compound 34 | Ala | Gly | Asp | Gly | Thr | Phe | Thr | Ser | Asp | Leu | Ser | Ala | Gln | Met | Glu | Glu | Glu | Ala | Val | Arg |
| Compound 35 | Ala | Gly | Asp | Gly | Thr | Phe | Thr | Ser | Asp | Leu | Ser | Lys | Ala | Leu | Glu | Glu | Glu | Ala | Val | Arg |

Fig. 4E3

| Amino Acid Position | 21 | 22 | 23 | 24 | 25 | 26 | 27 | 28 | 29 | 30 | 31 | 32 | 33 | 34 | 35 | 36 | 37 | 38 | 39 |
|---|---|---|---|---|---|---|---|---|---|---|---|---|---|---|---|---|---|---|---|
| Compound 21 | Leu | Phe | Ile | Glu | Phe | Leu | Lys | Asn | NH2 | | | | | | | | | | |
| Compound 22 | Leu | Phe | Ile | Glu | Trp | Leu | Lys | Asn | NH2 | | | | | | | | | | |
| Compound 23 | Leu | Phe | Ile | Glu | Phe | Leu | Lys | Asn | NH2 | | | | | | | | | | |
| Compound 24 | Leu | Phe | Ile | Glu | Trp | Leu | Lys | Asn | NH2 | | | | | | | | | | |
| Compound 25 | Leu | Phe | Ile | Glu | Phe | Leu | Lys | Asn | NH2 | | | | | | | | | | |
| Compound 26 | Leu | Phe | Ile | Glu | Trp | Leu | Lys | Asn | NH2 | | | | | | | | | | |
| Compound 27 | Leu | Phe | Ile | Glu | Phe | Leu | Lys | Asn | NH2 | | | | | | | | | | |
| Compound 28 | Leu | Phe | Ile | Glu | Trp | Leu | Lys | Asn | NH2 | | | | | | | | | | |
| Compound 29 | Leu | Phe | Ile | Glu | Phe | Leu | Lys | Asn | NH2 | | | | | | | | | | |
| Compound 30 | Leu | Phe | Ile | Glu | Trp | Leu | Lys | Asn | NH2 | | | | | | | | | | |
| Compound 31 | Leu | Phe | Ile | Glu | Phe | Leu | Lys | Asn | NH2 | | | | | | | | | | |
| Compound 32 | Leu | Phe | Ile | Glu | Trp | Leu | Lys | Asn | NH2 | | | | | | | | | | |
| Compound 33 | Leu | Phe | Ile | Glu | Phe | Leu | Lys | Asn | NH2 | | | | | | | | | | |
| Compound 34 | Leu | Phe | Ile | Glu | Trp | Leu | Lys | Asn | NH2 | | | | | | | | | | |
| Compound 35 | Leu | Phe | Ile | Glu | Phe | Leu | Lys | Asn | NH2 | | | | | | | | | | |

Fig. 4E4

| Amino Acid Position | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| Compound 105 | Ala | Gly | Asp | Gly | Thr | Phe | Thr | Ser | Asp | Leu | Ser | Lys | Gln | Ala | Glu | Glu | Glu | Ala | Val | Arg |
| Compound 106 | Ala | Gly | Asp | Gly | Thr | Phe | Thr | Ser | Asp | Leu | Ser | Lys | Gln | Ala | Glu | Glu | Glu | Ala | Val | Arg |
| Compound 107 | Ala | Gly | Asp | Gly | Thr | Phe | Thr | Ser | Asp | Leu | Ser | Lys | Gln | pGly | Glu | Glu | Glu | Ala | Val | Arg |
| Compound 108 | Ala | Gly | Asp | Gly | Thr | Phe | Thr | Ser | Asp | Leu | Ser | Lys | Gln | pGly | Glu | Glu | Glu | Ala | Val | Arg |
| Compound 109 | Ala | Gly | Asp | Gly | Thr | Phe | Thr | Ser | Asp | Leu | Ser | Lys | Gln | Met | Ala | Glu | Glu | Ala | Val | Arg |
| Compound 110 | Ala | Gly | Asp | Gly | Thr | Phe | Thr | Ser | Asp | Leu | Ser | Lys | Gln | Leu | Ala | Glu | Glu | Ala | Val | Arg |
| Compound 111 | Ala | Gly | Asp | Gly | Thr | Phe | Thr | Ser | Asp | Leu | Ser | Lys | Gln | Met | Glu | Ala | Glu | Ala | Val | Arg |
| Compound 112 | Ala | Gly | Asp | Gly | Thr | Phe | Thr | Ser | Asp | Leu | Ser | Lys | Gln | Leu | Glu | Ala | Glu | Ala | Val | Arg |
| Compound 113 | Ala | Gly | Asp | Gly | Thr | Phe | Thr | Ser | Asp | Leu | Ser | Lys | Gln | Met | Glu | Glu | Ala | Ala | Val | Arg |
| Compound 114 | Ala | Gly | Asp | Gly | Thr | Phe | Thr | Ser | Asp | Leu | Ser | Lys | Gln | Leu | Glu | Glu | Ala | Ala | Val | Arg |
| Compound 115 | Ala | Gly | Asp | Gly | Thr | Phe | Thr | Ser | Asp | Leu | Ser | Lys | Gln | Met | Glu | Glu | Glu | Ala | Ala | Arg |
| Compound 116 | Ala | Gly | Asp | Gly | Thr | Phe | Thr | Ser | Asp | Leu | Ser | Lys | Gln | Leu | Glu | Glu | Glu | Ala | Ala | Arg |
| Compound 117 | Ala | Gly | Asp | Gly | Thr | Phe | Thr | Ser | Asp | Leu | Ser | Lys | Gln | Met | Glu | Glu | Glu | Ala | Val | Ala |
| Compound 118 | Ala | Gly | Asp | Gly | Thr | Phe | Thr | Ser | Asp | Leu | Ser | Lys | Gln | Leu | Glu | Glu | Glu | Ala | Val | Ala |
| Compound 119 | Ala | Gly | Asp | Gly | Thr | Phe | Thr | Ser | Asp | Leu | Ser | Lys | Gln | Met | Glu | Glu | Glu | Ala | Val | Arg |
| Compound 120 | Ala | Gly | Asp | Gly | Thr | Phe | Thr | Ser | Asp | Leu | Ser | Lys | Gln | Leu | Glu | Glu | Glu | Ala | Val | Arg |
| Compound 121 | Ala | Gly | Asp | Gly | Thr | Phe | Thr | Ser | Asp | Leu | Ser | Lys | Gln | Met | Glu | Glu | Glu | Ala | Val | Arg |
| Compound 122 | Ala | Gly | Asp | Gly | Thr | Phe | Thr | Ser | Asp | Leu | Ser | Lys | Gln | Leu | Glu | Glu | Glu | Ala | Val | Arg |
| Compound 123 | Ala | Gly | Asp | Gly | Thr | Phe | Thr | Ser | Asp | Leu | Ser | Lys | Gln | Met | Glu | Glu | Glu | Ala | Val | Arg |
| Compound 124 | Ala | Gly | Asp | Gly | Thr | Phe | Thr | Ser | Asp | Leu | Ser | Lys | Gln | Leu | Glu | Glu | Glu | Ala | Val | Arg |

Fig. 4F1

| Amino Acid Position | 21 | 22 | 23 | 24 | 25 | 26 | 27 | 28 | 29 | 30 | 31 | 32 | 33 | 34 | 35 | 36 | 37 | 38 | 39 |
|---|---|---|---|---|---|---|---|---|---|---|---|---|---|---|---|---|---|---|---|
| Compound 105 | Leu | Phe | Ile | Glu | Trp | Leu | Lys | Asn | NH2 | | | | | | | | | | |
| Compound 106 | Leu | Phe | Ile | Glu | Phe | Leu | Lys | Asn | NH2 | | | | | | | | | | |
| Compound 107 | Leu | Phe | Ile | Glu | Trp | Leu | Lys | Asn | NH2 | | | | | | | | | | |
| Compound 108 | Leu | Phe | Ile | Glu | Phe | Leu | Lys | Asn | NH2 | | | | | | | | | | |
| Compound 109 | Leu | Phe | Ile | Glu | Trp | Leu | Lys | Asn | NH2 | | | | | | | | | | |
| Compound 110 | Leu | Phe | Ile | Glu | Phe | Leu | Lys | Asn | NH2 | | | | | | | | | | |
| Compound 111 | Leu | Phe | Ile | Glu | Trp | Leu | Lys | Asn | NH2 | | | | | | | | | | |
| Compound 112 | Leu | Phe | Ile | Glu | Phe | Leu | Lys | Asn | NH2 | | | | | | | | | | |
| Compound 113 | Leu | Phe | Ile | Glu | Trp | Leu | Lys | Asn | NH2 | | | | | | | | | | |
| Compound 114 | Leu | Phe | Ile | Glu | Phe | Leu | Lys | Asn | NH2 | | | | | | | | | | |
| Compound 115 | Leu | Phe | Ile | Glu | Trp | Leu | Lys | Asn | NH2 | | | | | | | | | | |
| Compound 116 | Leu | Phe | Ile | Glu | Phe | Leu | Lys | Asn | NH2 | | | | | | | | | | |
| Compound 117 | Leu | Phe | Ile | Glu | Trp | Leu | Lys | Asn | NH2 | | | | | | | | | | |
| Compound 118 | Leu | Phe | Ile | Glu | Phe | Leu | Lys | Asn | NH2 | | | | | | | | | | |
| Compound 119 | Ala | Phe | Ile | Glu | Trp | Leu | Lys | Asn | NH2 | | | | | | | | | | |
| Compound 120 | Ala | Phe | Ile | Glu | Phe | Leu | Lys | Asn | NH2 | | | | | | | | | | |
| Compound 121 | Leu | Nala | Ile | Glu | Trp | Leu | Lys | Asn | NH2 | | | | | | | | | | |
| Compound 122 | Leu | Nala | Ile | Glu | Phe | Leu | Lys | Asn | NH2 | | | | | | | | | | |
| Compound 123 | Leu | Phe | Val | Glu | Trp | Leu | Lys | Asn | NH2 | | | | | | | | | | |
| Compound 124 | Leu | Phe | Val | Glu | Phe | Leu | Lys | Asn | NH2 | | | | | | | | | | |

Fig. 4F2

| Amino Acid Position | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| Compound 125 | Ala | Gly | Asp | Gly | Thr | Phe | Thr | Ser | Asp | Leu | Ser | Lys | Gln | Met | Glu | Glu | Glu | Ala | Val | Arg |
| Compound 126 | Ala | Gly | Asp | Gly | Thr | Phe | Thr | Ser | Asp | Leu | Ser | Lys | Gln | Leu | Glu | Glu | Glu | Ala | Val | Arg |
| Compound 127 | Ala | Gly | Asp | Gly | Thr | Phe | Thr | Ser | Asp | Leu | Ser | Lys | Gln | Met | Glu | Glu | Glu | Ala | Val | Arg |
| Compound 128 | Ala | Gly | Asp | Gly | Thr | Phe | Thr | Ser | Asp | Leu | Ser | Lys | Gln | Leu | Glu | Glu | Glu | Ala | Val | Arg |
| Compound 129 | Ala | Gly | Asp | Gly | Thr | Phe | Thr | Ser | Asp | Leu | Ser | Lys | Gln | Met | Glu | Glu | Glu | Ala | Val | Arg |
| Compound 130 | Ala | Gly | Asp | Gly | Thr | Phe | Thr | Ser | Asp | Leu | Ser | Lys | Gln | Leu | Glu | Glu | Glu | Ala | Val | Arg |
| Compound 131 | Ala | Gly | Asp | Gly | Thr | Phe | Thr | Ser | Asp | Leu | Ser | Lys | Gln | Met | Glu | Glu | Glu | Ala | Val | Arg |
| Compound 132 | Ala | Gly | Asp | Gly | Thr | Phe | Thr | Ser | Asp | Leu | Ser | Lys | Gln | Leu | Glu | Glu | Glu | Ala | Val | Arg |
| Compound 133 | Ala | Gly | Asp | Gly | Thr | Phe | Thr | Ser | Asp | Leu | Ser | Lys | Gln | Met | Glu | Glu | Glu | Ala | Val | Arg |
| Compound 134 | Ala | Gly | Asp | Gly | Thr | Phe | Thr | Ser | Asp | Leu | Ser | Lys | Gln | Leu | Glu | Glu | Glu | Ala | Val | Arg |
| Compound 135 | Ala | Gly | Asp | Gly | Thr | Phe | Thr | Ser | Asp | Leu | Ser | Lys | Gln | Met | Glu | Glu | Glu | Ala | Val | Arg |
| Compound 136 | Ala | Gly | Asp | Gly | Thr | Phe | Thr | Ser | Asp | Leu | Ser | Lys | Gln | Leu | Glu | Glu | Glu | Ala | Val | Arg |
| Compound 137 | Ala | Gly | Glu | Gly | Thr | Phe | Thr | Ser | Asp | Leu | Ser | Lys | Gln | Met | Glu | Glu | Glu | Ala | Val | Arg |
| Compound 138 | His | Gly | Ala | Gly | Thr | Phe | Thr | Ser | Asp | Leu | Ser | Lys | Gln | Leu | Glu | Glu | Glu | Ala | Val | Arg |
| Compound 139 | His | Gly | Glu | Ala | Thr | Phe | Thr | Ser | Asp | Leu | Ser | Lys | Gln | Met | Glu | Glu | Glu | Ala | Val | Arg |
| Compound 140 | His | Gly | Glu | Gly | Thr | Phe | Thr | Ser | Ala | Leu | Ser | Lys | Gln | Met | Glu | Glu | Glu | Ala | Val | Arg |

Fig. 4F3

| Amino Acid Position | 21 | 22 | 23 | 24 | 25 | 26 | 27 | 28 | 29 | 30 | 31 | 32 | 33 | 34 | 35 | 36 | 37 | 38 | 39 |
|---|---|---|---|---|---|---|---|---|---|---|---|---|---|---|---|---|---|---|---|
| Compound 125 | Leu | Phe | tGly | Glu | Trp | Leu | Lys | Asn | NH2 | | | | | | | | | | |
| Compound 126 | Leu | Phe | tGly | Glu | Phe | Leu | Lys | Asn | NH2 | | | | | | | | | | |
| Compound 127 | Leu | Phe | Ile | Asp | Trp | Leu | Lys | Asn | NH2 | | | | | | | | | | |
| Compound 128 | Leu | Phe | Ile | Asp | Phe | Leu | Lys | Asn | NH2 | | | | | | | | | | |
| Compound 129 | Leu | Phe | Ile | Glu | Ala | Leu | Lys | Asn | NH2 | | | | | | | | | | |
| Compound 130 | Leu | Phe | Ile | Glu | Ala | Leu | Lys | Asn | NH2 | | | | | | | | | | |
| Compound 131 | Leu | Phe | Ile | Glu | Trp | Ala | Lys | Asn | NH2 | | | | | | | | | | |
| Compound 132 | Leu | Phe | Ile | Glu | Phe | Ala | Lys | Asn | NH2 | | | | | | | | | | |
| Compound 133 | Leu | Phe | Ile | Glu | Trp | Leu | Ala | Asn | NH2 | | | | | | | | | | |
| Compound 134 | Leu | Phe | Ile | Glu | Phe | Leu | Ala | Asn | NH2 | | | | | | | | | | |
| Compound 135 | Leu | Phe | Ile | Glu | Trp | Leu | Lys | Ala | NH2 | | | | | | | | | | |
| Compound 136 | Leu | Phe | Ile | Glu | Phe | Leu | Lys | Ala | NH2 | | | | | | | | | | |
| Compound 137 | Leu | Phe | Ile | Glu | Trp | Leu | Lys | Asn | Gly | Gly | Pro | Ser | Ser | Gly | Ala | Pro | Pro | Pro | NH2 |
| Compound 138 | Leu | Phe | Ile | Glu | Phe | Leu | Lys | Asn | Gly | Gly | Pro | Ser | Ser | Gly | Ala | Pro | Pro | Pro | NH2 |
| Compound 139 | Leu | Phe | Ile | Glu | Trp | Leu | Lys | Asn | Gly | Gly | Pro | Ser | Ser | Gly | Ala | Pro | Pro | Pro | NH2 |
| Compound 140 | Leu | Phe | Ile | Glu | Trp | Leu | Lys | Asn | NH2 | Gly | Pro | Ser | Ser | Gly | Ala | Pro | NH2 | | |

Fig. 4F4

| Amino Acid Position | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| Compound 141 | Ala | Gly | Glu | Gly | Thr | Phe | Thr | Ser | Asp | Ala | Ser | Lys | Gln | Leu | Glu | Glu | Glu | Ala | Val | Arg |
| Compound 142 | Ala | Gly | Glu | Gly | Thr | Phe | Thr | Ser | Asp | Leu | Ser | Lys | Gln | Met | Glu | Glu | Glu | Ala | Val | Arg |
| Compound 143 | His | Gly | Ala | Gly | Thr | Phe | Thr | Ser | Asp | Leu | Ser | Lys | Gln | Leu | Glu | Glu | Glu | Ala | Val | Arg |
| Compound 144 | His | Gly | Glu | Ala | Thr | Phe | Thr | Ser | Asp | Leu | Ser | Lys | Gln | Met | Glu | Glu | Glu | Ala | Val | Arg |
| Compound 145 | His | Gly | Glu | Gly | Thr | Phe | Thr | Ser | Ala | Leu | Ser | Lys | Gln | Met | Glu | Glu | Glu | Ala | Val | Arg |
| Compound 146 | Ala | Gly | Glu | Gly | Thr | Phe | Thr | Ser | Asp | Leu | Ser | Lys | Gln | Met | Glu | Glu | Glu | Ala | Val | Arg |
| Compound 147 | His | Gly | Ala | Gly | Thr | Phe | Thr | Ser | Asp | Leu | Ser | Lys | Gln | Leu | Glu | Glu | Glu | Ala | Val | Arg |
| Compound 148 | His | Gly | Glu | Ala | Thr | Phe | Thr | Ser | Asp | Leu | Ser | Lys | Gln | Met | Glu | Glu | Glu | Ala | Val | Arg |
| Compound 149 | His | Gly | Glu | Gly | Thr | Phe | Thr | Ser | Ala | Leu | Ser | Lys | Gln | Leu | Glu | Glu | Glu | Ala | Val | Arg |
| Compound 150 | Ala | Gly | Glu | Gly | Thr | Phe | Thr | Ser | Asp | Leu | Ser | Lys | Gln | Met | Glu | Glu | Glu | Ala | Val | Arg |
| Compound 151 | His | Gly | Glu | Gly | Thr | Phe | Thr | Ser | Asp | Leu | Ser | Lys | Gln | Met | Glu | Glu | Glu | Ala | Val | Arg |
| Compound 152 | His | Gly | Glu | Gly | Thr | Phe | Thr | Ser | Ala | Leu | Ser | Lys | Gln | Met | Glu | Glu | Glu | Ala | Val | Arg |
| Compound 153 | His | Gly | Glu | Gly | Thr | Phe | Thr | Ser | Asp | Leu | Ser | Lys | Gln | Met | Glu | Glu | Glu | Ala | Val | Arg |
| Compound 154 | Ala | Gly | Glu | Gly | Thr | Phe | Thr | Ser | Asp | Leu | Ser | Lys | Gln | Met | Glu | Glu | Glu | Ala | Val | Arg |
| Compound 155 | His | Gly | Ala | Ala | Thr | Phe | Thr | Ser | Asp | Leu | Ser | Lys | Gln | Met | Glu | Glu | Glu | Ala | Val | Arg |
| Compound 156 | His | Gly | Asp | Gly | Thr | Phe | Thr | Ser | Asp | Leu | Ser | Lys | Gln | Met | Glu | Glu | Glu | Ala | Val | Arg |
| Compound 157 | Ala | Gly | Glu | Gly | Thr | Phe | Thr | Ser | Asp | Leu | Ser | Lys | Gln | Met | Glu | Glu | Glu | Ala | Val | Arg |
| Compound 158 | Ala | Gly | Ala | Gly | Thr | Phe | Thr | Ser | Asp | Leu | Ser | Lys | Gln | Leu | Glu | Glu | Glu | Ala | Val | Arg |

Fig. 4G1

| Amino Acid Position | 21 | 22 | 23 | 24 | 25 | 26 | 27 | 28 | 29 | 30 | 31 | 32 | 33 | 34 | 35 | 36 | 37 | 38 | 39 |
|---|---|---|---|---|---|---|---|---|---|---|---|---|---|---|---|---|---|---|---|
| Compound 141 | Leu | Phe | Ile | Glu | Phe | Leu | Lys | Asn | Gly | Gly | Pro | Ser | Ser | Gly | Ala | Pro | NH2 | | |
| Compound 142 | Leu | Phe | Ile | Glu | Trp | Leu | Lys | Asn | Gly | Gly | Pro | Ser | Ser | Gly | Ala | NH2 | | | |
| Compound 143 | Leu | Phe | Ile | Glu | Phe | Leu | Lys | Asn | Gly | Gly | Pro | Ser | Ser | Gly | Ala | NH2 | | | |
| Compound 144 | Leu | Phe | Ile | Glu | Trp | Leu | Lys | Asn | Gly | Gly | Pro | Ser | Ser | Gly | NH2 | | | | |
| Compound 145 | Leu | Phe | Ile | Glu | Trp | Leu | Lys | Asn | Gly | Gly | Pro | Ser | Ser | NH2 | | | | | |
| Compound 146 | Leu | Phe | Ile | Glu | Trp | Leu | Lys | Asn | Gly | Gly | Pro | Ser | NH2 | | | | | | |
| Compound 147 | Leu | Phe | Ile | Glu | Phe | Leu | Lys | Asn | Gly | Gly | Pro | Ser | NH2 | | | | | | |
| Compound 148 | Leu | Phe | Ile | Glu | Trp | Leu | Lys | Asn | Gly | Gly | Pro | NH2 | | | | | | | |
| Compound 149 | Leu | Phe | Ile | Glu | Phe | Leu | Lys | Asn | Gly | Gly | NH2 | | | | | | | | |
| Compound 150 | Leu | Phe | Ile | Glu | Phe | Leu | Lys | Asn | Gly | NH2 | | | | | | | | | |
| Compound 151 | Leu | Phe | Ile | Glu | Trp | Leu | Lys | Asn | Gly | Gly | tPro | Ser | Ser | Gly | Ala | tPro | tPro | tPro | NH2 |
| Compound 152 | Leu | Phe | Ile | Glu | Trp | Leu | Lys | Asn | Gly | Gly | Pro | Ser | Ser | Gly | Ala | tPro | tPro | tPro | NH2 |
| Compound 153 | Leu | Phe | Ile | Glu | Trp | Leu | Lys | Asn | Gly | Gly | Nme | Ser | Ser | Gly | Ala | Nme | Nme | NH2 | |
| Compound 154 | Leu | Phe | Ile | Glu | Trp | Leu | Lys | Asn | Gly | Gly | hPro | Ser | Ser | Gly | Ala | hPro | NH2 | | |
| Compound 155 | Leu | Phe | Ile | Glu | Trp | Leu | Lys | Asn | Gly | Gly | Pro | Ser | Ser | Gly | Ala | NH2 | | | |
| Compound 156 | Leu | Phe | Ile | Glu | Trp | Leu | Lys | Asn | Gly | Gly | Pro | NH2 | | | | | | | |
| Compound 157 | Leu | Phe | Ile | Glu | Phe | Leu | Lys | Asn | Gly | Gly | Pro | Ser | Ser | Gly | Ala | Pro | Pro | Pro | Ser |
| Compound 158 | Leu | Phe | Ile | Glu | Phe | Leu | Lys | Asn | Gly | Gly | Pro | Ser | Ser | Gly | Ala | Pro | Pro | Pro | Ser |

Fig. 4G2

Compound
No.

159  4-Imidazolylpropionyl-Gly Glu Gly Thr Phe Thr Ser Ala Leu Ser Lys Gln Met Glu Glu Ala Val Arg Leu
    Phe Ile Glu Trp Leu Lys-NH$^E$octanoyl Asn-NH$_2$ 160  4-Imidazolylpropionyl-Gly Glu Gly Thr Phe Thr Ser Ala Leu Ser Lys Gln Leu Glu Glu Ala Val Arg Leu
    Phe Ile Glu Phe Leu Lys-NH$^E$octanoyl Asn-NH$_2$ 161  4-Imidazolylpropionyl-Gly Glu Gly Thr Phe Thr Ser Ala Leu Ser Lys Gln Met Glu Glu Ala Val Arg Leu
    Phe Ile Glu Trp Leu Lys-NH$^E$octanoyl Asn Gly Gly-NH$_2$ 162  4-Imidazolylpropionyl-Gly Glu Gly Thr Phe Thr Ser Ala Leu Ser Lys Gln Leu Glu Glu Ala Val Arg Leu
    Phe Ile Glu Phe Leu Lys-NH$^E$octanoyl Asn Gly Gly-NH$_2$ 163  4-Imidazolylpropionyl-Gly Glu Gly Thr Phe Thr Ser Ala Leu Ser Lys Gln Met Glu Glu Ala Val Arg Leu
    Phe Ile Glu Trp Leu Asn Lys-NH$^E$octanoyl-NH$_2$ 164  4-Imidazolylpropionyl-Gly Glu Gly Thr Phe Thr Ser Ala Leu Ser Lys Gln Leu Glu Glu Ala Val Arg Leu
    Phe Ile Glu Phe Leu Asn Lys-NH$^E$octanoyl-NH$_2$

Fig. 4H

Compound
No.

165  4-Imidazolylpropionyl-Gly Glu Gly Thr Phe Thr Ser Ala Leu Ser Lys Gln Met Glu Glu Ala Val Arg Leu
Phe Ile Glu Trp Leu Asn Lys-NH$^E$octanoyl Gly Gly-NH$_2$ 166  4-Imidazolylpropionyl-Gly Glu Gly Thr Phe Thr Ser Ala Leu Ser Lys Gln Leu Glu Glu Ala Val Arg Leu
Phe Ile Glu Phe Leu Asn Lys-NH$^E$octanoyl Gly Gly-NH$_2$ 167  Ala Gly Glu Gly Thr Phe Thr Ser Asp Leu Ser Lys Gln Met Glu Glu Ala Val Arg Leu Phe Ile Glu Trp
Leu Lys-NH$^E$octanoyl Asn -NH$_2$ 168  Ala Gly Glu Gly Thr Phe Thr Ser Asp Leu Ser Lys Gln Leu Glu Glu Ala Val Arg Leu Phe Ile Glu Phe
Leu Lys-NH$^E$octanoyl Asn -NH$_2$ 169  Ala Gly Glu Gly Thr Phe Thr Ser Asp Leu Ser Lys Gln Met Glu Glu Ala Val Arg Leu Phe Ile Glu Trp
Leu Lys-NH$^E$octanoyl Asn Gly Gly-NH$_2$ 170  Ala Gly Glu Gly Thr Phe Thr Ser Asp Leu Ser Lys Gln Leu Glu Glu Ala Val Arg Leu Phe Ile Glu Phe
Leu Lys-NH$^E$octanoyl Asn Gly Gly-NH$_2$

Fig. 4I

Compound
No.

171  Ala Gly Glu Gly Thr Phe Thr Ser Asp Leu Ser Lys Gln Met Glu Glu Glu Ala Val Arg Leu Phe Ile Glu Trp
     Leu AsnLys-NH$^E$octanoyl-NH$_2$ 172  Ala Gly Glu Gly Thr Phe Thr Ser Asp Leu Ser Lys Gln Leu Glu Glu Glu Ala Val Arg Leu Phe Ile Glu Phe
     Leu Asn Lys-NH$^E$octanoyl-NH$_2$ 173  Ala Gly Glu Gly Thr Phe Thr Ser Asp Leu Ser Lys Gln Met Glu Glu Glu Ala Val Arg Leu Phe Ile Glu Trp
     Leu Asn Lys-NH$^E$octanoyl Gly Gly-NH$_2$ 174  Ala Gly Glu Gly Thr Phe Thr Ser Asp Leu Ser Lys Gln Leu Glu Glu Glu Ala Val Arg Leu Phe Ile Glu Phe
     Leu Asn Lys-NH$^E$octanoyl Gly Gly-NH$_2$

Fig. 4J

METHODS FOR GLUCAGON SUPPRESSION

This application claims priority from U.S. Provisional Application 60/116,380, entitled "Novel Exendin Agonist Formulations and Methods of Administration Thereof," filed Jan. 14, 1999 (and the corresponding PCT application filed Jan. 14, 2000, Serial No. PCT/US00/00902), U.S. Provisional Application 60/132,017, entitled "Methods for Glucagon Suppression," filed Apr. 30, 1999, and U.S. Provisional Application 60/175,365, entitled "Use of Exendins and Agonists Thereof for Modulation of Triglyceride Levels and Treatment of Dyslipidemia," filed Jan. 10, 2000, the contents of which are hereby incorporated by reference in their entireties.

FIELD OF THE INVENTION

The present invention relates to methods of suppressing and/or lowering glucagon in a subject, comprising the administration of an exendin, an exendin agonist, or a modified exendin or exendin agonist having an exendin or exendin agonist peptide linked to one or more polyethylene glycol polymers or other compound useful to decrease renal clearance of the parent peptide. Such methods are useful, for example, in the treatment of hyperglucagonemia and other conditions in which lower levels of glucagon or suppresion of glucagon secretion are of benefit.

BACKGROUND

The following description includes information that may be useful in understanding the present invention. It is not an admission that any of the information provided herein is prior art to the presently claimed invention, or relevant, nor that any of the publications specifically or implicitly referenced are prior art.

The exendins are peptides that are found in the salivary secretions of the Gila monster and the Mexican Beaded Lizard, reptiles that are endogenous to Arizona and Northern Mexico. Exendin-3 [SEQ. ID. NO: 1: His Ser Asp Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala Pro Pro Pro Ser-NH$_2$] is present in the salivary secretions of *Heloderma horridum* (Mexican Beaded Lizard), and exendin-4 [SEQ. ID. NO. 2: His Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala Pro Pro Pro Ser-NH$_2$] is present in the salivary secretions of *Heloderma suspectum* (Gila monster) (Eng, J., et al., *J. Biol. Chem.*, 265:20259–62, 1990; Eng, J., et al., *J. Biol. Chem.*, 267:7402–05, 1992). The amino acid sequence of exendin-3 is shown in FIG. 1. The amino acid sequence of exendin-4 is shown in FIG. 2. Exendin-4 was first thought to be a (potentially toxic) component of the venom. It now appears that exendin-4 is devoid of toxicity, and that it instead is made in salivary glands in the Gila monster.

The exendins have some sequence similarity to several members of the glucagon-like peptide family, with the highest homology, 53%, being to GLP-1[7–36]NH$_2$ [SEQ. ID. NO. 3] (Goke, et al., *J. Biol. Chem.*, 268:19650–55, 1993). GLP-1[7–36]NH$_2$, also sometimes referred to as proglucagon[78–107] or simply "GLP-1" as used most often herein, has an insulinotropic effect, stimulating insulin secretion from pancreatic beta-cells; Glucagon-like peptide-1 (GLP-1) has also been reported to inhibit glucagon secretion from pancreatic alpha-cells (Ørsov, et al., *Diabetes*, 42:658–61, 1993; D'Alessio, et al., *J. Clin. Invest.*, 97:133–38, 1996). GLP-1 has been reported to inhibit gastric emptying (Willms B, et al., *J Clin Endocrinol Metab* 81 (1): 327–32, 1996; Wettergren A, et al., *Dig Dis Sci* 38 (4): 665–73, 1993), and gastric acid secretion (Schjoldager B T, et al., *Dig Dis Sci* 34 (5): 703–8, 1989; O'Halloran D J, et al., *J Endocrinol* 126 (1): 169–73, 1997 Wettergren A, et al., *Dig Dis Sci* 38 (4): 665–73, 1993)). GLP-1[7–37], which has an additional glycine residue at its carboxy terminus, is reported to stimulate insulin secretion in humans (Ørskov, et al., *Diabetes*, 42:658–61, 1993). A transmembrane G-protein adenylate-cyclase-coupled receptor said to be responsible at least in part for the insulinotropic effect of GLP-1 has reportedly been cloned from a beta-cell line (Thorens, *Proc. Natl. Acad. Sci. USA* 89:8641–45, 1992). GLP-1 has been the focus of significant investigation in recent years due to its reported action on the amplification of stimulated insulin production (Byrne M M, Goke B. Lessons from human studies with glucagon-like peptide-1: Potential of the gut hormone for clinical use. In: Fehmann H C, Goke B. Insulinotropic Gut Hormone Glucagon-Like Peptide 1. Basel, Switzerland: Karger, 1997:219–33).

Other reports relate to the inhibition of gastric emptying (Wettergren A, et al., Truncated GLP-1 (proglucagon 78–107-amide) inhibits gastric and pancreatic functions in man, *Dig. Dis. Sci.* 1993 April;38(4):665–73), inhibition of glucagon secretion (Creutzfeldt W O C, et al., Glucagonostatic actions and reduction of fasting hyperglycemia by exogenous glucagon-like peptide I(7–36) amide in type I diabetic patients, *Diabetes Care* 1996;19(6):580–6), and a purported role in appetite control (Turton M D, et al., A role for glucagon-like peptide-1 in the central regulation of feeding, *Nature* 1996 January;379(6560):69–72).

GLP-1 has also been reported to restore islet glucose sensitivity in aging rats, restoring their glucose tolerance to that of younger rats (Egan J M, et al., Glucagon-like peptide-1 restores acute-phase insulin release to aged rats, *Diabetologia* 1997 June;40(Suppl 1) :A130). However, the short duration of biological action of GLP-1 in vivo is one feature of the peptide that has hampered its development as a therapeutic agent. Various methods have been tried to prolong the half-life of GLP-1 or GLP-1(7–37), including attempts to alter their amino acid sequence and to deliver them using certain formulations (see, e.g., European Patent Application, entitled "Prolonged Delivery of Peptides," by Darley, et al., publication number 0 619 322 A2, regarding the inclusion of polyethylene glycol in formulations containing GLP-1 (7–37)).

Pharmacological studies have led to reports that exendin-4 can act at GLP-1 receptors on certain insulin-secreting cells, at dispersed acinar cells from guinea pig pancreas, and at parietal cells from stomach; the peptide is also reported to stimulate somatostatin release and inhibit gastrin release in isolated stomachs (Goke, et al., *J. Biol. Chem.* 268:19650–55, 1993; Schepp, et al., *Eur. J. Pharmacol.*, 69:183–91, 1994; Eissele, et al., *Life Sci.*, 55:629–34, 1994). Exendin-3 and exendin-4 were reportedly found to stimulate CAMP production in, and amylase release from, pancreatic acinar cells (Malhotra, R., et al., *Regulatory Peptides*, 41:149–56, 1992; Raufman, et al., *J. Biol. Chem.* 267:21432–37, 1992; Singh, et al., *Regul. Pept.* 53:47–59, 1994). Additionally, exendin-4 has a significantly longer duration of action than GLP-1. For example, in one experiment, glucose lowering by exendin-4 in diabetic mice was reported to persist for several hours, and, depending on dose, for up to 24 hours (Eng J. Prolonged effect of exendin-4 on hyperglycemia of db/db mice, *Diabetes* 1996 May; 45(Suppl 2):152A (abstract 554)). Based on their insulinotropic activities, the use of exendin-3 and exendin-4 for the treatment of diabetes mellitus and the prevention of hyperglycemia has been proposed (Eng, U.S. Pat. No. 5,424, 286).

The results of an investigation of whether exendins are the species homolog of mammalian GLP-1 was reported by Chen and Drucker who cloned the exendin gene from the Gila monster (J. Biol. Chem. 272(7):4108–15 (1997)). The observation that the Gila monster also has separate genes for proglucagons (from which GLP-1 is processed), that are more similar to mammalian proglucagon than exendin, indicates that exendins are not merely species homologs of GLP-1.

To date, agents that serve to delay gastric emptying have generally found a place in medicine as diagnostic aids in gastrointestinal radiological examinations. For example, glucagon is a polypeptide hormone that is produced by the alpha cells of the pancreatic islets of Langerhans. It is a hyperglycemic agent that mobilizes glucose by activating hepatic glycogenolysis. It can to a lesser extent stimulate the secretion of pancreatic insulin. Glucagon is used in the treatment of insulin-induced hypoglycemia, for example, when administration of glucose intravenously is not possible. However, as glucagon reduces the motility of the gastrointestinal tract it is also used as a diagnostic aid in gastrointestinal radiological examinations. Glucagon has also been used in several studies to treat various painful gastrointestinal disorders associated with spasm. Daniel, et al. (Br. Med. J., 3:720, 1974) reported quicker symptomatic relief of acute diverticulitis in patients treated with glucagon compared with those who had been treated with analgesics or antispasmodics. A review by Glauser, et al. (J. Am. Coll. Emergency Physns, 8:228, 1979) described relief of acute esophageal food obstruction following glucagon therapy. In another study, glucagon significantly relieved pain and tenderness in 21 patients with biliary tract disease compared with 22 patients treated with placebo (M. J. Stower, et al., Br. J. Surg., 69:591–2, 1982).

Methods for regulating gastrointestinal motility using amylin agonists are described in commonly owned International Application No. PCT/US94/10225, published Mar. 16, 1995.

Methods for regulating gastrointestinal motility using exendin agonists are described in commonly owned U.S. patent application Ser. No. 08/908,867, filed Aug. 8, 1997 entitled "Methods for Regulating Gastrointestinal Motility," which application is a continuation-in-part of U.S. patent application Ser. No. 08/694,954, filed Aug. 8, 1996.

Methods for reducing food intake using exendin agonists are described in commonly owned U.S. patent application Ser. No. 09/003,869, filed Jan. 7, 1998, entitled "Use of Exendin and Agonists Thereof for the Reduction of Food Intake," which claims the benefit of U.S. Provisional Application Nos. 60/034,905 filed Jan. 7, 1997, 60/055,404 filed Aug. 7, 1997, 60/065,442 filed Nov. 14, 1997 and 60/066, 029 filed Nov. 14, 1997.

Novel exendin agonist compounds are described in commonly owned PCT Application Ser. No. PCT/US98/16387 filed Aug. 6, 1996, entitled "Novel Exendin Agonist Compounds," which claims the benefit of U.S. Patent Application Ser. No. 60/055,404, filed Aug. 8, 1997.

Other novel exendin agonists are described in commonly owned PCT Application Serial No. PCT/US98/24210, filed Nov. 13, 1998, entitled "Novel Exendin Agonist Compounds," which claims the benefit of U.S. Provisional Application No. 60/065,442 filed Nov. 14, 1997.

Still other novel exendin agonists are described in commonly owned PCT Application Serial No. PCT/US98/24273, filed Nov. 13, 1998, entitled "Novel Exendin Agonist Compounds," which claims the benefit of U.S. Provisional Application No. 60/066,029 filed Nov. 14, 1997.

Other recent advances in exendin related technology are described in U.S. Provisional Patent Application Ser. No. 60/075,122, filed Feb. 13, 1998, entitled "Inotropic and Diuretic Effects of Exendin and GLP-1" and in U.S. Provisional Patent Application Ser. No. 60/116,380, filed Jan. 14, 1998, entitled "Novel Exendin Agonist Formulations and Methods of Administration Thereof".

Polyethylene glycol (PEG) modification of therapeutic peptides and proteins may yield both advantages and disadvantages. While PEG modification may lead to improved circulation time, reduced antigenicity and immunogenicity, improved solubility, resistance to proteolysis, improved bioavailability, reduced toxicity, improved stability, and easier formulation of peptides (See, Francis et al., International Journal of Hematology, 68:1–18, 1998) problems with PEGylation in most cases is substantial reduction in bioactivity. Id. In addition, most methods involve use of linkers that have several types of adverse effects including immunogenicity, instability, toxicity, and reactivity. Id.

Glucagonoma (tumor of glucagon-secreting cells) produces, in addition to glucose intolerance, a skin condition, necrolytic migratory erythema. This is a raised scaly red rash, sometimes blistering and eventually crusting, localized to the face, abdomen, extremities and perineum. It can also be associated with inflamation of the tongue and mouth, and diseased nails and thinning of the hair. The condition is reported to respond to octreotide, a glucagonostatic hormone analog. The compounds described herein are also useful as glucagonastatic agents and thus in the treatment of this disease, which was was first described in 1966 (Kaplan, L. M. Endocrine Tumors of the Gastrointestinal Tract and Pancreas. Ch 262, p1392: In Harrison's Principles of Internal Medicine, 12th Edition. McGraw-Hill Inc, New York, 1991). The compounds described herein that are useful for lowering glucagon levels and/or suppressing glucagon secretion include exendin, exendin agonists, and modified exendins and exendin agonists and related formulations, and dosage formulations.

The contents of the above-identified articles, patents, and patent applications, and all other documents mentioned or cited herein, are hereby incorporated by reference in their entirety. Applicants reserve the right to physically incorporate into this application any and all materials and information from any such articles, patents, patent applications, or other documents mentioned or cited herein.

SUMMARY OF THE INVENTION

The present invention relates to methods for lowering glucagon levels and/or suppressing glucagon secretion in a subject. It also relates to the treatment of hyperglucgonemia and conditions that benefit from. administration of glucagonostatic agents, including but not limited to necrolytic migratory erythema.

Thus, in one aspect, the invention relates to the use of an exendin, an exendin agonist, or a modified exendin or exendin agonist having an exendin or exendin agonist linked to one or more polyethylene glycol polymers, or other molecular weight enhancing molecules, for lowering glucagon levels in a subject.

In another aspect, the invention relates to the use of an exendin, an exendin agonist, or a modified exendin or exendin agonist having an exendin or exendin agonist linked to one or more polyethylene glycol polymers or other compounds useful to decrease renal clearance of the parent peptide, for suppressing glucagon secretion in a subject.

In still another aspect, the invention relates to the use of an exendin, an exendin agonist, or a modified exendin or exendin agonist having an exendin or exendin agonist linked to one or more polyethylene glycol polymers, or other molecular weight enhancing molecules, for treating conditions associated with hyperglucagonemia.

In yet another aspect, the invention relates to the use of an exendin, an exendin agonist, or a modified exendin or exendin agonist having an exendin or exendin agonist linked to one or more polyethylene glycol polymers, or other molecular weight enhancing molecules, for treating a subject with a glucagonoma or necrolytic migratory erythema.

In preferred embodiments, the exendin is exendin-4. In other preferred embodiments, the modified exendin or exendin agonist has a molecular weight that is greater than the molecular weight of the exendin or exendin agonist (preferably about 10%, 50% or 90% greater), the modified exendin or exendin agonist has a negative charge that is greater than the negative charge of the exendin or exendin agonist (preferably about 10%, 50% or 90% greater), the modified exendin or exendin agonist has a kidney clearance that is less than the kidney clearance of the exendin or exendin agonist (preferably about lot, 50% or 90% less), the modified exendin or exendin agonist has a half-life that is greater than the half-life of the exendin or exendin agonist (preferably about 10%, 50% or 90% greater), the modified exendin or exendin agonist has a immunogenicity/antigenicity that is less than the immunogenicity/antigenicity of the exendin or exendin agonist, the modified exendin or exendin agonist has a solubility that is greater than the solubility of the exendin or exendin agonist (preferably about 10%, 50% or 90% greater), the modified exendin or exendin agonist has a proteolysis rate that is less than the proteolysis rate of the exendin or exendin agonist (preferably about 10%, 50% or 90% less), the modified exendin or exendin agonist has a toxicity that is less than the toxicity of the exendin or themodified exendin agonist, the modified exendin or exendin agonist has a stability that is greater than the stability of the exendin or exendin agonist, and the modified exendin or exendin agonist has a permeability/biological function that is greater or less than the permeability/biological function of the exendin or exendin agonist (preferably about 10%, 50% or 90% greater or less)

The exendin or exendin agonist may be linked to one, two or three polyethylene glycol polymers. The polyethylene glycol polymers may preferably have molecular weights between 500 and 20,000. In a preferred embodiment, the modified exendin or exendin agonist is one of compounds 201–217, more preferably one of compounds 209, 210 and 213, or one of compounds 201 and 202, or one of compounds 216 and 217 (See Example 4 below).

The polyethylene glycol polymers are preferably linked to an amino, carboxyl, or thio group, and may be linked by N or C termini of side chains of lysine, aspartic acid, glutamic acid, or cysteine, or alternatively, the polyethylene glycol polymers may be linked with diamine and dicarboxylic groups. The exendin or exendin agonist is preferably linked to the polyethylene glycol polymers through an epsilon amino group on a lysine amino acid of the exendin or exendin agonist.

By "exendin agonist" is meant a compound which mimics the effects of exendins, e.g., on gastric motility and gastric emptying (namely, a compound which effectively binds to the receptor at which exendins exert their action on gastric motility and gastric emptying, preferably an analog or derivative of an exendin) or a compound, e.g., that mimics the effects of exendin on the reduction of food intake by binding to the receptor or receptors where exendin causes this effect. Preferred exendin agonist compounds include those described in U.S. patent application Ser. No. 90/003,869, entitled, "Use of Exendin And Agonists Thereof For The Reduction of Food Intake", filed Jan. 7, 1998, (and the priority applications thereto) which enjoys common ownership with the present application and which is incorporated by this reference into the present application as though fully set forth herein. Effects of exendins or exendin agonists can be identified, evaluated, or screened for, using the methods described herein, or other methods known in the art for determining exendin effects.

In another aspect, a therapeutically effective amount of an amylin agonist is also administered to the subject. In a preferred aspect, the amylin agonist is an amylin or an amylin agonist analog such as $^{25,28,29}$Pro-human-amylin. (also known as "pramlintide," and previously referred to as "AC-137" and described in "Amylin Agonist Peptides and Uses Therefor," U.S. Pat. No. 5,686,511, issued Nov. 11, 1997), or salmon calcitonin.

Preferably, the subject is a vertebrate, more preferably a mammal, and most preferably a human. In preferred aspects, the exendin, exendin agonist, or modified exendin or exendin agonist of the invention is administered parenterally, more preferably by injection. In a most preferred aspect, the injection is a peripheral injection. Preferably, about 1 µg–30 µg to about 5 mg of the modified exendin or exendin agonist of the invention is administered per day. More preferably, about 1–30 µg to about 2 mg, or about 1–30 µg to about 1 mg of the modified exendin or exendin agonist of the invention is administered per day. Most preferably, about 3 µg to about 500 µg of the modified exendin or exendin agonist of the invention is administered per day.

Preferred exendins or exendin agonists for modification and use include:

exendin-4 (1–30) [SEQ ID NO: 4: His Gly Glu Gly Thr Phe Thr Ser Asp Leu Ser Lys Gln Met Glu Glu Glu Ala Val Arg Leu Phe Ile Glu Trp Leu Lys Asn Gly Gly-];

exendin-4 (1–30) amide [SEQ ID NO: 5: His Gly Glu Gly Thr Phe Thr Ser Asp Leu Ser Lys Gln Met Glu Glu Glu Ala Val Arg Leu Phe Ile Glu Trp Leu Lys Asn Gly Gly-NH$_2$];

exendin-4 (1–28) amide [SEQ ID NO: 6: His Gly Glu Gly Thr Phe Thr Ser Asp Leu Ser Lys Gln Met Glu Glu Glu Ala Val Arg Leu Phe Ile Glu Trp Leu Lys Asn-NH$_2$];

$^{14}$Leu,$^{25}$Phe exendin-4 amide [SEQ ID NO: 7: His Gly Glu Gly Thr Phe Thr Ser Asp Leu Ser Lys Gln Leu Glu Glu Glu Ala Val Arg Leu Phe Ile Glu Phe Leu Lys Asn Gly Gly Pro Ser Ser Gly Ala Pro Pro Pro Ser-NH$_2$];

$^{14}$Leu,$^{25}$Phe exendin-4 (1–28) amide [SEQ ID NO: 8: His Gly Glu Gly Thr Phe Thr Ser Asp Leu Ser Lys Gln Leu Glu Glu Glu Ala Val Arg Leu Phe Ile Glu Phe Leu Lys Asn-NH$_2$]; and $^{14}$Leu,$^{22}$Ala,$^{25}$Phe exendin-4 (1–28) amide [SEQ ID NO: 9: His Gly Glu Gly Thr Phe Thr Ser Asp Leu Ser Lys Gln Leu Glu Glu Glu Ala Val Arg Leu Ala Ile Glu Phe Leu Lys Asn-NH$_2$].

Definitions

In accordance with the present invention and as used herein, the following terms are defined to have the following meanings, unless explicitly stated otherwise.

The term "amino acid" refers to natural amino acids, unnatural amino acids, and amino acid analogs, all in their D and L stereoisomers if their structure allow such stereoisomeric forms. Natural amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), Lysine (Lys), methionine (Met), phenylalanine (Phe), proline (Pro), serine (Ser), threonine (Thr), typtophan (Trp), tyrosine (Tyr) and valine (Val). Unnatural amino acids include, but are not limited to azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, tertiary-butylglycine, 2,4-diaminoisobutyric acid, desmosine, 2,2'-diaminopimelic acid, 2,3-diaminopropionic acid, N-ethylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, norleucine, ornithine, pentylglycine, pipecolic acid and thioproline. Amino acid analogs include the natural and unnatural amino acids which are chemically blocked, reversibly or irreversibly, or modified on their N-terminal amino group or their side-chain groups, as for example, methionine sulfoxide, methionine sulfone, S-(carboxymethyl)-cysteine, S-(carboxymethyl)-cysteine sulfoxide and S-(carboxymethyl)-cysteine sulfone.

The term "amino acid analog" refers to an amino acid wherein either the C-terminal carboxy group, the N-terminal amino group or side-chain functional group has been chemically codified to another functional group. For example, aspartic acid-(beta-methyl ester) is an amino acid analog of aspartic acid; N-ethylglycine is an amino acid analog of glycine; or alanine carboxamide is an amino acid analog of alanine.

The term "amino acid residue" refers to radicals having the structure: (1) —C(O)—R—NH—, wherein R typically is —CH(R')—, wherein R' is an amino acid side chain, typically H or a carbon containing substitutent; or (2)

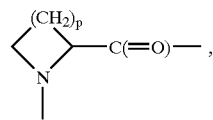

wherein p is 1, 2 or 3 representing the azetidinecarboxylic acid, proline or pipecolic acid residues, respectively.

The term "lower" referred to herein in connection with organic radicals such as alkyl groups defines such groups with up to and including about 6, preferably up to and including 4 and advantageously one or two carbon atoms. Such groups may be straight chain or branched chain.

"Pharmaceutically acceptable salt" includes salts of the compounds of the present invention derived from the combination of such compounds and an organic or inorganic acid. In practice the use of the salt form amounts to use of the base form. The compounds of the present invention are useful in both free base and salt form, with both forms being considered as being within the scope of the present invention.

In addition, the following abbreviations stand for the following:
"ACN" or "CH₃CN" refers to acetonitrile.
"Boc", "tBoc" or "Tboc" refers to t-butoxy carbonyl.
"DCC" refers to N,N'-dicyclohexylcarbodiimide.

"Fmoc" refers to fluorenylmethoxycarbonyl.
"HBTU" refers to 2-(1H-benzotriazol-1-yl)-1,1,3,3,-tetramethyluronium hexaflurophosphate.
"HOBt" refers to 1-hydroxybenzotriazole monohydrate.
"homoP" or hPro" refers to homoproline.
"MeAla" or "Nme" refers to N-methylalanine.
"naph" refers to naphthylalanine.
"pG" or pGly "" refers to pentylglycine.
"tBuG" refers to tertiary-butylglycine.
"ThioP" or tPro" refers to thioproline.
"3Hyp" refers to 3-hydroxyproline
"4Hyp" refers to 4-hydroxyproline
"NAG" refers to N-alkylglycine
"NAPG" refers to N-alkylpentylglycine
"Norval" refers to norvaline
"Norleu" refers to norleucine Other features and advantages of the invention will be apparent from the following description of the preferred embodiments thereof, and from the claims.

BRIEF DESCRIPTION OF THE DRAWINGS

FIG. 1 depicts the amino acid sequence for exendin-3 [SEQ. ID. NO. 1].

FIG. 2 depicts the amino acid sequence for exendin-4 [SEQ. ID. NO. 2].

FIGS. 3A 3A and 3B depict the amino acid sequences for certain exendin agonist compounds useful in the present invention [SEQ. ID. NOS. 10 to 40].

FIGS. 4A1–4J depict the amino acid sequences for certain compounds of the present invention, Compounds 1–174 [SEQ. ID. NOS. 49to 22].

DETAILED DESCRIPTION OF THE INVENTION

Figure 5:
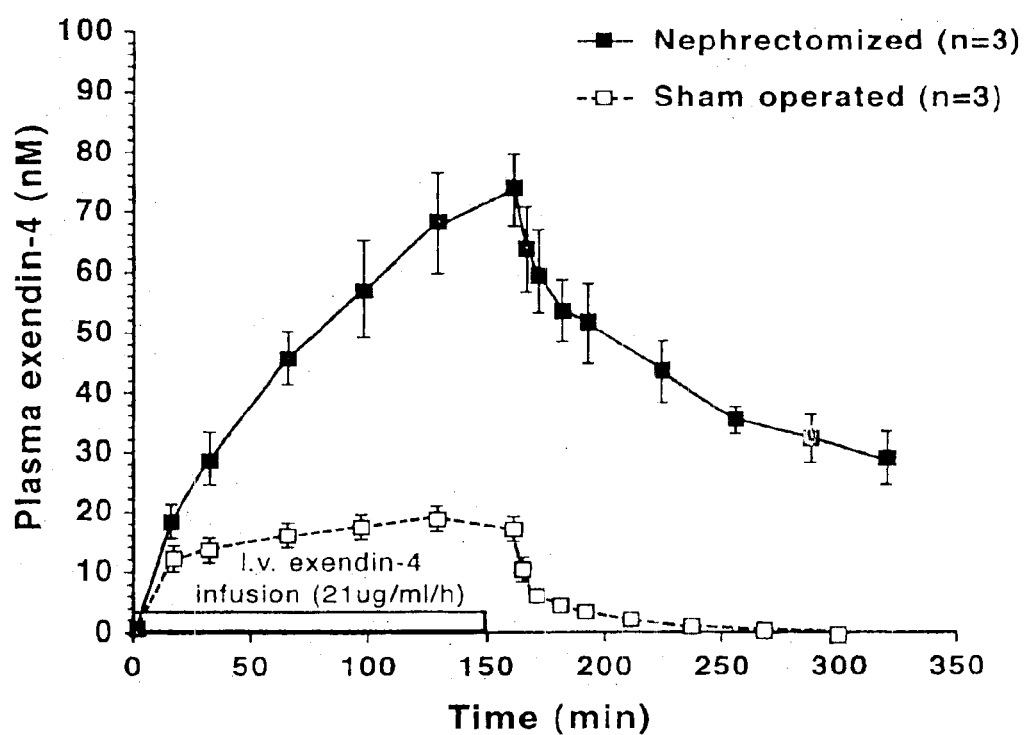
FIG. 5 is a graph showing the effect of functional nephrectomy on exendin-4 clearance.

The present invention relates to relates to methods of suppressing and/or lowering glucagon in a subject, comprising the administration of an exendin, an exendin agonist, or a modified exendin or exendin agonist having an exendin or exendin agonist peptide linked to one or more polyethylene glycol polymers or other compound useful to increase molecular weight. Such methods are useful, for example, in the treatment of hyperglucagonemia and other conditions in which lower levels of glucagon or suppresion of glucagon secretion are of benefit. Such conditions include, but are not limited to, glucagonoma and necrolytic migratory erythema.

Modified Exendins and Exendin Agonists

The modified exendins and exendin agonists of the present invention include, for example, one or more PEG polymers linked to an exendin or exendin agonist, such as a naturally occurring exendin, a synthetic exendin or an exendin agonist.

Exendin-4

Exendin-4 is a naturally occurring peptide isolated from the salivary secretions of the Gila monster. Animal testing of exendin-4 has shown that its ability to lower blood glucose persists for several hours. Exendin-4, a 39-amino acid polypeptide, is synthesized using solid phase synthesis as described herein, and this synthetic material has been shown to be identical to that of native exendin-4.

As described herein, the nonclinical pharmacology of exendin-4 has been studied. In the brain, exendin-4 binds principally to the area postrema and nucleus tractus solitarius region in the hindbrain and to the subfornical organ in the forebrain. Exendin-4 binding has been observed in the rat and mouse brain and kidney. The structures to which exendin-4 binds in the kidney are unknown.

Various experiments have compared the biologic actions of exendin-4 and GLP-1 and demonstrated a more favorable spectrum of properties for exendin-4. A single subcutaneous dose of exendin-4 lowered plasma glucose in db/db (diabetic) and ob/ob (diabetic obese) mice by up to 40%. In Diabetic Fatty Zucker (ZDF) rats, 5 weeks of treatment with exendin-4 lowered $RbA_{1c}$ (a measure of glycosylated hemoglobin used to evaluate plasma glucose levels) by up to 41%. Insulin sensitivity was also improved by 76% following 5 weeks of treatment in obese ZDF rats. In glucose intolerant primates, dose-dependent decreases in plasma glucose were also observed.

An insulinotropic action of exendin-4 has also been observed in rodents, improving insulin response to glucose by over 100% in non-fasted Harlan Sprague Dawley (HSD) rats, and by up to −10-fold in non-fasted db/db mice. Higher pretreatment plasma glucose concentrations were associated with greater glucose-lowering effects. Thus the observed glucose lowering effect of exendin-4 appears to be glucose-dependent, and minimal if animals are already euglycemic.

Exendin-4 dose dependently slowed gastric emptying in HSD rats and was -90-fold more potent than GLP-1 for this action. Exendin-4 has also been shown to reduce food intake in NIH/Sw (Swiss) mice following peripheral administration, and was at least 1000 times more potent than GLP-1 for this action. Exendin-4 reduced plasma glucagon concentrations by approximately 40% in anesthetized ZDF rats during hyperinsulinemic, hyperglycemic clamp conditions, but did not affect plasma glucagon concentrations during euglycemic conditions in normal rats. Exendin-4 has been shown to dose-dependently reduce body weight in obese ZDF rats, while in lean ZDF rats, the observed decrease in body weight appears to be transient.

Through effects on lowering glucagon and supressing glucagon secretion, exendins, exendin agonists, and modified exendins or exendin agonists containing exendin-4, for example, will be useful in people who would benefit from lowered glucagon, for example, people with glucagonoma and necrolytic migratory erythema, and people with diabetes whether or not they retain the ability to secrete insulin. See Example 5.

The toxicology of exendin-4 has been investigated in single-dose studies in mice, rats and monkeys, repeated-dose (up to 28 consecutive daily doses) studies in rats and monkeys and in vitro tests for mutagenicity and chromosomal alterations. To date, no deaths have occurred, and there have been no observed treatment-related changes in hematology, clinical chemistry, or gross or microscopic tissue changes. Exendin-4 was demonstrated to be non-mutagenic, and did not cause chromosomal aberrations at the concentrations tested (up to 5000 µg/mL).

In support of the investigation of the nonclinical pharmacokinetics and metabolism of exendin-4, a number of immunoassays have been developed. A radioimmunoassay with limited sensitivity (~100 pM) was used in initial pharmacokinetic studies. A two-site immunoradiometric assay (IRMA) for exendin-4 was subsequently validated with a lower limit of quantitation of 15 pM. The bioavailability of exendin-4, given subcutaneously, was found to be approximately 50–80% using the radioimmunoassay. This was similar to that seen following intraperitoneal administration (48–60%). Peak plasma concentrations ($C_{max}$) occurred between 30 and 43 minutes ($T_{max}$). Both $C_{max}$ and area under curve (AUC) values were monotonically related to dose. The apparent terminal half-life for exendin-4 given subcutaneously was approximately 90–110 minutes. This was significantly longer than the 14–41 minutes seen following intravenous dosing. Similar results were obtained using the IRMA. Degradation studies with exendin-4 compared to GLP-1 indicate that exendin-4 is relatively resistant to degradation.

Exendin Agonists

The structure activity relationship (SAR) of exendin was investigated for structures that may relate to the antidiabetic activity of exendin, for its stability to metabolism, and for improvement of its physical characteristics, especially as it pertains to peptide stability and to amenability to alternative delivery systems, and various exendin agonist peptide compounds have been invented. Exendin agonists include exendin peptide analogs in which one or more naturally occurring amino acids are eliminated or replaced with another amino acid(s) Preferred exendin agonists are agonist analogs of exendin-4. Particularly preferred exendin agonists include those described in commonly owned PCT Application Serial No. PCT/US98/16387 filed Aug. 6, 1998, entitled "Novel Exendin Agonist Compounds," which claims the benefit of U.S. patent application Ser. No. 60/055,404, filed Aug. 8, 1997; commonly owned PCT Application Serial No. PCT/US98/24210, filed Nov. 13, 1998, entitled "Novel Exendin Agonist Compounds," which claims the benefit of U.S. Provisional Application No. 60/065,442 filed Nov. 14, 1997; and, commonly owned PCT Application Serial No. PCT/US98/24273, filed Nov. 13, 1998, entitled "Novel Exendin Agonist Compounds," which claims the benefit of U.S. Provisional Application No. 60/066,029 filed Nov. 14, 1997, all of which are incorporated herein by reference in their entirety, including any drawings.

Activity as exendin agonists can be indicated, for example, by activity in the assays described below. Effects of exendins or exendin agonists on gastric motility and gastric emptying can be identified, evaluated, or screened for, using the methods described herein, or other art-known or equivalent methods for determining gastric motility. Negative receptor assays or screens for exendin agonist compounds or candidate exendin agonist compounds, such as an amylin receptor assay/screen using an amylin receptor preparation as described in U.S. Pat. No. 5,264,372, issued Nov. 23, 1993, the contents of which are incorporated herein by reference, one or more calcitonin receptor assays/screens using, for example, T47D and MCF7 breast carcinoma cells, which contain calcium receptors coupled to the stimulation of adenyl cyclase activity, and/or a CGRP receptor assay/screen using, for example, SK-N-MC cells.

One such method for use in identifying or evaluating the ability of a compound to slow gastric motility, involves: (a) bringing together a test sample and a test system, the test sample containing one or more test compounds, the test system containing a system for evaluating gastric motility, the system being characterized in that it exhibits, for example, elevated plasma glucose in response to the introduction to the system of glucose or a meal; and, (b) determining the presence or amount of a rise in plasma glucose in the system. Positive and/or negative controls may be used as well.

Also included within the scope of the present invention are pharmaceutically acceptable salts of the compounds of formula (I–VIII) and pharmaceutical compositions including said compounds and salts thereof.

Formula I

Exendin agonist compounds also include those described in U.S. Provisional Application No. 60/065,442, including compounds of the formula (I) [SEQ ID NO: 41]:

$Xaa_1$ $Xaa_2$ $Xaa_3$ Gly $Xaa_5$ $Xaa_6$ $Xaa_7$ $Xaa_8$ $Xaa_9$ $Xaa_{10}$ $Xaa_{11}$ $Xaa_{12}$ $Xaa_{13}$ $Xaa_{14}$ $Xaa_{15}$ $Xaa_{16}$ $Xaa_{17}$ Ala $Xaa_{19}$ $Xaa_{20}$ $Xaa_{21}$ $Xaa_{22}$ $Xaa_{23}$ $Xaa_{24}$ $Xaa_{25}$ $Xaa_{26}$ $Xaa_{27}$ $Xaa_{28}$-$Z_1$; wherein $Xaa_1$ is His, Arg or Tyr;
$Xaa_2$ is Ser, Gly, Ala or Thr;
$Xaa_3$ is Asp or Glu;
$Xaa_5$ is Ala or Thr;
$Xaa_6$ is Ala, Phe, Tyr or naphthylalanine;
$Xaa_7$ is Thr or Ser;
$Xaa_8$ is Ala, Ser or Thr;
$Xaa_9$ is Asp or Glu;
$Xaa_{10}$ is Ala, Leu, Ile, Val, pentylglycine or Met;
$Xaa_{11}$ is Ala or Ser;
$Xaa_{12}$ is Ala or Lys;
$Xaa_{13}$ is Ala or Gln;
$Xaa_{14}$ is Ala, Leu, Ile, pentylglycine, Val or Met;
$Xaa_{15}$ is Ala or Glu;
$Xaa_{16}$ is Ala or Glu;
$Xaa_{17}$ is Ala or Glu;
$Xaa_{19}$ is Ala or Val;
$Xaa_{20}$ is Ala or Arg;
$Xaa_{21}$ is Ala or Leu;
$Xaa_{22}$ is Ala, Phe, Tyr or naphthylalanine;
$Xaa_{23}$ is Ile, Val, Leu, pentylglycine, tert-butylglycine or Met;
$Xaa_{24}$ is Ala, Glu or Asp;
$Xaa_{25}$ is Ala, Trp, Phe, Tyr or naphthylalanine;
$Xaa_{26}$ is Ala or Leu;
$Xaa_{27}$ is Ala or Lys;
$Xaa_{28}$ is Ala or Asn;
$Z_1$ is —OH,
—$NH_2$
Gly-$Z_2$,
Gly Gly-$Z_2$,
Gly Gly $Xaa_{31}$-$Z_2$,
Gly Gly $Xaa_{31}$ Ser-$Z_2$,
Gly Gly $Xaa_{31}$ Ser Ser-$Z_2$,
Gly Gly $Xaa_{31}$ Ser Ser Gly-$Z_2$,
Gly Gly $Xaa_{31}$ Ser Ser Gly Ala-$Z_2$,
Gly Gly $Xaa_{31}$ Ser Ser Gly Ala $Xaa_{36}$ -$Z_2$,
Gly Gly $Xaa_{31}$ Ser Ser Gly Ala $Xaa_{36}$ $Xaa_{37}$-$Z_2$ or
Gly Gly $Xaa_{31}$ Ser Ser Gly Ala $Xaa_{36}$ $XaaXaa_{38}$-$Z_2$;
$Xaa_{31}$, $Xaa_{36}$, $Xaa_{37}$ and $Xaa_{38}$ are independently Pro, homoproline, 3Hyp, 4Hyp, thioproline,
N-alkylglycine, N-alkylpentylglycine or
N-alkylalanine; and
$Z_2$ is —OH or —$NH_2$;
provided that no more than three of $Xaa_3$, $Xaa_5$, $Xaa_6$, $Xaa_8$, $Xaa_{10}$, $Xaa_{11}$, $Xaa_{12}$, $Xaa_{13}$, $Xaa_{14}$, $Xaa_{15}$, $Xaa_{16}$, $Xaa_{17}$, $Xaa_{19}$, $Xaa_{20}$, $Xaa_{21}$, $Xaa_{24}$, $Xaa_{25}$, $Xaa_{26}$, $Xaa_{27}$ and $Xaa_{28}$ are Ala.

Preferred N-alkyl groups for N-alkylglycine, N-alkylpentylglycine and N-alkylalanine include lower alkyl groups preferably of 1 to about 6 carbon atoms, more preferably of 1 to 4 carbon atoms.

Preferred exendin agonist compounds include those wherein $Xaa_1$ is His or Tyr. More preferably $Xaa_1$ is His.

Preferred are those compounds wherein $Xaa_2$ is Gly.

Preferred are those compounds wherein $Xaa_{14}$ is Leu, pentylglycine or Met.

Preferred compounds are those wherein $Xaa_{25}$ is Trp or Phe.

Preferred compounds are those where $Xaa_6$ is Phe or naphthylalanine; $Xaa_{22}$ is Phe or naphthylalanine and $Xaa_{23}$ is Ile or Val.

Preferred are compounds wherein $Xaa_{31}$, $Xaa_{36}$, $Xaa_{37}$ and $Xaa_{38}$ are independently selected from Pro, homoproline, thioproline and N-alkylalanine.

Preferably $Z_1$ is —$NH_2$.
Preferably $Z_2$ is —$NH_2$.

According to one aspect, preferred are compounds of formula (I) wherein $Xaa_1$ is His or Tyr, more preferably His; $Xaa_2$ is Gly; $Xaa_6$ is Phe or naphthylalanine; $Xaa_{14}$ is Leu, pentylglycine or Met; $Xaa_{22}$ is Phe or naphthylalanine; $Xaa_{23}$ is Ile or Val; $Xaa_{31}$, $Xaa_{36}$, $Xaa_{37}$ and $Xaa_{38}$ are independently selected from Pro, homoproline, thioproline or N-alkylalanine. More preferably $Z_1$ is —$NH_2$.

According to an especially preferred aspect, especially preferred compounds include those of formula (I) wherein: $Xaa_1$ is His or Arg; $Xaa_2$ is Gly or Ala; $Xaa_3$ is Asp or Glu; $Xaa_5$ is Ala or Thr; $Xaa_6$ is Ala, Phe or naphthylalanine; $Xaa_7$ is Thr or Ser; $Xaa_8$ is Ala, Ser or Thr; $Xaa_9$ is Asp or Glu; $Xaa_{10}$ is Ala, Leu or pentylglycine; $Xaa_{11}$ is Ala or Ser; $Xaa_{12}$ is Ala or Lys; $Xaa_{13}$ is Ala or Gln; $Xaa_{14}$ is Ala, Leu or pentylglycine; $Xaa_{15}$ is Ala or Glu; $Xaa_{16}$ is Ala or Glu; $Xaa_{17}$ is Ala or Glu; $Xaa_{19}$ is Ala or Val; $Xaa_{20}$ is Ala or Arg; $Xaa_{21}$ is Ala or Leu; $Xaa_{22}$ is Phe or naphthylalanine; $Xaa_{23}$ is Ile, Val or tert-butylglycine; $Xaa_{24}$ is Ala, Glu or Asp; $Xaa_{25}$ is Ala, Trp or Phe; $Xaa_{26}$ is Ala or Leu; $Xaa_{27}$ is Ala or Lys; $Xaa_{28}$ is Ala or Asn; $Z_1$ is —OH, —$NH_2$, Gly-$Z_2$, Gly Gly-$Z_2$, Gly Gly $Xaa_{31}$-$Z_2$, Gly Gly $Xaa_{31}$ Ser-$Z_2$, Gly Gly $Xaa_{31}$ Ser Ser-$Z_2$, Gly Gly $Xaa_{31}$ Ser Ser Gly-$Z_2$, Gly Gly $Xaa_{31}$ Ser Ser Gly Ala-$Z_2$, Gly Gly $Xaa_{31}$ Ser Ser Gly Ala $Xaa_{36}$-$Z_2$, Gly Gly $Xaa_{31}$ Ser Ser Gly Ala $Xaa_{36}$ $Xaa_{37}$-$Z_2$, Gly Gly $Xaa_{31}$ Ser Ser Gly Ala $Xaa_{36}$ $Xaa_{37}$-$Z_2$; $Xaa_{31}$, $Xaa_{36}$, $Xaa_{37}$ and $Xaa_{38}$ being independently Pro homoproline, thioproline or N-methylalanine; and $Z_2$ being —OH or —$NH_2$; provided that no more than three of $Xaa_3$, $Xaa_5$, $Xaa_6$, $Xaa_8$, $Xaa_{10}$, $Xaa_{11}$, $Xaa_{12}$, $Xaa_{13}$, $Xaa_{14}$, $Xaa_{15}$, $Xaa_{16}$, $Xaa_{17}$, $Xaa_{19}$, $Xaa_{20}$, $Xaa_{21}$, $Xaa_{24}$, $Xaa_{25}$, $Xaa_{26}$, $Xaa_{27}$ and $Xaa_{28}$ are Ala. Especially preferred compounds include those set forth in PCT application Serial No. PCT/US98/24210, filed Nov. 13, 1998, entitled "Novel Exendin Agonist Compounds" identified therein as compounds 2–23.

According to an especially preferred aspect, provided are compounds where $Xaa_{14}$ is Leu, Ile, Val or pentylglycine, more preferably Leu or pentylglycine, and $Xaa_{25}$ is Phe, Tyr or naphthylalanine, more preferably Phe or naphthylalanine. These compounds will be less susceptive to oxidative. degration, both in vitro and in vivo, as well as during synthesis of the compound.

Formula II

Exendin agonist compounds also include those described in U.S. Provisional Application No. 60/066,029, including compounds of the formula (II)[SEQ ID NO: 42]:

$Xaa_1$ $Xaa_2$ $Xaa_3$ $Xaa_4$ $Xaa_5$ $Xaa_6$ $Xaa_7$ $Xaa_8$ $Xaa_9$ $Xaa_{10}$ $Xaa_{11}$ $Xaa_{12}$ $Xaa_{13}$ $Xaa_{14}$ $Xaa_{15}$ $Xaa_{16}$ $Xaa_{17}$ Ala $Xaa_{19}$ $Xaa_{20}$ $Xaa_{21}$ $Xaa_{22}$ $Xaa_{23}$ $Xaa_{24}$ $Xaa_{25}$ $Xaa_{26}$ $Xaa_{27}$ $Xaa_{28}$-$Z_1$; wherein
$Xaa_1$ is His, Arg, Tyr, Ala, Norval, Val or Norleu;
$Xaa_2$ is Ser, Gly, Ala or Thr;
$Xaa_3$ is Ala, Asp or Glu;
$Xaa_4$ is Ala, Norval, Val, Norleu or Gly;
$Xaa_5$ is Ala or Thr;
$Xaa_6$ is Phe, Tyr or naphthylalanine;
$Xaa_7$ is Thr or Ser;
$Xaa_8$ is Ala, Ser or Thr;
$Xaa_9$ is Ala, Norval, Val, Norleu, Asp or Glu;
$Xaa_{10}$ is Ala, Leu, Ile, Val, pentylglycine or Met;
$Xaa_{11}$ is Ala or Ser;
$Xaa_{12}$ is Ala or Lys;
$Xaa_{13}$ is Ala or Gln;
$Xaa_{14}$ is Ala, Leu, Ile, pentylglycine, Val or Met;

$Xaa_{15}$ is Ala or Glu;
$Xaa_{16}$ is Ala or Glu;
$Xaa_{17}$ is Ala or Glu;
$Xaa_{19}$ is Ala or Val;
$Xaa_{20}$ is Ala or Arg;
$Xaa_{21}$ is Ala or Leu;
$Xaa_{22}$ is Phe, Tyr or naphthylalanine;
$Xaa_{23}$ is Ile, Val, Leu, pentylglycine, tert-butylglycine or Met;
$Xaa_{24}$ is Ala, Glu or Asp;
$Xaa_{25}$ is Ala, Trp, Phe, Tyr or naphthylalanine;
$Xaa_{26}$ is Ala or Leu;
$Xaa_{27}$ is Ala or Lys;
$Xaa_{28}$ is Ala or Asn;
$Z_1$ is —OH,
 —$NH_2$,
 Gly-$Z_2$,
 Gly Gly-$Z_2$,
 Gly Gly $Xaa_{31}$-$Z_2$,
 Gly Gly $Xaa_{31}$ Ser-$Z_2$,
 Gly Gly $Xaa_{31}$ Ser Ser-$Z_2$,
 Gly Gly $Xaa_{31}$ Ser Ser Gly-$Z_2$,
 Gly Gly $Xaa_{31}$ Ser Ser Gly Ala-$Z_2$,
 Gly Gly $Xaa_{31}$ Ser Ser Gly Ala $Xaa_{36}$-$Z_2$,
 Gly Gly $Xaa_{31}$ Ser Ser Gly Ala $Xaa_{36}$ $Xaa_{37}$-$Z_2$,
 Gly Gly $Xaa_{31}$ Ser Ser Gly Ala $Xaa_{36}$ $Xaa_{37}$ $Xaa_{38}$-$Z_2$ or
 Gly Gly $Xaa_{31}$ Ser Ser Gly Ala $Xaa_{36}$ $Xaa_{37}$ $Xaa_{38}$ $Xaa_{39}$-$Z_2$;
wherein
$Xaa_{31}$, $Xaa_{36}$, $Xaa_{37}$ and $Xaa_{38}$ are independently Pro, homoproline, 3Hyp, 4Hyp, thioproline,
 N-alkylglycine, N-alkylpentylglycine or
 N-alkylalanine; and
 $Z_2$ is —OH or —$NH_2$;
provided that no more than three of $Xaa_3$, $Xaa_4$, $Xaa_5$, $Xaa_6$, $Xaa_8$, $Xaa_9$, $Xaa_{10}$, $Xaa_{11}$, $Xaa_{12}$, $Xaa_{13}$, $Xaa_{14}$, $Xaa_{15}$, $Xaa_{16}$, $Xaa_{17}$, $Xaa_{19}$, $Xaa_{20}$, $Xaa_{21}$, $Xaa_{24}$, $Xaa_{25}$, $Xaa_{26}$, $Xaa_{27}$ and $Xaa_{28}$ are Ala; and provided also that, if $Xaa_1$ is His, Arg or Tyr, then at least one of $Xaa_3$, $Xaa_4$ and $Xaa_9$, is Ala.

Preferred N-alkyl groups for N-alkylglycine, N-alkylpentylglycine and N-alkylalanine include lower alkyl groups preferably of 1 to about 6 carbon atoms, more preferably of 1 to 4 carbon atoms. Suitable compounds of formula (II) include those described in application Serial No. PCT/US98/24273, filed Nov. 13, 1998, entitled "Novel Exendin Agonist Compounds", identified therein in Examples 1–89 ("Compounds 1–89," respectively), as well as those corresponding compounds identified therein in Examples 104 and 105.

Preferred such exendin agonist compounds include those wherein $Xaa_1$ is His, Ala or Norval. More preferably $Xaa_1$ is His or Ala. Most preferably $Xaa_1$ is His.

Preferred are those compounds of formula (II) wherein $Xaa_2$ is Gly.

Preferred are those compounds of formula (II) wherein $Xaa_3$ is Ala.

Preferred are those compounds of formula (II) wherein $Xaa_4$ is Ala.

Preferred are those compounds of formula (II) wherein $Xaa_9$ is Ala.

Preferred are those compounds of formula (II) wherein $Xaa_{14}$ is Leu, pentylglycine or Met.

Preferred compounds of formula (II) are those wherein $Xaa_{25}$ is Trp or Phe.

Preferred compounds of formula (II) are those where $Xaa_6$ is Ala, Phe or naphthylalanine; $Xaa_{22}$ is Phe or naphthylalanine; and $Xaa_{23}$ is Ile or Val.

Preferred are compounds of formula (II) wherein $Xaa_{31}$, $Xaa_{36}$, $Xaa_{37}$ and $Xaa_{38}$ are independently selected from Pro, homoproline, thioproline and N-alkylalanine.

Preferably $Z_1$ is —$NH_2$.

Preferably $Z_2$ is —$NH_2$.

According to one aspect, preferred are compounds of formula (II) wherein $Xaa_1$ is Ala, His or Tyr, more preferably Ala or His; $Xaa_2$ is Ala or Gly; $Xaa_6$ is Phe or naphthylalanine; $Xaa_{14}$ is Ala, Leu, pentylglycine or Met; $Xaa_{22}$ is Phe or naphthylalanine; $Xaa_{23}$ is Ile or Val; $Xaa_{31}$, $Xaa_{36}$ $Xaa_{37}$ and $Xaa_{38}$ are independently selected from Pro, homoproline, thioproline or N-alkylalanine; and $Xaa_{39}$ is Ser or Tyr, more preferably Ser. More preferably $Z_1$ is —$NH_2$.

According to an especially preferred aspect, especially preferred compounds include those of formula (II) wherein: $Xaa_1$ is His or Ala; $Xaa_2$ is Gly or Ala; $Xaa_3$ is Ala, Asp or Glu; $Xaa_4$ is Ala or Gly; $Xaa_5$ is Ala or Thr; $Xaa_6$ is Phe or naphthylalanine; $Xaa_7$ is Thr or Ser; $Xaa_8$ is Ala, Ser or Thr; $Xaa_9$ is Ala, Asp or Glu; $Xaa_{10}$ is Ala, Leu or pentylglycine; $Xaa_{11}$ is Ala or Ser; $Xaa_{12}$ is Ala or Lys; $Xaa_{13}$ is Ala or Gln; $Xaa_{14}$ is Ala, Leu, Met or pentylglycine; $Xaa_{15}$ is Ala or Glu; $Xaa_{16}$ is Ala or Glu; $Xaa_{17}$ is Ala or Glu; $Xaa_{19}$ is Ala or Val; $Xaa_{20}$ is Ala or Arg; $Xaa_{21}$ is Ala or Leu; $Xaa_{22}$ is Phe or naphthylalanine; $Xaa_{23}$ is Ile, Val or tert-butylglycine; $Xaa_{24}$ is Ala, Glu or Asp; $Xaa_{25}$ is Ala, Trp or Phe; $Xaa_{26}$ is Ala or Leu; $Xaa_{27}$ is Ala or Lys; $Xaa_{28}$ is Ala or Asn; $Z_1$ is —OH, —$NH_2$, Gly-$Z_2$, Gly Gly-$Z_2$, Gly Gly $Xaa_{31}$-$Z_2$, Gly Gly $Xaa_{31}$ Ser-$Z_2$, Gly Gly $Xaa_{31}$ Ser Ser-$Z_2$, Gly Gly $Xaa_{31}$ Ser Ser Gly-$Z_2$, Gly Gly $Xaa_{31}$ Ser Ser Gly Ala-$Z_2$, Gly Gly $Xaa_{31}$ Ser Ser Gly Ala $Xaa_{31}$-$Z_2$, Gly Gly $Xaa_{31}$ Ser Ser Gly Ala $Xaa_{36}$ $Xaa_{37}$-$Z_2$, Gly Gly $Xaa_{31}$ Ser Ser Gly Ala $Xaa_{36}$ $Xaa_{37}$ $Xaa_{38}$-$Z_2$ or Gly Gly $Xaa_{31}$ Ser Ser Gly Ala $Xaa_{36}$ $Xaa_{37}$ $Xaa_{38}$ $Xaa_{39}$-$Z_2$; $Xaa_{31}$, $Xaa_{36}$, $Xaa_{37}$ and $Xaa_{38}$ being independently Pro homoproline, thioproline or N-methylalanine; and $Z_2$ being —OH or —$NH_2$; provided that no more than three of $Xaa_3$, $Xaa_5$, $Xaa_6$, $Xaa_8$, $Xaa_{10}$, $Xaa_{11}$, $Xaa_{12}$, $Xaa_{13}$, $Xaa_{14}$, $Xaa_{15}$, $Xaa_{16}$, $Xaa_{17}$, $Xaa_{19}$, $Xaa_{20}$, $Xaa_{21}$, $Xaa_{24}$, $Xaa_{25}$, $Xaa_{26}$, $Xaa_{27}$ and $Xaa_{28}$ are Ala; and provided also that, if $Xaa_1$ is His, Arg or Tyr, then at least one of $Xaa_3$, $Xaa_4$ and $Xaa_9$ is Ala. Especially preferred compounds of formula (II) include those described in application Serial No. PCT/US98/24273, filed Nov. 13, 1998, entitled "Novel Exendin Agonist Compounds" as having the amino acid sequence of SEQ. ID. NOS. 5–93 therein.

According to an especially preferred aspect, provided are compounds of formula (II) where $Xaa_{14}$ is Ala, Leu, Ile, Val or pentylglycine, more preferably Leu or pentylglycine, and $Xaa_{25}$ is Ala, Phe, Tyr or naphthylalanine, more preferably Phe or naphthylalanine. These compounds will be less susceptible to oxidative degration, both in vitro and in vivo, as well as during synthesis of the compound.

Formula III

Also within the scope of the present invention are narrower genera of compounds having peptides of various lengths, for example genera of compounds which do not include peptides having a length of 28, 29 or 30 amino acid residues, respectively. Additionally, the present invention includes narrower genera of compounds described in PCT application Serial No. PCT/US98/24210, filed Nov. 13, 1998, entitled "Novel Exendin Agonist Compounds" and having particular amino acid sequences, for example, compounds of the formula (III) [SEQ. ID. NO: 43]:

$Xaa_1$ $Xaa_2$ $Xaa_3$ Gly $Xaa_5$ $Xaa_6$ $Xaa_7$ $Xaa_8$ $Xaa_9$ $Xaa_{10}$
 $Xaa_{11}$ $Xaa_{12}$ $Xaa_{13}$ $Xaa_{14}$ $Xaa_{15}$ $Xaa_{16}$ $Xaa_{17}$ Ala $Xaa_{18}$

Xaa$_{19}$ Xaa$_{20}$ Xaa$_{21}$ Xaa$_{22}$ Xaa$_{23}$ Xaa$_{24}$ Xaa$_{25}$ Xaa$_{26}$ Xaa$_{27}$ Xaa$_{28}$-Z$_1$;
wherein
Xaa$_1$ is His or Arg;
Xaa$_2$ is Gly or Ala;
Xaa$_3$ is Asp or Glu;
Xaa$_5$ is Ala or Thr;
Xaa$_6$ is Ala, Phe or naphthylalanine;
Xaa$_7$ is Thr or Ser;
Xaa$_8$ is Ala, Ser or Thr;
Xaa$_9$ is Asp or Glu;
Xaa$_{10}$ is Ala, Leu or pentylglycine;
Xaa$_{11}$ is Ala or Ser;
Xaa$_{12}$ is Ala or Lys;
Xaa$_{13}$ is Ala or Gln;
Xaa$_{14}$ is Ala, Leu or pentylglycine;
Xaa$_{15}$ is Ala or Glu;
Xaa$_{16}$ is Ala or Glu;
Xaa$_{17}$ is Ala or Glu;
Xaa$_{19}$ is Ala or Val;
Xaa$_{20}$ is Ala or Arg;
Xaa$_{21}$ is Ala or Leu;
Xaa$_{22}$ is Phe or naphthylalanine;
Xaa$_{23}$ is Ile, Val or tert-butylglycine;
Xaa$_{24}$ is Ala, Glu or Asp;
Xaa$_{25}$ is Ala, Trp, or Phe;
Xaa$_{26}$ is Ala or Leu;
Xaa$_{27}$ is Ala or Lys;
Xaa$_{28}$ is Ala or Asn;
Z$_1$ is —OH,
—NH$_2$,
Gly-Z$_2$,
Gly Gly -Z$_2$,
Gly Gly Xaa$_{31}$-Z$_2$,
Gly Gly Xaa$_{31}$ Ser-Z$_2$,
Gly Gly Xaa$_{31}$ Ser Ser-Z$_2$,
Gly Gly Xaa$_{31}$ Ser Ser Gly-Z$_2$,
Gly Gly Xaa$_{31}$ Ser Ser Gly Ala-Z$_2$,
Gly Gly Xaa$_{31}$ Ser Ser Gly Ala Xaa$_{36}$-Z$_2$,
Gly Gly Xaa$_{31}$ Ser Ser Gly Ala Xaa$_{36}$ Xaa$_{37}$-Z$_2$ or Gly Gly
Xaa$_{31}$ Ser Ser Gly Ala Xaa$_{36}$ Xaa$_{37}$ Xaa$_{38}$-Z$_2$;
Xaa$_{31}$, Xaa$_{36}$, $_{Xaa37}$ and Xaa$_{38}$ are independently selected from the group consisting of Pro, homoproline, thioproline and N-methylalanine; and
Z$_2$ is —OH or —NH$_2$;
provided that no more than three of Xaa$_3$, Xaa$_5$, Xaa$_6$, Xaa$_8$, Xaa$_{10}$, Xaa$_{11}$, Xaa$_{12}$, Xaa$_{13}$, Xaa$_{14}$, Xaa$_{15}$, Xaa$_{16}$, Xaa$_{17}$, Xaa$_{19}$, Xaa$_{20}$, Xaa$_{21}$, Xaa$_{24}$, Xaa$_{25}$, Xaa$_{26}$, Xaa$_{27}$ and Xaa$_{28}$ are Ala; and pharmaceutically acceptable salts thereof.

Formula IV

Additionally, the present invention includes narrower genera of peptide compounds described in PCT application Serial No. PCT/US98/24273, filed Nov. 13, 1998, entitled "Novel Exendin Agonist Compounds" as having particular amino acid sequences, for example, compounds of the formula [IV] [SEQ. ID. NO: 44]:
Xaa$_1$ Xaa$_2$ Xaa$_3$ Xaa$_5$ Xaa$_6$ Xaa$_6$ Xaa$_7$ Xaa$_8$ Xaa$_9$ Xaa$_{10}$ Xaa$_{11}$ Xaa$_{12}$ Xaa$_{13}$ Xaa$_{14}$ Xaa$_{15}$ Xaa$_{16}$ Xaa$_{17}$ Ala Xaa$_{18}$ Xaa$_{19}$ Xaa$_{20}$ Xaa$_{21}$ Xaa$_{22}$ Xaa$_{23}$ Xaa$_{24}$ Xaa$_{25}$ Xaa$_{26}$ Xaa$_{27}$ Xaa$_{28}$-Z$_1$; wherein
Xaa$_1$ is His or Ala;
Xaa$_2$ is Gly or Ala;
Xaa$_3$ is Ala, Asp or Glu;
Xaa$_4$ is Ala or Gly;
Xaa$_5$ is Ala or Thr;
Xaa$_6$ is Phe or naphthylalanine;
Xaa$_7$ is Thr or Ser;
Xaa$_8$ is Ala, Ser or Thr;
Xaa$_9$ is Ala, Asp or Glu;
Xaa$_{10}$ is Ala, Leu or pentylglycine;
Xaa$_{11}$ is Ala or Ser;
Xaa$_{12}$ is Ala or Lys;
Xaa$_{13}$ is Ala or Gln;
Xaa$_{14}$ is Ala, Leu, Met or pentylglycine;
Xaa$_{15}$ is Ala or Glu;
Xaa$_{16}$ is Ala or Glu;
Xaa$_{17}$ is Ala or Glu;
Xaa$_{19}$ is Ala or Val;
Xaa$_{20}$ is Ala or Arg;
Xaa$_{21}$ is Ala or Leu;
Xaa$_{22}$ is Phe or naphthylalanine;
Xaa$_{23}$ is Ile, Val or tert-butylglycine;
Xaa$_{24}$ is Ala, Glu or Asp;
Xaa$_{25}$ is Ala, Trp or Phe;
Xaa$_{26}$ is Ala or Leu;
Xaa$_{27}$ is Ala or Lys;
Xaa$_{28}$ is Ala or Asn;
Z$_1$ is —OH,
—NH$_2$,
Gly-Z$_2$,
Gly Gly-Z$_2$
Gly Gly Xaa$_{31}$-Z$_2$,
Gly Gly Xaa$_{31}$ Ser-Z$_2$,
Gly Gly Xaa$_{31}$ Ser Ser-Z$_2$,
Gly Gly Xaa$_{31}$ Ser Ser Gly-Z$_2$,
Gly Gly Xaa$_{31}$ Ser Ser Gly Ala-Z$_2$,
Gly Gly Xaa$_{31}$ Ser Ser Gly Ala Xaa$_{36}$-Z$_2$,
Gly Gly Xaa$_{31}$ Ser Ser Gly Ala Xaa$_{36}$ Xaa$_{37}$-Z$_2$
Gly Gly Xaa$_{31}$ Ser Ser Gly Ala Xaa$_{36}$ Xaa$_{37}$ Xaa$_{38}$-Z$_2$
Gly Gly Xaa$_{31}$ Ser Ser Gly Ala Xaa$_{36}$ Xaa$_{37}$ Xaa$_{38}$ Ser-Z$_2$;
Xaa$_{31}$ Xaa$_{36}$, Xaa$_{37}$ and Xaa$_{38}$ are independently Pro, homoproline, thioproline, or N-methylalanine; and
Z$_2$ is —OH or —NH$_2$;
provided that no more than three of Xaa$_3$, Xaa$_5$, Xaa$_6$, Xaa$_8$, Xaa$_{10}$, Xaa$_{11}$, Xaa$_{12}$, Xaa$_{13}$, Xaa$_{14}$, Xaa$_{15}$, Xaa$_{16}$, Xaa$_{17}$, Xaa$_{19}$, Xaa$_{20}$, Xaa$_{21}$, Xaa$_{24}$, Xaa$_{25}$, Xaa$_{26}$, Xaa$_{27}$, and Xaa$_{28}$ are Ala; and
provided that, if Xaa$_1$ is His, Arg or Tyr, then at least one of Xaa$_3$, Xaa$_4$ and Xaa$_9$ is Ala; and pharmaceutically acceptable salts thereof.

Preferred compounds of formula (IV) include those wherein Xaa$_1$ is His, Ala, Norval or 4-imidazopropionyl. Preferably, Xaa$_1$ is His, or $_4$-imidazopropionyl or Ala, more preferably His or 4-imidazopropionyl.

Preferred compounds of formula (IV) include those wherein Xaa$_2$ is Gly.

Preferred compounds of formula (IV) include those wherein Xaa$_4$ is Ala.

Preferred compounds of formula (IV) include those wherein Xaa$_9$ is Ala.

Preferred compounds of formula (IV) include those wherein Xaa$_{14}$ is Leu, pentylglycine or Met.

Preferred compounds of formula (IV) include those wherein Xaa$_{25}$ is Trp or Phe.

Preferred compounds of formula (IV) include those wherein Xaa$_6$ is Ala, Phe or naphthylalanine; Xaa$_{22}$ is Phe or naphthylalanine; and Xaa$_{23}$ is Ile or Val.

Preferred compounds of formula (IV) include those wherein Z$_1$ is —NH$_2$.

Preferred compounds of formula (IV) include those wherein Xaa$_{31}$, Xaa$_{36}$, Xaa$_{37}$ and Xaa$_{38}$ are independently selected from the group consisting of Pro, homoproline, thioproline and N-alkylalanine.

Preferred compounds of formula (IV) include those wherein $Xaa_{39}$ is Ser or Tyr, preferably Ser.

Preferred compounds of formula (IV) include those wherein $Z_2$ is —$NH_2$.

Preferred compounds of formula (IV) include those 42 wherein $Z_1$ is —$NH_2$.

Preferred compounds of formula (IV) include those wherein $Xaa_{21}$ is Lys-$NH^\epsilon$—R where R is Lys, Arg, $C_1$–$C_{10}$ straight chain or branched alkanoyl.

Preferred compounds of formula (IV) include those wherein $X_1$ is Lys Asn, Lys-$NH^\epsilon$—R Asn, or Lys-$NH^\epsilon$—R Ala where R is Lys, Arg, $C_1$–$C_{10}$ straight chain or branched alkanoyl. Preferred compounds of formula (IV) include those having an amino acid sequence described in PCT application Serial No. PCT/US98/24273, filed Nov. 13, 1998, entitled "Novel Exendin Agonist Compounds" as being selected from SEQ. ID. NOS. 95–110 therein.

Formula V

Also provided are compounds described in PCT application PCT/US98/24210, filed Nov. 13, 1998, entitled "Novel Exendin Agonist Compounds", including compounds of the formula (V) [SEQ. ID. NO: 45]:

$Xaa_1$ $Xaa_2$ $Xaa_3$ Gly $Xaa_5$ $Xaa_6$ $Xaa_7$ $Xaa_8$ $Xaa_9$ $Xaa_{10}$ $Xaa_{11}$ $Xaa_{12}$ $Xaa_{13}$ $Xaa_{14}$ $Xaa_{15}$ $Xaa_{16}$ $Xaa_{17}$ Ala $Xaa_{19}$ $Xaa_{20}$ $Xaa_{21}$ $Xaa_{22}$ $Xaa_{23}$ $Xaa_{24}$ $Xaa_{25}$ $Xaa_{26}$ $X_1$-$Z_1$;

wherein $Xaa_1$ is His, Arg or Tyr or 4-imidazopropionyl;
$Xaa_2$ is Ser, Gly, Ala or Thr;
$Xaa_3$ is Asp or Glu;
$Xaa_5$ is Ala or Thr;
$Xaa_6$ is Ala, Phe, Tyr or naphthylalanine;
$Xaa_7$ is Thr or Ser;
$Xaa_8$ is Ala, Ser or Thr;
$Xaa_9$ is Asp or Glu;
$Xaa_{10}$ is Ala, Leu, Ile, Val, pentylglycine or Met;
$Xaa_{11}$ is Ala or Ser;
$Xaa_{12}$ is Ala or Lys;
$Xaa_{13}$ is Ala or Gln;
$Xaa_{14}$ is Ala, Leu, Ile, pentylglycine, Val or Met;
$Xaa_{15}$ is Ala or Glu;
$Xaa_{16}$ is Ala or Glu;
$Xaa_{17}$ is Ala or Glu;
$Xaa_{19}$ is Ala or Val;
$Xaa_{20}$ is Ala or Arg;
$Xaa_{21}$ is Ala, Leu or Lys-$NH^\epsilon$—R where R is Lys, Arg, $C_1$–$C_{10}$ straight chain or branched alkanoyl or cycloalkylalkanoyl;
$Xaa_{22}$ is Phe, Tyr or naphthylalanine;
$Xaa_{23}$ is Ile, Val, Leu, pentylglycine, tert-butylglycine or Met;
$Xaa_{24}$ is Ala, Glu or Asp;
$Xaa_{25}$ is Ala, Trp, Phe, Tyr or naphthylalanine;
$Xaa_{26}$ is Ala or Leu;
$X_1$ is Lys Asn, Asn Lys, Lys-$NH^\epsilon$—R Asn, Asn Lys-$NH^\epsilon$—R, Lys-$NH^\epsilon$—R Ala, Ala Lys-$NH^\epsilon$—R where R is Lys, Arg, $C_1$–$C_{10}$ straight chain or branched alkanoyl or cycloalkylalkanoyl
$Z_1$ is —OH,
—$NH_2$,
Gly-$Z_2$,
Gly Gly-$Z_2$,
Gly Gly $Xaa_{31}$-$Z_2$,
Gly Gly $Xaa_{31}$ Ser-$Z_2$,
Gly Gly $Xaa_{31}$ Ser Ser-$Z_2$,
Gly Gly $Xaa_{31}$ Ser Ser Gly-$Z_2$,
Gly Gly $Xaa_{31}$ Ser Ser Gly Ala-$Z_2$,
Gly Gly $Xaa_{31}$ Ser Ser Gly Ala $Xaa_{36}$-$Z_2$,
Gly Gly $Xaa_{31}$ Ser Ser Gly Ala $Xaa_{36}$ $Xaa_{37}$-$Z_2$ or
Gly Gly $Xaa_{31}$ Ser Ser Gly Ala $Xaa_{36}$ $Xaa_{37}$ $Xaa_{38}$-$Z_2$;

wherein $Xaa_{31}$, $Xaa_{36}$, $Xaa_{37}$ and $Xaa_{38}$ are independently selected from the group consisting of Pro, homoproline, 3Hyp, 4Hyp, thioproline,
N-alkylglycine, N-alkylpentylglycine and
N-alkylalanine; and
$Z_2$ is —OH or —$NH_2$;

provided that no more than three of $Xaa_3$, $Xaa_5$, $Xaa_6$, $Xaa_8$, $Xaa_{10}$, $Xaa_{11}$, $Xaa_{12}$, $Xaa_{13}$, $Xaa_{14}$, $Xaa_{15}$, $Xaa_{16}$, $Xaa_{17}$, $Xaa_{19}$, $Xaa_{20}$, $Xaa_{21}$, $Xaa_{24}$, $Xaa_{25}$, $Xaa_{26}$, $Xaa_{27}$, and $Xaa_{28}$ are Ala. Also within the scope of the present invention are pharmaceutically acceptable salts of the compound of formula (V) and pharmaceutical compositions including said compounds and salts thereof.

Preferred exendin agonist compounds of formula (V) include those wherein $Xaa_1$ is His, Tyr or 4-imidazopropionyl. More preferably $Xaa_1$ is His.

Preferred are those compounds of formula (V) wherein $Xaa_1$ is 4-imidazopropionyl.

Preferred are those compounds of formula (V) wherein $Xaa_2$ is Gly.

Preferred compounds of formula (V) are those wherein $Xaa_{14}$ is Leu, pentylglycine or Met.

Preferred compounds of formula (V) are those wherein $Xaa_{25}$ is Trp or Phe.

According to one aspect, preferred are compounds of formula (V) wherein $Xaa_6$ is Phe or naphthylalanine; and $Xaa_{22}$ is Phe or naphthylalanine; and $Xaa_{23}$ is Ile or Val. More preferably, $Z_1$ is —$NH_2$. According to one aspect, especially preferred are such compounds of formula (V) wherein $Xaa_{31}$, $Xaa_{36}$, $Xaa_{37}$ and $Xaa_{38}$ are independently selected from the group consisting of Pro, homoproline, thioproline and N-alkylalanine. More prefers, $Z_2$ is —$NH_2$.

Preferred compounds of formula (V) include those wherein $X_1$ is Lys Asn, Lys-$NH^\epsilon$—R Asn, or Lys-$NH^\epsilon$—R Ala where R is Lys, Arg, $C_1$–$C_{10}$ straight chain or branched alkanoyl. Preferred compounds of formula (V) include compounds described in PCT application Serial No. PCT/US98/24210, filed Nov. 13, 1998, entitled "Novel Exendin Agonist Compounds" and identified therein as Compound Nos. 62–69.

Preferred such exendin agonist compounds include those wherein $Xaa_1$ is His, Ala or Norval. More preferably $Xaa_1$ is His or Ala. Most preferably $Xaa_1$ is His.

Preferred are those compounds of formula (V) wherein $Xaa_2$ is Gly.

Preferred are those compounds of formula (V) wherein $Xaa_3$ is Ala.

Preferred are those compounds of formula (V) wherein $Xaa_4$ is Ala.

Preferred are those compounds of formula (V) wherein $Xaa_9$ is Ala.

Preferred are those compounds of formula (V) wherein $Xaa_{14}$ is Leu, pentylglycine or Met.

Preferred compounds of formula (V) are those wherein $Xaa_{25}$ is Trp or Phe.

Preferred compounds of formula (V) are those where $Xaa_6$ is Ala, Phe or naphthylalanine; $Xaa_{22}$ is Phe or naphthylalanine; and $Xaa_{23}$ is Ile or Val.

Preferred are compounds of formula (V) wherein $Xaa_{31}$, $Xaa_{36}$, $Xaa_{37}$ and $Xaa_{38}$ are independently selected from Pro, homoproline, thioproline and N-alkylalanine.

Preferably $Z_1$ is —$NH_2$.
Preferably $Z_2$ is —$NH_2$.

According to one aspect, preferred are compounds of formula (V) wherein $Xaa_1$ is Ala, His or Tyr, more preferably Ala or His; $Xaa_2$ is Ala or Gly; $Xaa_6$ is Phe or naphthylalanine; $Xaa_{14}$ is Ala, Leu, pentylglycine or Met; $Xaa_{22}$ is Phe or naphthylalanine; $Xaa_{23}$ is Ile or Val; $Xaa_{31}$, $Xaa_{36}$, $Xaa_{37}$ and $Xaa_{38}$ are independently selected from Pro, homoproline, thioproline or N-alkylalanine; and $Xaa_{39}$ is Ser or Tyr, more preferably Ser. More preferably $Z_1$ is —$NH_2$.

According to an especially preferred aspect, especially preferred compounds include those of formula (V) wherein: $Xaa_1$ is His or Ala; $Xaa_2$ is Gly or Ala; $Xaa_3$ is Ala, Asp or Glu; $Xaa_4$ is Ala or Gly; $Xaa_5$ is Ala or Thr; $Xaa_6$ is Phe or naphthylalanine; $Xaa_7$ is Thr or Ser; $Xaa_8$ is Ala, Ser or Thr; $Xaa_9$ is Ala, Asp or Glu; $Xaa_{10}$ is Ala, Leu or pentylglycine; $Xaa_{11}$ is Ala or Ser; $Xaa_{12}$ is Ala or Lys; $Xaa_{13}$ is Ala or Gln; $Xaa_{14}$ is Ala, Leu, Met or pentylglycine; $Xaa_{15}$ is Ala or Glu; $Xaa_{16}$ is Ala or Glu; $Xaa_{17}$ is Ala or Glu; $Xaa_{19}$ is Ala or Val; $Xaa_{20}$ is Ala or Arg; $Xaa_{21}$ is Ala or Leu; $Xaa_{22}$ is Phe or naphthylalanine; $Xaa_{23}$ is Ile, Val or tert-butylglycine; $Xaa_{24}$ is Ala, Glu or Asp; $Xaa_{25}$ is Ala, Trp or Phe; $Xaa_{26}$ is Ala or Leu; $Xaa_{27}$ is Ala or Lys; $Xaa_{28}$ is Ala or Asn; $Z_1$ is —OH, —$NH_2$, Gly-$Z_2$, Gly Gly-$Z_2$, Gly Gly $Xaa_{31}$-$Z_2$, Gly Gly $Xaa_{31}$ Ser-$Z_2$, Gly Gly $Xaa_{31}$ Ser Ser-$Z_2$, Gly Gly $Xaa_{31}$ Ser Ser Gly-$Z_2$, Gly Gly $Xaa_{31}$ Ser Ser Gly Ala-$Z_2$, Gly Gly $Xaa_{31}$ Ser Ser Gly Ala $Xaa_{31}$-$Z_2$, Gly Gly $Xaa_{31}$ Ser Ser Gly Ala $Xaa_{36}$ $Xaa_{37}$-$Z_2$, Gly Gly $Xaa_{31}$ Ser Ser Gly Ala $Xaa_{36}$ $Xaa_{37}$ $Xaa_{38}$-$Z_2$ or Gly Gly $Xaa_{31}$ Ser Ser Gly Ala $Xaa_{36}$ $Xaa_{37}$ $Xaa_{38}$ $Xaa_{39}$-$Z_2$; $Xaa_{31}$, $Xaa_{36}$, $Xaa_{37}$ and $Xaa_{38}$ being independently Pro homoproline, thioproline or N-methylalanine; and $Z_2$ being —OH or —$NH_2$; provided that no more than three of $Xaa_3$, $Xaa_5$, $Xaa_6$, $Xaa_8$, $Xaa_{10}$, $Xaa_{11}$, $Xaa_{12}$, $Xaa_{13}$, $Xaa_{14}$, $Xaa_{15}$, $Xaa_{16}$, $Xaa_{17}$, $Xaa_{19}$, $Xaa_{20}$, $Xaa_{21}$, $Xaa_{24}$, $Xaa_{25}$, $Xaa_{26}$, $Xaa_{27}$ and $Xaa_{28}$ are Ala; and provided also that, if $Xaa_1$ is His, Arg or Tyr, then at least one of $Xaa_3$, $Xaa_4$ and $Xaa_9$ is Ala. Especially preferred compounds of formula (V) include those described in application Serial No. PCT/US98/24210, filed Nov. 13, 1998, entitled "Novel Exendin Agonist Compounds" as having the amino acid sequence of SEQ. ID. NOS. 5–93 therein.

According to an especially preferred aspect, provided are compounds of formula (V) where $Xaa_{14}$ is Ala, Leu, Ile, Val or pentylglycine, more preferably Leu or pentylglycine, and $Xaa_{25}$ is Ala, Phe, Tyr or naphthylalanine, more preferably Phe or naphthylalanine. These compounds will be less susceptible to oxidative degration, both in vitro and in vivo, as well as during synthesis of the compound.

Formula VI

Also provided are peptide compounds described in PCT Application Serial No. PCT/US98/24273, filed Nov. 13, 1998, entitled "Novel Exendin Agonist Compounds", including compounds of the formula (VI) [SEQ. ID. NO: 46]:

$Xaa_1$ $Xaa_2$ $Xaa_3$ Gly $Xaa_5$ $Xaa_6$ $Xaa_7$ $Xaa_8$ $Xaa_9$ $Xaa_{10}$ $Xaa_{11}$ $Xaa_{12}$ $Xaa_{13}$ $Xaa_{14}$ $Xaa_{15}$ $Xaa_{16}$ $Xaa_{17}$ Ala $Xaa_{19}$ $Xaa_{20}$ $Xaa_{21}$ $Xaa_{22}$ $Xaa_{23}$ $Xaa_{24}$ $Xaa_{25}$ $Xaa_{26}$ $X_1$-$Z_1$;
wherein
$Xaa_1$ is His, Arg or Tyr or 4-imidazopropionyl;
$Xaa_2$ is Ser, Gly, Ala or Thr;
$Xaa_3$ is Asp or Glu;
$Xaa_5$ is Ala or Thr;
$Xaa_6$ is Ala, Phe, Tyr or naphthylalanine;
$Xaa_7$ is Thr or Ser;
$Xaa_8$ is Ala, Ser or Thr;
$Xaa_9$ is Asp or Glu;
$Xaa_{10}$ is Ala, Leu, Ile, Val, pentylglycine or Met;
$Xaa_{11}$ is Ala or Ser;
$Xaa_{12}$ is Ala or Lys;
$Xaa_{13}$ is Ala or Gln;
$Xaa_{14}$ is Ala, Leu, Ile, pentylglycine, Val or Met;
$Xaa_{15}$ is Ala or Glu;
$Xaa_{16}$ is Ala or Glu;
$Xaa_{17}$ is Ala or Glu;
$Xaa_{19}$ is Ala or Val;
$Xaa_{20}$ is Ala or Arg;
$Xaa_{21}$ is Ala, Leu or Lys-$NH^\epsilon$—R where R is Lys, Arg, $C^{1-10}$ straight chain or branched alkanoyl or cycloalkylalkanoyl;
$Xaa_{22}$ is Phe, Tyr or naphthylalanine;
$Xaa_{23}$ is Ile, Val, Leu, pentylglycine, tert-butylglycine or Met;
$Xaa_{24}$ is Ala, Glu or Asp;
$Xaa_{25}$ is Ala, Trp, Phe, Tyr or naphthylalanine;
$Xaa_{26}$ is Ala or Leu;
$X_1$ is Lys Asn, Asn Lys, Lys-$NH^\epsilon$—R Asn, Asn Lys-$NH^\epsilon$—R, Lys-$NH^\epsilon$—R Ala, Ala Lys-$NH^\epsilon$—R where R is Lys, Arg, $C_1$–$C_{10}$ straight chain or branched alkanoyl or cycloalkylalkanoyl
$Z_1$ is —OH,
—$NH_2$,
Gly-$Z_2$,
Gly Gly-$Z_2$,
Gly Gly $Xaa_{31}$-$Z_2$,
Gly Gly $Xaa_{31}$ Ser-$Z_2$,
Gly Gly $Xaa_{31}$ Ser Ser-$Z_2$,
Gly Gly $Xaa_{31}$ Ser Ser Gly-$Z_2$,
Gly Gly $Xaa_{31}$ Ser Ser Gly Ala-$Z_2$,
Gly Gly $Xaa_{31}$ Ser Ser Gly Ala $Xaa_{36}$-$Z_2$,
Gly Gly $Xaa_{31}$ Ser Ser Gly Ala $Xaa_{36}$ $Xaa_{37}$-$Z_2$ or
Gly Gly $Xaa_{31}$ Ser Ser Gly Ala $Xaa_{36}$ $Xaa_{37}$ $Xaa_{38}$-$Z_2$;
wherein
$Xaa_{31}$, $Xaa_{36}$, $Xaa_{37}$ and $Xaa_{38}$ are independently selected from the group consisting of Pro, homoproline, 3Hyp, 4Hyp, thioproline,
N-alkylglycine, N-alkylpentylglycine and
N-alkylalanine; and
$Z_2$ is —OH or —$NH_2$;
provided that no more than three of $Xaa_3$, $Xaa_5$, $Xaa_6$, $Xaa_8$, $Xaa_{10}$, $Xaa_{11}$, $Xaa_{12}$, $Xaa_{13}$, $Xaa_{14}$, $Xaa_{15}$, $Xaa_{16}$, $Xaa_{17}$, $Xaa_{19}$, $Xaa_{20}$, $Xaa_{21}$, $Xaa_{24}$, $Xaa_{25}$, $Xaa_{26}$, $Xaa_{27}$, and $Xaa_{28}$ are Ala; and
provided also that, if $Xaa_1$ is His, Arg, Tyr, or 4-imidazopropionyl then at least one of $Xaa_3$, $Xaa_4$ and $Xaa_9$ is Ala.

Preferred compounds of formula (VI) include those wherein $Xaa_1$ is His, Ala, Norval or 4-imidazopropionyl. Preferably, $Xaa_1$ is His, or 4-imidazopropionyl or Ala, more preferably His or 4-imidazopropionyl.

Preferred compounds of formula (VI) include those wherein $Xaa_2$ is Gly.

Preferred compounds of formula (VI) include those wherein $Xaa_4$ is Ala.

Preferred compounds of formula (VI) include those wherein $Xaa_9$ is Ala.

Preferred compounds of formula (VI) include those wherein $Xaa_{14}$ is Leu, pentylglycine or Met.

Preferred compounds of formula (VI) include those wherein $Xaa_{25}$ is Trp or Phe.

Preferred compounds of formula (VI) include those wherein $Xaa_6$ is Ala, Phe or naphthylalanine; $Xaa_{22}$ is Phe or naphthylalanine; and $Xaa_{23}$ is Ile or Val.

Preferred compounds of formula (VI) include those wherein $Z_1$ is —$NH_2$.

21

Preferred compounds of formula (VI) include those wherein $Xaa_{31}$, $Xaa_{36}$, $Xaa_{37}$ and $Xaa_{38}$ are independently selected from the group consisting of Pro, homoproline, thioproline and N-alkylalanine.

Preferred compounds of formula (VI) include those wherein $Xaa_{39}$ is Ser or Tyr, preferably Ser.

Preferred compounds of formula (VI) include those wherein $Z_2$ is —$NH_2$.

Preferred compounds of formula (VI) include those wherein $Z_1$ is —$NH_2$.

Preferred compounds of formula (VI) include those wherein $Xaa_{21}$ is Lys-$NH^\epsilon$—R where R is Lys, Arg, $C_1$–$C_{10}$ straight chain or branched alkanoyl.

Preferred compounds of formula (VI) include those wherein $X_1$ is Lys Asn, Lys-$NH^\epsilon$—R Asn, or Lys-$NH^\epsilon$—R Ala where R is Lys, Arg, $C_1$–$C_{10}$ straight chain or branched alkanoyl.

Preferred compounds of formula (VI) include those described in PCT Application Serial No. PCT/US98/24273, filed Nov. 13, 1998, entitled "Novel Exendin Agonist Compounds" as having an amino acid sequence selected from those identified therein as SEQ. ID. NOS: 95–110.

Formula VII

Compounds particularly useful according to the present invention are exendin agonist compounds described in U.S. patent application Ser. No. 09/003,869, filed Jan. 7, 1998, entitled "Use of Exendins And Agonists Thereof For The Reduction of Food Intake", including compounds of the formula (VII) "SEQ. ID. NO: 47 ":

```
1                    5                      10
Xaa₁ Xaa₂ Xaa₃ Gly Thr Xaa₄ Xaa₅ Xaa₆ Xaa₇ Xaa₈

15                 20
Ser Lys Gln Xaa₉ Glu Glu Glu Ala Val Arg Leu 25              30
Xaa₁₀ Xaa₁₁ Xaa₁₂ Xaa₁₃ Leu Lys Asn Gly Gly Xaa₁₄

35
Ser Ser Gly Ala Xaa₁₅ Xaa₁₆ Xaa₁₇ Xaa₁₈-Z
``` wherein $Xaa_1$ is His, Arg or Tyr; $Xaa_2$ is Ser, Gly, Ala or Thr; $Xaa_3$ is Asp or Glu; $Xaa_4$ is Phe, Tyr or naphthalanine; $Xaa_5$ is Thr or Ser; $Xaa_6$ is Ser or Thr; $Xaa_7$ is Asp or Glu; $Xaa_8$ is Leu, Ile, Val, pentylglycine or Met; $Xaa_9$ is Leu, Ile, pentylglycine, Val or Met; $Xaa_{10}$ is Phe, Tyr or naphthalanine; $Xaa_{11}$ is Ile, Val, Leu, pentylglycine, tert-butylglycine or Met; $Xaa_{12}$ is Glu or Asp; $Xaa_{13}$ is Trp, Phe, Tyr, or naphthylalanine; $Xaa_{14}$, $Xaa_{15}$, $Xaa_{16}$ and $Xaa_{17}$ are independently Pro, homoproline, 3Hyp, 4Hyp, thioproline, N-alkylglycine, N-alkylpentylglycine or N-alkylalanine; $Xaa_{18}$ is Ser, Thr or Tyr; and Z is —OH or —$NH_2$; with the proviso that the compound does not have the formula of either SEQ. ID. NOS: 1 or 2. Preferred N-alkyl groups for N-alkylglycine, N-alkylpentylglycine and N-alkylalanine include lower N-alkyl groups preferably of 1 to about 6 carbon atoms, more preferably of 1 to 4 carbon atoms. Suitable compounds include those having amino acid sequences of SEQ. ID. NOS: 10 to 40. Also useful in the present invention are pharmaceutically acceptable salts of the compounds of formula (VII).

Preferred exendin agonist compounds include those wherein $Xaa_1$ is His or Tyr. More preferably $Xaa_1$ is His.

Preferred are those compounds wherein $Xaa_2$ is Gly.

Preferred are those compounds wherein $Xaa_9$ is Leu, pentylglycine or Met.

Preferred compounds include those wherein $Xaa_{13}$ is Trp or Phe.

22

Also preferred are compounds where $Xaa_4$ is Phe or naphthalanine; $Xaa_{11}$ is Ile or Val and $Xaa_{14}$, $Xaa_{15}$, $Xaa_{16}$ and $Xaa_{17}$ are independently selected from Pro, homoproline, thioproline or N-alkylalanine. Preferably N-alkylalanine has a N-alkyl group of 1 to about 6 carbon atoms.

According to an especially preferred aspect, $Xaa_{15}$, $Xaa_{16}$ and $Xaa_{17}$ are the same amino acid reside.

Preferred are compounds wherein $Xaa_{18}$ is Ser or Tyr, more preferably Ser.

Preferably Z is —$NH_2$.

According to one aspect, preferred are compounds of formula (VII) wherein $Xaa_1$ is His or Tyr, more preferably His; $Xaa_2$ is Gly; $Xaa_4$ is Phe or naphthalanine; $Xaa_9$ is Leu, pentylglycine or Met; $Xaa_{10}$ is Phe or naphthalanine; $Xaa_{11}$ is Ile or Val; $Xaa_{14}$, $Xaa_{15}$, $Xaa_{16}$ and $Xaa_{17}$ are independently selected from Pro, homoproline, thioproline or N-alkylalanine; and $Xaa_{15}$ is Ser or Tyr, more preferably Ser.

More preferably Z is —$NH_2$.

According to an especially preferred aspect, especially preferred compounds include those of formula (VII) wherein: $Xaa_1$ is His or Arg; $Xaa_2$ is Gly; $Xaa_3$ is Asp or Glu; $Xaa_4$ is Phe or naphthylalanine; $Xaa_5$ is Thr or Ser; $Xaa_6$ is Ser or Thr; $Xaa_7$ is Asp or Glu; $Xaa_8$ is Leu or pentylglycine; $Xaa_9$ is Leu or pentylglycine; $Xaa_{10}$ is Phe or naphthylalanine; $Xaa_{11}$ is Ile, Val or t-butyltylglycine; $Xaa_{12}$ is Glu or Asp; $Xaa_{13}$ is Trp or Phe; $Xaa_{14}$, $Xaa_{15}$, $Xaa_{16}$, and $Xaa_{17}$ are independently Pro, homoproline, thioproline, or N-methylalanine; $Xaa_{18}$ is Ser or Tyr: and Z is —OH or —$NH_2$; with the proviso that the compound does not have the formula of either SEQ. ID. NOS: 1 or 2. More preferably Z is —$NH_2$. Especially preferred compounds include those having the amino acid sequence of SEQ. ID. NOS: 10, 11, 22, 23, 24, 27, 29, 36, 37 and 40.

According to an especially preferred aspect, provided are compounds where $Xaa_9$ is Leu, Ile, Val or pentylglycine, more preferably Leu or pentylglycine, and $Xaa_{13}$ is Phe, Tyr or naphthylalanine, more preferably Phe or naphthylalanine. These compounds are believed to exhibit advantageous duration of action and to be less subject to oxidative degration, both in vitro and in vivo, as well as during synthesis of the compound.

Formula VIII

Also provided are compounds described in PCT Application Serial No. PCT/US98/16387, filed Aug. 6, 1998, entitled "Novel Exendin Agonist Compounds", including compounds of the formula (VIII) [SEQ. ID. NO: 48]:

```
1                    5                      10
Xaa₁ Xaa₂ Xaa₃ Gly Thr Xaa₄ Xaa₅ Xaa₆ Xaa₇ Xaa₈

15                 20
Ser Lys Gln Xaa₉ Glu Glu Glu Ala Val Arg Leu 25              30
Xaa₁₀ Xaa₁₁ Xaa₁₂ Xaa₁₃ Leu X₁ Gly Gly Xaa₁₄

35
Ser Ser Gly Ala Xaa₁₅ Xaa₁₆ Xaa₁₇ Xaa₁₈-Z
``` wherein $Xaa_1$ is His, Arg, Tyr or 4-imidazopropionyl; $Xaa_2$ is Ser, Gly, Ala or Thr; $Xaa_3$ is Asp or Glu; $Xaa_4$ is Phe, Tyr or naphthylalanine; $Xaa_5$ is Thr or Ser; $Xaa_6$ is Ser or Thr; $Xaa_7$ is Asp or Glu; $Xaa_8$ is Leu, Ile, Val, pentylglycine or Met; $Xaa_9$ is Leu, Ile, pentylglycine, Val or Met; $Xaa_{10}$ is Phe, Tyr or naphthylalanine; $Xaa_{11}$ is Ile, Val, Leu, pentylglycine, tert-butylglycine or Met; $Xaa_{12}$ is Glu or Asp; $Xaa_{13}$ is Trp, Phe, Tyr, or naphthylalanine; $X_1$ is Lys Asn, Asn Lys, Lys-NH$^\epsilon$—R Asn, Asn Lys-NH$^\epsilon$—R where R is Lys, Arg, $C_1$–$C_{10}$ straight chain or branched alkanoyl or cycloalkylalkanoyl; $Xaa_{14}$, $Xaa_{15}$, $Xaa_{16}$, and $Xaa_{17}$ are independently Pro, homoproline, 3Hyp, 4Hyp, thioproline, N-alkylglycine, N-alkylpentylglycine or N-alkylalanine; $Xaa_{18}$ is Ser, Thr or Tyr; and Z is —OH or —NH$_2$; with the proviso that the compound does not have the formula of either SEQ. ID. NOS. 1 or 2. Suitable compounds of formula (VIII) include compounds described in PCT Application Ser. No. PCT/US98/16387, filed Aug. 6, 1998, entitled "Novel Exendin Agonist Compounds" having the amino acid sequences of SEQ. ID. NOS. 37–40 therein.

Preferred exendin agonist compounds of formula (VIII) include those wherein $Xaa_1$ is His, Tyr or 4-imidazopropionyl. More preferably, $Xaa_1$ is His or 4-imidazopropionyl.

Preferred are those compounds of formula (VIII) wherein $Xaa_2$ is Gly.

Preferred are those compounds of formula (VIII) wherein $Xaa_9$ is Leu, pentylglycine or Met.

Preferred are those compounds of formula (VIII) wherein $Xaa_{13}$ is Trp or Phe.

Preferred are those compounds of formula (VIII) wherein Lys-NH$^\epsilon$—R Asn, Asn Lys-NH$^\epsilon$—R where R is Lys, Arg, $C_1$–$C_{10}$ straight chain or branched alkanoyl.

Also preferred are compounds of formula (VIII) wherein $Xaa_4$ is Phe or naphthylalanine; $Xaa_{10}$ is Phe or naphthylalanine; $Xaa_{11}$ is Ile or Val and $Xaa_{14}$, $Xaa_{15}$, $Xaa_{16}$ and $Xaa_{17}$ are independently selected from Pro, homoproline, thioproline or N-alkylalanine. According to an especially preferred aspect, $Xaa_{18}$ is Ser or Tyr. Preferred are those such compounds wherein $Xaa_{18}$ is Ser. Preferably, Z is —NH$_2$.

According to one preferred aspect, preferred are compounds of formula (VIII) wherein $Xaa_4$ is Phe or naphthylalanine; $Xaa_{10}$ is Phe or naphthylalanine; $Xaa_{11}$ is Ile or Val, $X_1$ is Lys Asn, or Lys-NH$^\epsilon$—R Asn, where R is Lys, Arg, $C_1$–$C_{10}$ straight chain or branched alkanoyl and $Xaa_{14}$, $Xaa_{15}$, $Xaa_{16}$ and $Xaa_{17}$ are independently selected from Pro, homoproline, thioproline or N-alkylalanine.

Preparation of Modified Exendins and Exendin Agonists

The modified exendins and exendin agonists of the present invention may be made by linking one or more polyethylene glycol polymers to an exendin or exendin agonist. The synthesis of exendins and exendin agonists is thus described first, followed by methodology for linking the polyethylene glycol polymer(s) to the exendin or exendin agonist.

Preparation of Exendins and Exendin Agonists

Exendins and exendin agonist compounds such as exendin analogs and exendin derivatives, described herein may be prepared through peptide purification as described in, for example, Eng, et al., *J. Biol. Chem.* 265:20259–62, 1990; and Eng, et al., *J. Biol. Chem.* 267:7402–05, 1992, hereby incorporated by reference herein. Alternatively, exendins and exendin agonist peptides may be prepared by methods known to those skilled in the art, for example, as described in Raufman, et al. (*J. Biol. Chem.* 267:21432–37, 1992), hereby incorporated by reference herein, using standard solid-phase peptide synthesis techniques and preferably an automated or semiautomated peptide synthesizer. The compounds that constitute active ingredients of the formulations and dosages of the present invention may be prepared using standard solid-phase peptide synthesis techniques and preferably an automated or semiautomated peptide synthesizer. Typically, using such techniques, an α-N-carbamoyl protected amino acid and an amino acid attached to the growing peptide chain on a resin are coupled at room temperature in an inert solvent such as dimethylformamide, N-methylpyrrolidinone or methylene chloride in the presence of coupling agents such as dicyclohexylcarbodiimide and 1-hydroxybenzotriazole in the presence of a base such as diisopropylethylamine. The α-N-carbamoyl protecting group is removed from the resulting peptide-resin using a reagent such as trifluoroacetic acid or piperidine, and the coupling reaction repeated with the next desired N-protected amino acid to be added to the peptide chain. Suitable N-protecting groups are well known in the art, with t-butyloxycarbonyl (tBoc) and fluorenylmethoxycarbonyl (Fmoc) being preferred herein.

The solvents, amino acid derivatives and 4-methylbenzhydryl-amine resin used in the peptide synthesizer may be purchased from Applied Biosystems Inc. (Foster City, Calif.). The following side-chain protected amino acids may be purchased from Applied Biosystems, Inc.: BSD-112344.1-Arg(Pmc), Boc-Thr(Bzl), Fmoc-Thr(t-Bu), Boc-Ser(Bzl), Fmoc-Ser(t-Bu), Boc-Tyr(BrZ), Fmoc-Tyr(t-Bu), Boc-Lys(Cl-Z), Fmoc-Lys(Boc), Boc-Glu(Bzl), Fmoc-Glu(t-Bu), Fmoc-His(Trt), Fmoc-Asn(Trt), and Fmoc-Gln(Trt). Boc-His(BOM) may be purchased from Applied Biosystems, Inc. or Bachem Inc. (Torrance, Calif.). Anisole, dimethylsulfide, phenol, ethanedithiol, and thioanisole may be obtained from Aldrich Chemical Company (Milwaukee, Wis.). Air Products and Chemicals (Allentown, Pa.) supplies HF. Ethyl ether, acetic acid and methanol may be purchased from Fisher Scientific (Pittsburgh, Pa.).

Solid phase peptide synthesis may be carried out with an automatic peptide synthesizer (Model 430A, Applied Biosystems Inc., Foster City, Calif.) using the NMP/HOBt (Option 1) system and tBoc or Fmoc chemistry (see, Applied Biosystems User's Manual for the ABI 430A Peptide Synthesizer, Version 1.3B Jul. 1, 1988, section 6, pp. 49–70, Applied Biosystems, Inc., Foster City, Calif.) with capping. Boc-peptide-resins may be cleaved with HF (−50° C. to 0° C., 1 hour). The peptide may be extracted from the resin with alternating water and acetic acid, and the filtrates lyophilized. The Fmoc-peptide resins may be cleaved according to standard methods (*Introduction to Cleavage Techniques*, Applied Biosystems, Inc., 1990, pp. 6–12). Peptides may also be assembled using an Advanced Chem Tech Synthesizer (Model MPS 350, Louisville, Ky.).

Peptides may be purified by RP-HPLC (preparative and analytical) using a Waters Delta Prep 3000 system. A C4, C8 or C18 preparative column (10μ, 2.2×25 cm; Vydac, Hesperia, Calif.) may be used to isolate peptides, and purity may be determined using a C4, C8 or C18 analytical column (5 μ, 0.46×25 cm; Vydac). Solvents (A=0.1% TFA/water and B=0.1% TFA/CH$_3$CN) may be delivered to the analytical column at a flowrate of 1.0 ml/min and to the preparative column at 15 ml/min. Amino acid analyses may be performed on the Waters Pico Tag system and processed using the Maxima program. Peptides may be hydrolyzed by vapor-phase acid hydrolysis (115° C., 20–24 h). Hydrolysates may be derivatized and analyzed by standard methods (Cohen, et al., *The Pico Tag Method: A Manual of Advanced Techniques for Amino Acid Analysis*, pp. 11–52, Millipore Corporation, Milford, Mass. (1989)). Fast atom bombardment analysis may be carried out by M-Scan, Incorporated (West Chester, Pa.). Mass calibration may be performed using cesium iodide or cesium iodide/glycerol. Plasma desorption ionization analysis using time of flight detection may be carried out on an Applied Biosystems Bio-Ion 20 mass spectrometer. Electrospray mass spectroscopy may be carried and on a VG-Trio machine.

Peptide active ingredient compounds useful in the formulations and dosages of the invention may also be prepared using recombinant DNA techniques, using methods now known in the art. See, e.g., Sambrook et al., *Molecular Cloning: A Laboratory Manual*, 2d Ed., Cold Spring Harbor (1989). Alternatively, such compounds may be prepared by homogeneous phase peptide synthesis methods. Non-peptide compounds useful in the present invention may be prepared by art-known methods. For example, phosphate-containing amino acids and peptides containing such amino acids, may be prepared using methods known in the art. See. e.g., Bartlett and Landen, *Biog. Chem.* 14:356–377 (1986).

Conjugation of Polyethylene Glycol Polymers

There are several strategies for coupling PEG to peptides/proteins. See, Int. J. Hematology 68:1 (1998); Bioconjugate Chem. 6:150 (1995); and Crit. Rev. Therap. Drug Carrier Sys. 9:249 (1992) all of which are incorporated herein by reference in their entirety. Those skilled in the art, therefore, will be able to utilize such well-known techniques for linking one or more polethylene glycol polymers to the exendins and exendin agonists described herein. Suitable polethylene glycol polymers typically are commercially available or may be made by techniqueswell know to those skilled in the art. The polyethylene glycol polymers preferably have molecular weights between 500 and 20,000 and may be branched or straight chain polymers.

The attachment of a PEG on an intact peptide or protein can be accomplished by coupling to amino, carboxyl or thiol groups. These groups will typically be the N and C termini and on the side chains of such naturally occurring amino acids as lysine, aspartic acid, glutamic acid and cysteine. Since exendin 4 and other exendins and exendin agonists can be prepared by solid phase peptide chemistry techniques, a variety of moieties containing diamino and dicarboxylic groups with orthogonal protecting groups can be introduced for conjugation to PEG.

The present invention also provides for conjugation of an exendin or exendin agonist to one or more polymers other than polyethylene glycol which can regulate kidney clearance in a manner similar to polyethylene glycol. Examples of such polymers include albumin and gelatin. See, Gombotz and Pettit, *Bioconjugate Chem.*, 6:332–351, 1995, which is incorporated herein by reference in its entirety.

Utility

The formulations and dosages described herein are useful in view of their pharmacological properties. In particular, the compounds described herein possess activity as agents to reduce glucagon levels and suppress glucagon secretion, as evidenced by the ability to lower glucagon levels in animals and humans. They can be used to treat conditions or diseases that can be alleviated by reducing glucagon levels and suppressing glucagon secretion.

The compounds referenced above may form salts with various inorganic and organic acids and bases. Such salts include salts prepared with organic and inorganic acids, for example, HCl, HBr, $H_2SO_4$, $H_3PO_4$, trifluoroacetic acid, acetic acid, formic acid, methanesulfonic acid, toluenesulfonic acid, maleic acid, fumaric acid and camphorsulfonic acid. Salts prepared with bases include ammonium salts, alkali metal salts, e.g., sodium and potassium salts, and alkali earth salts, e.g., calcium and magnesium salts. Acetate, hydrochloride, and trifluoroacetate salts are preferred. The salts may be formed by conventional means, as by reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

Formulation and Administration

Modified exendin and exendin agonist formulations and dosages of the invention are useful in view of their exendin-like effects, and may conveniently be provided in the form of formulations suitable for parenteral (including intravenous, intramuscular and subcutaneous) administration. Also described herein are formulations and dosages useful in alternative delivery routes, including oral, nasal, buccal, sublingual and pulmonary.

The feasibility of alternate routes of delivery for exendin-4 has been explored by measuring exendin-4 in the circulation in conjunction with observation of a biologic response, such as plasma glucose lowering in diabetic animals, after administration. Passage of exendin-4 has been investigated across several surfaces, the respiratory tract (nasal, tracheal and pulmonary routes) and the gut (sublingual, gavage and intraduodenal routes). Biologic effect and appearance of exendin-4 in blood have been observed with each route of administration via the respiratory tract, and with sublingual and gavaged peptide via the gastrointestinal tract. Intra-tracheal administration, nasal administration, administration via the gut, and sublingual administration have all been described.

In some cases, it will be convenient to provide a modified exendin or exendin agonist and another anti-glucagon agent, such as an amylin or an amylin agonist, in a single composition or solution for administration together. In other cases, it may be more advantageous to administer another anti-glucagon agent separately from the exendin, exendin agonist, or modified exendin or exendin agonist. In yet other cases, it may be beneficial to provide an exendin, exendin agonist, or modified exendin or exendin agonist either co-formulated or separately with other glucagon lowering agents such as amylin. A suitable administration format may best be determined by a medical practitioner for each patient individually. Suitable pharmaceutically acceptable carriers and their formulation are described in standard formulation treatises, e.g., *Reminaton's Pharmaceutical Sciences* by E. W. Martin. See also Wang, Y. J. and Hanson, M. A. "Parenteral Formulations of Proteins and Peptides: Stability and Stabilizers," *Journal of Parenteral Science and Technology*, Technical Report No. 10, Supp. 42:2S (1988).

Compounds useful in the invention can be provided as parenteral compositions for injection or infusion. They can, for example, be suspended in an inert oil, suitably a vegetable oil such as sesame, peanut, olive oil, or other acceptable carrier. Preferably, they are suspended in an aqueous carrier, for example, in an isotonic buffer solution at a pH of about 5.6 to 7.4. These compositions may be sterilized by conventional sterilization techniques, or may be sterile filtered. The compositions may contain pharmaceutically acceptable auxiliary substances as required to approximate physiological conditions, such as pH buffering agents. Useful buffers include for example, sodium acetate/acetic acid buffers. A form of repository or "depot" slow release preparation may be used so that therapeutically effective amounts of the preparation are delivered into the bloodstream over many hours or days following transdermal injection or delivery.

The desired isotonicity may be accomplished using sodium chloride or other pharmaceutically acceptable agents such as dextrose, boric acid, sodium tartrate, propylene glycol, polyols (such as mannitol and sorbitol), or other inorganic or organic solutes. Sodium chloride is preferred particularly for buffers containing sodium ions.

The claimed compounds can also be formulated as pharmaceutically acceptable salts (e.g., acid addition salts) and/or complexes thereof. Pharmaceutically acceptable salts are non-toxic salts at the concentration at which they are administered. The preparation of such salts can facilitate the pharmacological use by altering the physical-chemical characteristics of the composition without preventing the composition from exerting its physiological effect. Examples of useful alterations in physical properties include lowering the melting point to facilitate transmucosal administration and increasing the solubility to facilitate the administration of higher concentrations of the drug.

Pharmaceutically acceptable salts include acid addition salts such as those containing sulfate, hydrochloride, phosphate, sulfamate, acetate, citrate, lactate, tartrate, methanesulfonate, ethanesulfonate, benzenesulfonate, p-toluenesulfonate, cyclohexylsulfamate and quinate. Pharmaceutically acceptable salts can be obtained from acids such as hydrochloric acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, and quinic acid. Such salts may be prepared by, for example, reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

Carriers or excipients can also be used to facilitate administration of the compound. Examples of carriers and excipients include calcium carbonate, calcium phosphate, various sugars such as lactose, glucose, or sucrose, or types of starch, cellulose derivatives, gelatin, vegetable oils, polyethylene glycols and physiologically compatible solvents. The compositions or pharmaceutical composition can be administered by different routes including intravenously, intraperitoneal, subcutaneous, and intramuscular, orally, topically, or transmucosally.

If desired, solutions of the above compositions may be thickened with a thickening agent such as methylcellulose. They may be prepared in emulsified form, either water in oil or oil in water. Any of a wide variety of pharmaceutically acceptable emulsifying agents may be employed including, for example, acacia powder, a non-ionic surfactant (such as a Tween), or an ionic surfactant (such as alkali polyether alcohol sulfates or sulfonates, e.g., a Triton).

Compositions useful in the invention are prepared by mixing the ingredients following generally accepted procedures. For example, the selected components may be simply mixed in a blender or other standard device to produce a concentrated mixture which may then be adjusted to the final concentration and viscosity by the addition of water or thickening agent and possibly a buffer to control pH or an additional solute to control tonicity.

For use by the physician, the compounds will be provided in dosage unit form containing an amount of an exendin, exendin agonist, or modified exendin or exendin agonist, with or without another anti-glucagon agent. Therapeutically effective amounts of an exendin, exendin agonist, or modified exendin or exendin agonist for use in the control of glucagon and in conditions in which glucagon levels are beneficially lowered or regulated are those that decrease post-prandial blood glucagon levels as desired. In diabetic or glucose intolerant individuals, plasma glucagon levels may be higher than in normal individuals. In such individuals, beneficial reduction or "smoothing" of post-prandial blood glucagon levels, may be obtained. As will be recognized by those in the field, an effective amount of therapeutic agent will vary with many factors including the age and weight of the patient, the patient's physical condition, the glucagon level or level of inhibition of glucagon suppression to be obtained, and other factors.

Such pharmaceutical compositions are useful in causing glucagon to be lowered in a subject and may be used as well in other disorders where lowered or suppressed glucagon is beneficial.

The effective daily anti-glucagon dose of the compounds will typically be in the range of 0.01 or 0.03 to about 5 mg/day, preferably about 0.01 or 0.5 to 2 mg/day and more preferably about 0.01 or 0.1 to 1 mg/day, for a 70 kg patient, administered in a single or divided doses. The exact dose to be administered is determined by the attending clinician and is dependent upon where the particular compound lies within the above quoted range, as well as upon the age, weight and condition of the individual. Administration should begin at the first sign of symptoms or shortly after diagnosis of, for example, diabetes mellitus as manifested by elevated glucagon. Administration may be by injection, preferably subcutaneous or intramuscular. Orally active compounds may be taken orally, however dosages should be increased 5–10 fold.

Generally, in treating or preventing elevated, inappropriate, or undesired post-prandial blood glucagon levels, the compounds of this invention may be administered to patients in need of such treatment in dosage ranges similar to those given above, however, the compounds are administered more frequently, for example, one, two, or three times a day. Particularly preferred are the exendin and exendin agonist formulations and dosages and routes of administration thereof described in commonly owned U.S. Provisional Application 60/116,380, entitled "Novel Exendin Agonist Formulations And Methods of Administration Thereof," filed Jan. 14, 1999 (and the corresponding PCT application claiming priority from it that was filed on Jan. 14, 2000, Serial No. PCT/US00/00902), and U.S. Provisional Application 60/175,365, entitled "Use of Exendins and Agonists Thereof for Modulation of Triglyceride Levels and Treatment of Dyslipidemia," filed Jan. 20, 2000, from which this application claims priority and the disclosures of which have been incorporated by reference in their entirety as if fully set forth herein.

The optimal formulation and mode of administration of compounds of the present application to a patient depend on factors known in the art such as the particular disease or disorder, the desired effect, and the type of patient. While the compounds will typically be used to treat human patients, they may also be used to treat similar or identical diseases in other vertebrates such as other primates, farm animals such as swine, cattle and poultry, and sports animals and pets such as horses, dogs and cats.

To assist in understanding the present invention the following Examples are included which describe the results of a series of experiments. The experiments relating to this invention should not, of course, be construed as specifically limiting the invention and such variations of the invention, now known or later developed, which would be within the purview of one skilled in the art are considered to fall within the scope of the invention as described herein and hereinafter claimed.

EXAMPLE 1

Preparation of Exendin-3

His Ser Asp Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala Pro Pro Pro Ser-MH$_2$ [SEQ. ID. NO: 1]

The above amidated peptide was assembled on 4-(2'-4-dimethoxyphenyl)-Fmoc aminomethyl phenoxy acetamide norleucine MBHA resin (Novabiochem, 0.55 mmole/g) using Fmoc-protected amino acids (Applied Biosystems, Inc.). In general, single-coupling cycles were used throughout the synthesis and Fast Moc (HBTU activation) chemistry was employed. Deprotection (Fmoc group removal) of the growing peptide chain was achieved using piperidine. Final deprotection of the completed peptide resin was achieved using a mixture of triethylsilane (0.2 mL), ethanedithiol (0.2 mL), anisole (0.2 mL), water (0.2 mL) and trifluoroacetic acid (15 mL) according to standard methods (Introduction to Cleavage Techniques, Applied Biosystems, Inc.) The peptide was precipitated in ether/water (50 mL) and centrifuged. The precipitate was reconstituted in glacial acetic acid and lyophilized. The lyophilized peptide was dissolved in water). Crude purity was about 75%.

Used in purification steps and analysis were Solvent A (0.1% TFA in water) and Solvent B (0.1% TFA in ACN).

The solution containing peptide was applied to a preparative C-18 column and purified (10% to 40% Solvent B in Solvent A over 40 minutes). Purity of fractions was determined isocratically using a C-18 analytical column. Pure fractions were pooled furnishing the above-identified peptide. Analytical reversed-phase high performance liquid chromatography (RP-HPLC) (gradient 30% to 60% Solvent B in Solvent A over 30 minutes) of the lyophilized peptide gave product peptide having an observed retention time of 19.2 minutes.

EXAMPLE 2

Preparation of Exendin-4

His Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala Pro Pro Pro Ser-NH$_2$ [SEQ. ID. NO: 2]

The above amidated peptide was assembled on 4-(2'-4'-dimethoxyphenyl)-Pmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Exendin-3 as describe in Example 1. Used in analysis were Solvent A (0.1% TFA in water) and Solvent B (0.1% TFA in ACN). Analytical RP-HPLC (gradient 36% to 46% solvent B in Solvent A over 30 minutes) of the lyophilized peptide gave product peptide having an observed retention time of 14.9 minutes. Electrospray Mass Spectrometry (M): calculated 4186.6; found 4186.0 to 4186.8 (four lots).

EXAMPLE 3

Clearance by the Kidney

The kidney can play a major role in the elimination of some molecules (drugs, peptides, proteins). For some molecules, this process begins when the kidney filters the blood at the glomerulus to produce the ultrafiltrate described below. The glomerular filter discriminates not only on the basis of molecular weight but also by acting as a negatively charged selective barrier, promoting retention of anionic compounds. The free fraction of molecules in the plasma (not protein bound) with a molecular weight less than 5 kD and an effective radii less than 15 Å are easily filtered. For larger molecular weight molecules they are filtered on a more restrictive and limited basis, principally by molecular size, structure and net charge. The cutoff point for glomerular filtration lies between albumin (67 kD) which is retained and hemoglobin (68 kD) which is filtered. Albumin, with an effective radius of about 36 Å is filtered less than 1% at the glomerulus.

Once in the glomerulus a molecule travels to the proximal tubule where it is either reabsorbed or it passes on through the loop of Henle to the distal tubule where collecting ducts drain the filtrate into the bladder. Filtered proteins and peptides are typically cleaved by brush border enzymes in the proximal tubule, from where they are efficiently retrieved by sodium/amino cotransporters (scavenging pumps) Otherwise, molecules which are polar, ionized and of large molecular weight will not be reabsorbed. Throughout this process metabolizing enzymes in the renal cortex (proximal tubules) may also degrade the molecule into more polar molecules, thereby increasing the probability for excretion into the urine. Many peptide hormones (for example, amylin, calcitonins) are degraded by passage through the renal circulation, presumably by vascular ectoenzymes accessible to the plasma, independently of the process of glomerular filtration. In those examples, rates of peptide clearance from the plasma are similar to the rate of renal plasma flow, which is ~3-fold greater than the rate of glomerular filtration.

Studies performed to identify plasma circulating metabolites of exendin-4 yielded very little evidence of proteolytic degradation; following large intravenous doses in animals, HPLC analysis of plasma showed only the presence of intact exendin, and negligible appearance of "daughter" peaks indicative of the buildup of degradation products. This is in contrast to other peptides studied (for example amylin and GLP-1) where the disappearance of the "parent" HPLC peak was associated with the appearance of "daughter" HPLC peaks, subsequently identified as subpeptide degradants. The absence of plasma degradants of exendin indicates little or no proteolysis at any site, including the renal circulation. Any clearance by the kidney, then, is via non-proteolytic means, namely filtration or active excretion (as occurs with para-amino hippurate).

Figure 6:
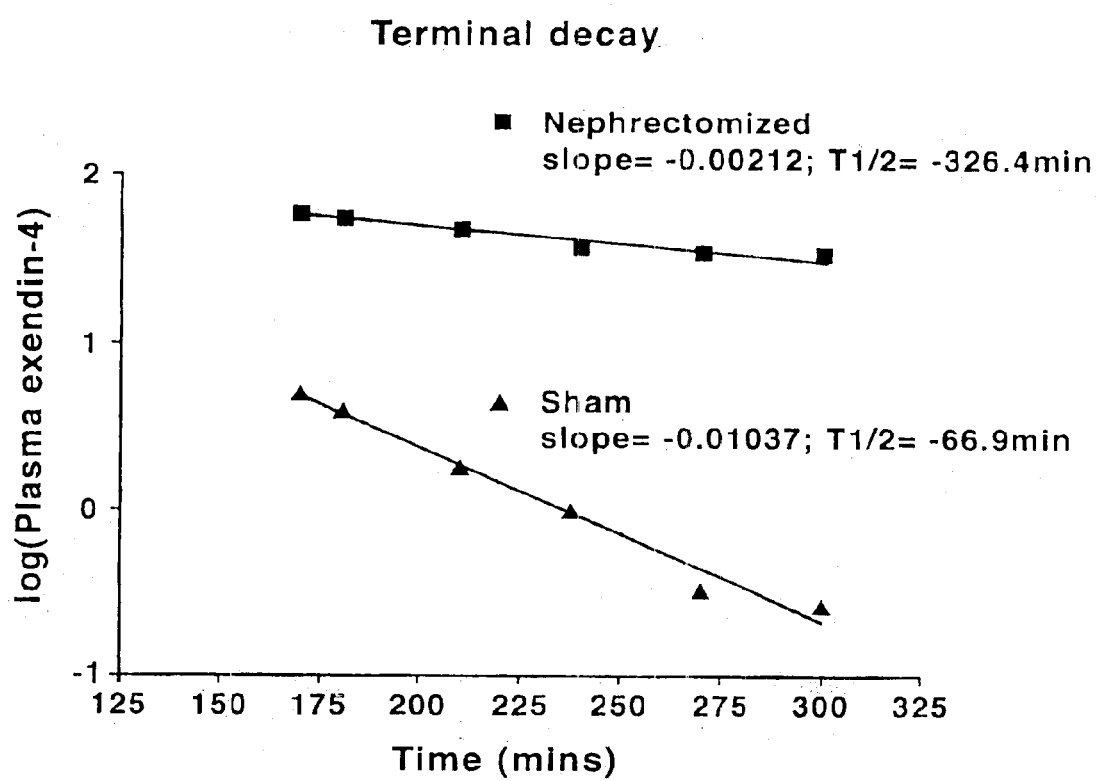
FIG. 6 is a graph showing the terminal decay of exendin-4 plasma levels in nephrectomized and sham subjects.

Initial measurements of exendin clearance in man (120–130 mL/min), monkeys (~9 mL/min) and rats (3.2–4.4 mL/min) matched reported glomerular filtration rates in those species. To test whether renal filtration could be the principal mode of exendin elimination, studies were performed in overnight fasted nephrectomized male rats infused with exendin at a constant rate. Steady-state plasma levels of exendin-4 were greatly increased in nephrectomized rats compared to rats with their kidneys intact. This data indicated that the kidney was responsible for at least 80% of the clearance of exendin 4 (see FIGS. 5 and 6). Exendin clearance rates in intact rats were, again, similar to glomerular filtration rates expected in those rats (4.2 mL/min). Taken together these results indicate that very little metabolism occurs systemically and that most of the clearance of exendin 4 is through the kidney via filtration (but not by renal intravascular proteolysis). The low amounts of immunoreactive full-length exendin in the urine are consistent with it being cleaved by brush border enzymes in the proximal tubule after filtration.

EXAMPLE 4

Exendin-4 Decreases Glucagon Secretion During Hyperglycemic Clamps in Diabetic Fatty Zucker Rats Absolute or relative hyperglucagonemia is often a feature of, for example, type 1 and type 2 diabetes mellitus, and the suppression of excessive glucagon secretion in these and other conditions described or referred to herein is a potential benefit of therapy using glucagonostatic agents. In this Example, the effect of exendin-4 on glucagon secretion in male anaesthetized Diabetic Fatty Zucker (ZDF) rats was examined. Using an hyperinsulinemic hyperglycemic clamp protocol, factors tending to influence glucagon secretion were held constant. Plasma glucose was clamped at ~34 mM 60 min before beginning intravenous infusions of saline (n=7) or exendin-4 (0.2 µg+2.1µg/mL/h; n=7). Plasma glucagon concentration measured prior to these infusions were similar in both groups (306±30 pM versus 252±32 pM, respectively; n.s.).

Mean plasma glucagon concentration in exendin-4 infused rats was nearly half of that in saline-infused rats in the final 60 minutes of the clamp (165±18 pM versus 298±26 pM, respectively; P<0.002). The hyperglycemic clamp protocol also enabled measurement of insulin sensitivity. Glucose infusion rate during the clamp was increased by 111±7% in exendin-4-treated versus control rats (P<0.001). In other words, exendin-4 exhibited a glucagonostatic effect in ZDF rats during hyperglycemic clamp studies, an effect that will be of therapeutic benefit in diabetic humans.

EXAMPLE 5

Metabolic Effects of Exedin-4 on Glucagon Secretion in People with Type 2 Diabetes In this Example, the safety, tolerability, and efficacy of synthetic exendin-4 was evaluated in 8 male non-insulin using patients with type 2 diabetes who had discontinued other antidiabetic therapy for a minimum of 7 days. Each patient received subcutaneous (SC) injections of placebo (PBO) and 0.1, 0.2, and 0.3 µg/kg exendin-4 48 hours apart in a single-blind, dose-rising, placebo controlled crossover design. Five patients also received a 0.4 µg/kg dose. Plasma glucose, insulin and glucagon concentrations were assessed fasting and in response to a 7 Kcal/kg Sustacal® challenge administered at the time of exendin-4/PBO injection. Gastric emptying was evaluated by measuring serum acetaminophen concentrations following a 20 mg/kg oral dose of liquid acetaminophen administered with the Sustacal®. No safety issues were identified based upon reported adverse events, EKG and safety lab monitoring. Doses of 0.3 and 0.4 µg/kg elicited a dose-dependent increase in nausea; vomiting occurred at the highest dose.

Plasma glucose concentrations were reduced in all doses of exendin-4 compared to PBO although insulin concentrations were not significantly different. The 8 hour mean±SE changes in plasma glucose AUC from baseline were +391±187, −263±108, −247±64, −336±139, and −328±70 mg*hr/dL for the PBO, 0.1, 0.2, 0.3, and 0.4 µg/kg doses respectively. The 3 hr changes in plasma glucagon were +128.0±19.2, −5.6±10.5, −29.4±18.6, −40.5±24.5, and +6.9±38.6 pg*hr/mL respectively. The gastric emptying rate was slowed in all doses and the mean total absorbed acetaminophen over 6 hours was reduced by 51%, 50%, 57% and 79% compared to PBO for 0.1, 0.2, 0.3, and 0.4 µg/kg doses respectively. In summary, SC injection of exendin-4 to patients identified no safety issues, was tolerated at doses ≦0.3 µg/kg, reduced plasma glucose and glucagon and slowed the rate of gastric emptying. These observations support the use of exendin for the treatment of conditions that would benefit from reduced glucagon levels and/or suppression of glucagon, including but not limited to type 1 and type 2 diabetes.

EXAMPLE 6

PEG Modified Exendin 4

In the case of exendin 4, a 39 amino acid peptide with a molecular weight of 4187, modifications that increase its size and/or increase its anionic nature will decrease its ability to be filtered by the kidney. Because clearance of exendin 4 is largely by the kidney this will effectively increase its half life. Other properties of PEGylation (increased plasma half-life due to evasion of such renal and/or cellular clearance mechanisms that may exist; reduced immunogenicity and antigenicity; increased solubility; resistance to proteolysis; reduced toxicity (avoid dose spike); improved thermal and mechanical stability; improved permeability of the mucus or epithelial layer; and selective control over a specific biological function) are also of potential benefit for exendin 4 and exendin agonists.

In particular, because we have observed multiple pharmacologies (likely representing multiple receptor subtypes), different spectra of biological activities of exendin 4 may be selected by putting a PEG group at appropriate positions. Loss or alteration of bioactivity has been reported for PEGylated proteins which may be due to the presence of the PEG chains themselves, the particular site occupied by the PEG chain, or the coupling conditions having an adverse effect on the protein.

Primary considerations for PEG modification in terms of filtration at the kidney of exendin and exendin agonists are size and charge. Unmodified, exendin 4 has a molecular weight of approximately 4.2 kD and is anionic in nature with an overall net charge of approximately −2 at physiological pH. One, two or three PEG constituents may be covalently linked to exendin 4 or an analog of exendin 4, for example, with one PEG constituent being preferred. The size of the PEG can vary from a molecular weight of 500 to 20,000, preferably between 5,000 and 12,000.

Many of the methods for covalent attachment of PEG take advantage of the epsilon-amino group on lysine. Exendin 4 has two lysines that can be modified by attachment of PEG. An alanine scan of AC3177 (Leu$^{14}$, Phe$^{25}$1–28 exendin-4), a shortened analog of exendin 4, revealed positions that are sensitive to substitution by alanine. The two lysines at positions 12 and 27 were moderately affected by this substitution suggesting that loss of the lysine specific R group side chain (methylene chain plus epsilon-amino group) is tolerated. With regard to the full-length peptide, exendin 4, the two lysine positions are appropriate for PEG attachment (see compounds 201 and 202). In addition, depending on the chemistry used to conjugate the PEG, the epsilon-amino groups at these positions may be masked thereby increasing the anionic nature of the peptide.

(201) HGEGTFTSDLSK(PEG)QMEEEAVRLFIEWLKNGGPSSGAPPPS-NH$_2$ [SEQ. ID. NO. 223]

(202) HGEGTFTSDLSKQMEEEAVRLFIEWLK(PEG)NGGPSSGAPPPS-NH$_2$ [SEQ. ID. NO. 224].

Based on the results of the alanine scan, other likely positions that may be modified by insertion of a Lys-PEG or equivalent, for example, are:

(203) HK(PEG)EGTFTSDLSKQMEEEAVRLFIEWLKNGGPSSGAPPPS-NH$_2$ [SEQ. ID. NO. 225]

(204) HGEGK(PEG)FTSDLSKQMEEEAVRLFIEWLKNGGPSSGAPPPS-NH$_2$ [SEQ. ID. NO. 226]

(205) HGEGTFTK(PEG)DLSKQMEEEAVRLFIEWLKNGGPSSGAPPPS-NH$_2$ [SEQ. ID. NO. 227]

(206) HGEGTFTSDK(PEG)SKQMEEEAVRLFIEWLKNGGPSSGAPPPS-NH$_2$ [SEQ. ID. NO. 228]
(207) HGEGTFTSDLK(PEG)KQMEEEAVRLFIEWLKNGGPSSGAPPPS-NH$_2$ [SEQ. ID. NO. 229]
(208) HGEGTFTSDLSKK(PEG)MEEEAVRLFIEWLKNGGPSSGAPPPS-NH$_2$ [SEQ. ID. NO. 230]
(209)*HGEGTFTSDLSKQMEK(PEG)EAVRLFIEWLKNGGPSSGAPPPS-NH$_2$ [SEQ. ID. NO. 231]
(210)*HGEGTFTSDLSKQMEEK(PEG)AVRLFIEWLKNGGPSSGAPPPS-NH$_2$ [SEQ. ID. NO. 232]
(211) HGEGTFTSDLSKQMEEEAK(PEG)RLFIEWLKNGGPSSGAPPPS-NH$_2$ [SEQ. ID. NO. 233]
(212) HGEGTFTSDLSKQMEEEAVRK(PEG)FIEWLKNGGPSSGAPPPS-NH$_2$ [SEQ. ID. NO. 234]
(213)*HGEGTFTSDLSKQMEEEAVRLFIK(PEG)WLKNGGPSSGAPPPS-NH$_2$ [SEQ. ID. NO. 235]
(214) HGEGTFTSDLSKQMEEEAVRLFIEK(PEG)LKNGGPSSGAPPPS-NH$_2$ [SEQ. ID. NO. 236]
(215) HGEGTFTSDLSKQMEEEAVRLFIEWLKK(PEG)GGPSSGAPPPS-NH$_2$ [SEQ. ID. NO. 237].

The three positions* above normally containing a glutamic acid that were indicated for modification with K(PEG) can also be modified by conjugation to the glutamic acid side chain carboxyl group, E(PEG).

Another analog in which the Lys-PEG can be added is at the supposed GlyGly turn:
(216) HGEGTFTSDLSKQMEEEAVRLFIEWLKNK(PEG)GPSSGAPPPS-NH$_2$[SEQ. ID. NO. 238]
(217) HGEGTFTSDLSKQMEEEAVRLFIEWLKNGK(PEG)PSSGAPPPS-NH$_2$ [SEQ. ID. NO. 239].

Positions 29–39 of exendin-4 may not be critical for the glucose lowering activity as evidenced by AC3177 having nearly equipotent activity to exendin 4, and any of them, alone or in combination, can be substituted for K(PEG) or an equivalent.

One skilled in the art would readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims.

It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations, which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims.

What is claimed is:

1. A method of lowering plasma glucagon in a subject in need thereof, comprising:
   identifying a subject in need of therapeutic lowering of plasma glucagon levels; and
   administering to said subject a composition comprising a therapeutically effective glucagon lowering amount of an exendin, an exendin analog or combinations thereof;
   wherein said exendin and exendin analog each have amino acid sequence that is more than 30 amino acid residues in length.

2. The method of claim 1, wherein said subject is suffering from nocrolytic migratory erythema.

3. The method of claim 1, wherein said subject has a glucagonoma.

4. The method of claim 1, wherein the subject has a diabetes-related disorder.

5. The method of claim 4, wherein the subject has type 2 diabetes.

6. The method of any of claims 1–5, wherein said subject is a human.

7. The method of claim 1, wherein said composition is provided in a dosage unit form and further comprises another anti-glucagon agent.

8. The method of claim 1, wherein said composition comprises an exendin analog having an amino acid sequence selected from the sequences of SEQ ID NO: 47 and SEQ ID NO: 48.

9. The method of claim 8, wherein said amino acid sequence has a sequence of SEQ ID NO: 47, wherein the Xaa in position 1 is His; the Xaa in position 2 is Gly, the Xaa in position 6 is Phe or naphthylalanine; the Xaa in position 14 is Leu, pentylglycine or Met; the Xaa in position 22 is Phe or naphthylalanine; the Xaa in position 23 is Ile or Val; the Xaa in position 25 is Phe, Tyr, or naphthylalanine; the Xaa in positions 31, 36, 37, and 38 are independently selected from Pro, homoproline, thioproline, and N-alkylalanine; and the Xaa in position 39 is Ser or Tyr.

10. The method of claim 8, wherein said amino acid sequence has a sequence of SEQ ID NO: 47, wherein the Xaa in position 14 is Leu or pentylglycine; and the Xaa in position 22 is Phe or naphthylalanine.

11. The method of claim 8, wherein said amino acid sequence has a sequence of SEQ ID NO: 48, wherein the Xaa in positions 6 and 22 are independently selected from Phe and naphthylalanine; the Xaa in position 23 is Ile or Val; and the Xaa in positions 30, 36, 37, and 38 are independently selected from Pro, homoproline, thioproline, and N-alkylalanine.

12. The method of claim 1, wherein said composition comprises exendin-4.

13. A method of lowering plasma glucagon in a subject, comprising:

identifying a subject in need of therapeutic lowering of plasma glucagon levels; and administering to said subject a composition consisting essentially of a therapeutically glucagon lowering amount of an exendin, an exendin analog or combinations thereof;

wherein said exendin and exendin analog each have an amino acid sequence that is more than 30 amino acid residues in length.

14. The method of claim 13, wherein said subject is suffering from necrolytic migratory erythema.

15. The method of claim 13, wherein said subject has a glucaganoma.

16. The method of claim 13, wherein said composition consists essentially of exendin-4.

17. The method of claim 7, wherein said anti-glucagon agent comprises amylin.

18. The method of claim 13, wherein the subject has a diabetes-related disorder.

19. The method of claim 18, wherein the subject has type 2 diabetes.

20. The method of any of claims 13–19, wherein said subject is a human.

21. The method of claim 13, wherein said composition consists essentially of an exendin analog having an amino acid sequence selected from the sequences of SEQ ID NO: 47 and SEQ ID NO: 48.

22. The method of claim 21, wherein said amino acid sequence has a sequence of SEQ ID NO: 47, wherein the Xaa in position 1 is His; the Xaa in position 2 is Gly; the Xaa in position 6 is Phe or naphthylalanine; the Xaa in position 14 is Leu, pentylglycine or Met; the Xaa in position 22 is Phe or naphthylalanine; the Xaa in position 23 is Ile or Val; the Xaa in position 25 is Phe, Tyr, or naphthylalanine; the Xaa in positions 31, 36, 37, and 38 are independently selected from Pro, homoproline, thioproline, and N-alkylalanine; and the Xaa in position 39 is Ser or Tyr.

23. The method of claim 21, wherein said amino acid sequence has a sequence of SEQ ID NO: 47, wherein the Xaa in position 14 is Leu pentylglycine, and the Xaa in position 22 is Phe or naphthylalanine.

24. The method of claim 21, wherein said amino acid sequence has a sequence of SEQ ID NO: 48, wherein the Xaa in positions 6 and 22 are independently selected from Phe and naphthylalanine; the Xaa in position 23 is Ile or Val; and the Xaa in positions 30, 36, 37, and 38 are independently selected from Pro, homoproline, thioproline, and N-alkylalanine.

* * * * *

SEQUENCE LISTING

<160> NUMBER OF SEQ ID NOS: 239

<210> SEQ ID NO 1
<211> LENGTH: 39
<212> TYPE: PRT
<213> ORGANISM: Heloderma Horridum
<220> FEATURE:
<221> NAME/KEY: AMIDATION
<222> LOCATION: (39)
<223> OTHER INFORMATION: Ser in position 39 is amidated

<400> SEQUENCE: 1

His Ser Asp Gly Thr Phe Thr Ser Asp Leu Ser Lys Gln Met Glu Glu
 1               5                  10                  15

```
Glu Ala Val Arg Leu Phe Ile Glu Trp Leu Lys Asn Gly Gly Pro Ser
            20                  25                  30

Ser Gly Ala Pro Pro Pro Ser
            35
```

<210> SEQ ID NO 2
<211> LENGTH: 39
<212> TYPE: PRT
<213> ORGANISM: Heloderma Suspectum
<220> FEATURE:
<221> NAME/KEY: AMIDATION
<222> LOCATION: (39)
<223> OTHER INFORMATION: Ser in position 39 is amidated

<400> SEQUENCE: 2

```
His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
            35
```

<210> SEQ ID NO 3
<211> LENGTH: 30
<212> TYPE: PRT
<213> ORGANISM: Artificial Sequence
<220> FEATURE:
<223> OTHER INFORMATION: Description of Artificial Sequence: Synthetic
      Amino Acid Sequence

<400> SEQUENCE: 3

```
His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly
            20                  25                  30
```

<210> SEQ ID NO 4
<211> LENGTH: 30
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (30)
<223> OTHER INFORMATION: Gly in position 30 is amidated

<400> SEQUENCE: 4

```
His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly
            20                  25                  30
```

<210> SEQ ID NO 5
<211> LENGTH: 30
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: MOD_RES
<222> LOCATION: (30)
<223> OTHER INFORMATION: AMIDATION, Position 30 is Gly-NH2

-continued

```
<400> SEQUENCE: 5

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly
            20                  25                  30

<210> SEQ ID NO 6
<211> LENGTH: 28
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: MOD_RES
<222> LOCATION: (28)
<223> OTHER INFORMATION: AMIDATION, Position 28 is Asn-NH2

<400> SEQUENCE: 6

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn
            20                  25

<210> SEQ ID NO 7
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: MOD_RES
<222> LOCATION: (30)
<223> OTHER INFORMATION: AMIDATION, Position 30 is Gly-NH2

<400> SEQUENCE: 7

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly Pro Ser
            20                  25                  30

Ser Gly Ala Pro Pro Pro Ser
        35

<210> SEQ ID NO 8
<211> LENGTH: 28
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: MOD_RES
<222> LOCATION: (28)
<223> OTHER INFORMATION: AMIDATION, Position 28 is Asn-NH2

<400> SEQUENCE: 8

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn
            20                  25

<210> SEQ ID NO 9
<211> LENGTH: 28
<212> TYPE: PRT
<213> ORGANISM: Artificial Sequence
```

```
<220> FEATURE:
<223> OTHER INFORMATION: Description of Artificial Sequence: Synthetic
      Construct
<220> FEATURE:
<221> NAME/KEY: MOD_RES
<222> LOCATION: (28)
<223> OTHER INFORMATION: AMIDATION, Position 28 is Asn-NH2

<400> SEQUENCE: 9

His Gly Glu Gly Thr Phe Thr Ser Asp Leu Ser Lys Gln Leu Glu Glu
 1               5                  10                  15

Ala Val Arg Leu Ala Ile Glu Phe Leu Lys Asn
            20                  25

<210> SEQ ID NO 10
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: MOD_RES
<222> LOCATION: (39)
<223> OTHER INFORMATION: AMIDATION, Position 39 is Ser-NH2

<400> SEQUENCE: 10

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly Pro Ser
            20                  25                  30

Ser Gly Ala Pro Pro Pro Ser
            35

<210> SEQ ID NO 11
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: MOD_RES
<222> LOCATION: (39)
<223> OTHER INFORMATION: AMIDATION, Position 39 is Ser-NH2

<400> SEQUENCE: 11

His Gly Glu Gly Thr Phe Thr Ser Asp Leu Ser Lys Gln Leu Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
            35

<210> SEQ ID NO 12
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: MOD_RES
<222> LOCATION: (39)
<223> OTHER INFORMATION: AMIDATION, Position 39 is Ser-NH2

<400> SEQUENCE: 12
```

His Gly Glu Gly Thr Phe Thr Ser Asp Leu Ser Lys Gln Met Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Pro Ser
        35

<210> SEQ ID NO 13
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: MOD_RES
<222> LOCATION: (39)
<223> OTHER INFORMATION: AMIDATION, Position 39 is Ser-NH2

<400> SEQUENCE: 13

Tyr Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 14
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: MOD_RES
<222> LOCATION: (39)
<223> OTHER INFORMATION: AMIDATION, Position 39 is Tyr-NH2

<400> SEQUENCE: 14

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Tyr
        35

<210> SEQ ID NO 15
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: MOD_RES
<222> LOCATION: (39)
<223> OTHER INFORMATION: AMIDATION, Position 39 is Ser-NH2

<400> SEQUENCE: 15

His Gly Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser

<210> SEQ ID NO 16
<211> LENGTH: 39
<212> TYPE: PRT
<213> ORGANISM: Artificial Sequence
<220> FEATURE:
<223> OTHER INFORMATION: Description of Artificial Sequence: Synthetic Construct
<220> FEATURE:
<221> NAME/KEY: VARIANT
<222> LOCATION: (6)
<223> OTHER INFORMATION: Xaa is naphthylalanine
<220> FEATURE:
<221> NAME/KEY: MOD_RES
<222> LOCATION: (39)
<223> OTHER INFORMATION: AMIDATION, Position 39 is Ser-NH2

<400> SEQUENCE: 16

His Gly Glu Gly Thr Xaa Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 17
<211> LENGTH: 39
<212> TYPE: PRT
<213> ORGANISM: Artificial Sequence
<220> FEATURE:
<223> OTHER INFORMATION: Description of Artificial Sequence: Synthetic Construct
<220> FEATURE:
<221> NAME/KEY: MOD_RES
<222> LOCATION: (39)
<223> OTHER INFORMATION: AMIDATION, Position 39 is Ser-NH2

<400> SEQUENCE: 17

His Gly Glu Gly Thr Phe Ser Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 18
<211> LENGTH: 39
<212> TYPE: PRT
<213> ORGANISM: Artificial Sequence
<220> FEATURE:
<223> OTHER INFORMATION: Description of Artificial Sequence: Synthetic Construct
<220> FEATURE:
<221> NAME/KEY: MOD_RES
<222> LOCATION: (39)
<223> OTHER INFORMATION: AMIDATION, Position 39 is Ser-NH2

<400> SEQUENCE: 18

His Gly Glu Gly Thr Phe Ser Thr Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35

```
<210> SEQ ID NO 19
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: MOD_RES
<222> LOCATION: (39)
<223> OTHER INFORMATION: AMIDATION, Position 39 is Ser-NH2

<400> SEQUENCE: 19

His Gly Glu Gly Thr Phe Thr Thr Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 20
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: MOD_RES
<222> LOCATION: (39)
<223> OTHER INFORMATION: AMIDATION, Position 39 is Ser-NH2

<400> SEQUENCE: 20

His Gly Glu Gly Thr Phe Thr Ser Glu Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 21
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: MOD_RES
<222> LOCATION: (39)
<223> OTHER INFORMATION: AMIDATION, Position 39 is Ser-NH2
<220> FEATURE:
<221> NAME/KEY: VARIANT
<222> LOCATION: (10)
<223> OTHER INFORMATION: Xaa is pentylglycine

<400> SEQUENCE: 21

His Gly Glu Gly Thr Phe Thr Ser Asp Xaa Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 22
<211> LENGTH: 39
<212> TYPE: PRT
```

```
<213> ORGANISM: Artificial Sequence
<220> FEATURE:
<223> OTHER INFORMATION: Description of Artificial Sequence: Synthetic
      Construct
<220> FEATURE:
<221> NAME/KEY: MOD_RES
<222> LOCATION: (39)
<223> OTHER INFORMATION: AMIDATION, Position 39 is Ser-NH2
<220> FEATURE:
<221> NAME/KEY: VARIANT
<222> LOCATION: (10)
<223> OTHER INFORMATION: Xaa is pentylglycine

<400> SEQUENCE: 22

His Gly Glu Gly Thr Phe Thr Ser Asp Xaa Ser Lys Gln Leu Glu
 1               5                  10                  15

Glu Ala Val Arg Leu Phe Ile Glu Phe Leu Lys Asn Gly Gly Pro Ser
            20                  25                  30

Ser Gly Ala Pro Pro Pro Ser
        35

<210> SEQ ID NO 23
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: MOD_RES
<222> LOCATION: (39)
<223> OTHER INFORMATION: AMIDATION, Position 39 is Ser-NH2
<220> FEATURE:
<221> NAME/KEY: VARIANT
<222> LOCATION: (14)
<223> OTHER INFORMATION: Xaa is pentylglycine

<400> SEQUENCE: 23

His Gly Glu Gly Thr Phe Thr Ser Asp Leu Ser Lys Gln Xaa Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 24
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: VARIANT
<222> LOCATION: (14)
<223> OTHER INFORMATION: Xaa is pentylglycine

<400> SEQUENCE: 24

His Gly Glu Gly Thr Phe Thr Ser Asp Leu Ser Lys Gln Xaa Glu Glu
 1               5                  10                  15

Glu Ala Val Arg Leu Phe Ile Glu Phe Leu Lys Asn Gly Gly Pro Ser
            20                  25                  30

Ser Gly Ala Pro Pro Pro Ser
        35

<210> SEQ ID NO 25
<211> LENGTH: 39
```

```
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: MOD_RES
<222> LOCATION: (39)
<223> OTHER INFORMATION: AMIDATION, Postion 39 is Ser-NH2
<220> FEATURE:
<221> NAME/KEY: VARIANT
<222> LOCATION: (22)
<223> OTHER INFORMATION: Xaa is napthylalanine

<400> SEQUENCE: 25

His Gly Glu Gly Thr Phe Thr Ser Asp Leu Ser Lys Gln Met Glu Glu
 1               5                  10                  15

Glu Ala Val Arg Leu Xaa Ile Glu Trp Leu Lys Asn Gly Gly Pro Ser
            20                  25                  30

Ser Gly Ala Pro Pro Pro Ser
        35

<210> SEQ ID NO 26
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: MOD_RES
<222> LOCATION: (39)
<223> OTHER INFORMATION: AMIDATION, Position 39 is Ser-NH2

<400> SEQUENCE: 26

His Gly Glu Gly Thr Phe Thr Ser Asp Leu Ser Lys Gln Met Glu Glu
 1               5                  10                  15

Glu Ala Val Arg Leu Phe Val Glu Trp Leu Lys Asn Gly Gly Pro Ser
            20                  25                  30

Ser Gly Ala Pro Pro Pro Ser
        35

<210> SEQ ID NO 27
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: MOD_RES
<222> LOCATION: (39)
<223> OTHER INFORMATION: AMIDATION, Position 39 is Ser-NH2

<400> SEQUENCE: 27

His Gly Glu Gly Thr Phe Thr Ser Asp Leu Ser Lys Gln Leu Glu Glu
 1               5                  10                  15

Glu Ala Val Arg Leu Phe Val Glu Phe Leu Lys Asn Gly Gly Pro Ser
            20                  25                  30

Ser Gly Ala Pro Pro Pro Ser
        35

<210> SEQ ID NO 28
<211> LENGTH: 39
<212> TYPE: PRT
<213> ORGANISM: Artificial Sequence
<220> FEATURE:
```

```
<223> OTHER INFORMATION: Description of Artificial Sequence: Synthetic
      Construct
<220> FEATURE:
<221> NAME/KEY: MOD_RES
<222> LOCATION: (39)
<223> OTHER INFORMATION: AMIDATION, Position 39 is Ser-NH2

<400> SEQUENCE: 28

His Gly Glu Gly Thr Phe Thr Ser Asp Leu Ser Lys Gln Leu Glu Glu
 1               5                  10                  15

Glu Ala Val Arg Leu Phe Val Glu Phe Leu Lys Asn Gly Gly Pro Ser
            20                  25                  30

Ser Gly Ala Pro Pro Pro Ser
        35

<210> SEQ ID NO 29
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: VARIANT
<222> LOCATION: (23)
<223> OTHER INFORMATION: Xaa at position 23 is tertiary-butylglycine
<220> FEATURE:
<221> NAME/KEY: MOD_RES
<222> LOCATION: (39)
<223> OTHER INFORMATION: AMIDATION, Position 39 is Ser-NH2

<400> SEQUENCE: 29

His Gly Glu Gly Thr Phe Thr Ser Asp Leu Ser Lys Gln Leu Glu Glu
 1               5                  10                  15

Glu Ala Val Arg Leu Phe Xaa Glu Phe Leu Lys Asn Gly Gly Pro Ser
            20                  25                  30

Ser Gly Ala Pro Pro Pro Ser
        35

<210> SEQ ID NO 30
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: MOD_RES
<222> LOCATION: (39)
<223> OTHER INFORMATION: AMIDATION, Position 39 is Ser-NH2

<400> SEQUENCE: 30

His Gly Glu Gly Thr Phe Thr Ser Asp Leu Ser Lys Gln Met Glu Glu
 1               5                  10                  15

Glu Ala Val Arg Leu Phe Ile Asp Trp Leu Lys Asn Gly Gly Pro Ser
            20                  25                  30

Ser Gly Ala Pro Pro Pro Ser
        35

<210> SEQ ID NO 31
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
```

```
<221> NAME/KEY: MOD_RES
<222> LOCATION: (39)
<223> OTHER INFORMATION: AMIDATION, Position 39 is Ser-NH2

<400> SEQUENCE: 31

His Ala Glu Gly Thr Phe Thr Ser Asp Leu Ser Lys Gln Leu Glu Glu
  1               5                  10                  15

Glu Ala Val Arg Leu Phe Ile Glu Phe Leu Lys Asn Gly Gly Pro Ser
             20                  25                  30

Ser Gly Ala Pro Pro Pro Ser
            35

<210> SEQ ID NO 32
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: VARIANT
<222> LOCATION: (31)
<223> OTHER INFORMATION: Xaa at position 31 is thioproline
<220> FEATURE:
<221> NAME/KEY: VARIANT
<222> LOCATION: (36)..(38)
<223> OTHER INFORMATION: Xaa at positions 36,37 and 38 is thioproline
<220> FEATURE:
<221> NAME/KEY: MOD_RES
<222> LOCATION: (39)
<223> OTHER INFORMATION: AMIDATION, Position 39 is Ser-NH2

<400> SEQUENCE: 32

His Gly Glu Gly Thr Phe Thr Ser Asp Leu Ser Lys Gln Met Glu Glu
  1               5                  10                  15

Glu Ala Val Arg Leu Phe Ile Glu Trp Leu Lys Asn Gly Gly Xaa Ser
             20                  25                  30

Ser Gly Ala Xaa Xaa Xaa Ser
            35

<210> SEQ ID NO 33
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: VARIANT
<222> LOCATION: (36)..(38)
<223> OTHER INFORMATION: Xaa at positions 36, 37, and 38 is thioproline
<220> FEATURE:
<221> NAME/KEY: MOD_RES
<222> LOCATION: (39)
<223> OTHER INFORMATION: AMIDATION, Position 39 is Ser-NH2

<400> SEQUENCE: 33

His Gly Glu Gly Thr Phe Thr Ser Asp Leu Ser Lys Gln Met Glu Glu
  1               5                  10                  15

Glu Ala Val Arg Leu Phe Ile Glu Trp Leu Lys Asn Gly Gly Pro Ser
             20                  25                  30

Ser Gly Ala Xaa Xaa Xaa Ser
            35

<210> SEQ ID NO 34
<211> LENGTH: 39
<212> TYPE: PRT
```

```
<213> ORGANISM: Artificial Sequence
<220> FEATURE:
<223> OTHER INFORMATION: Description of Artificial Sequence: Synthetic
      Construct
<220> FEATURE:
<221> NAME/KEY: VARIANT
<222> LOCATION: (31)
<223> OTHER INFORMATION: Xaa at position 31 is homoproline
<220> FEATURE:
<221> NAME/KEY: VARIANT
<222> LOCATION: (36)..(38)
<223> OTHER INFORMATION: Xaa at positions 36, 37, and 38 is homoproline
<220> FEATURE:
<221> NAME/KEY: MOD_RES
<222> LOCATION: (39)
<223> OTHER INFORMATION: AMIDATION, Position 39 is Ser-NH2

<400> SEQUENCE: 34

His Gly Glu Gly Thr Phe Thr Ser Asp Leu Ser Lys Gln Met Glu Glu
  1               5                  10                  15

Glu Ala Val Arg Leu Phe Ile Glu Trp Leu Lys Asn Gly Gly Xaa Ser
             20                  25                  30

Ser Gly Ala Xaa Xaa Xaa Ser
          35

<210> SEQ ID NO 35
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: VARIANT
<222> LOCATION: (36)..(38)
<223> OTHER INFORMATION: Xaa at positions 36, 37, and 38 is homoproline
<220> FEATURE:
<221> NAME/KEY: MOD_RES
<222> LOCATION: (39)
<223> OTHER INFORMATION: AMIDATION, Position 39 is Ser-NH2

<400> SEQUENCE: 35

His Gly Glu Gly Thr Phe Thr Ser Asp Leu Ser Lys Gln Met Glu Glu
  1               5                  10                  15

Glu Ala Val Arg Leu Phe Ile Glu Trp Leu Lys Asn Gly Gly Pro Ser
             20                  25                  30

Ser Gly Ala Xaa Xaa Xaa Ser
          35

<210> SEQ ID NO 36
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: VARIANT
<222> LOCATION: (31)
<223> OTHER INFORMATION: Xaa at position 31 is thioproline
<220> FEATURE:
<221> NAME/KEY: VARIANT
<222> LOCATION: (36)..(38)
<223> OTHER INFORMATION: Xaa at positions 36,37, and 38 is thioproline
<220> FEATURE:
<221> NAME/KEY: MOD_RES
<222> LOCATION: (39)
<223> OTHER INFORMATION: AMIDATION, Position 39 is Ser-NH2

<400> SEQUENCE: 36
```

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Xaa Ser
            20                  25                  30

Ser Gly Ala Xaa Xaa Xaa Ser
        35

<210> SEQ ID NO 37
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: VARIANT
<222> LOCATION: (31)
<223> OTHER INFORMATION: Xaa at position 31 is homoproline
<220> FEATURE:
<221> NAME/KEY: VARIANT
<222> LOCATION: (36)..(38)
<223> OTHER INFORMATION: Xaa at positions 36,37, and 38 is homoproline
<220> FEATURE:
<221> NAME/KEY: MOD_RES
<222> LOCATION: (39)
<223> OTHER INFORMATION: AMIDATION, Position 39 is Ser-NH2

<400> SEQUENCE: 37

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Xaa Ser
            20                  25                  30

Ser Gly Ala Xaa Xaa Xaa Ser
        35

<210> SEQ ID NO 38
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: VARIANT
<222> LOCATION: (31)
<223> OTHER INFORMATION: Xaa at position 31 is N-methylalanine
<220> FEATURE:
<221> NAME/KEY: VARIANT
<222> LOCATION: (36)..(38)
<223> OTHER INFORMATION: Xaa at positions 36, 37 and 38 is
      N-methylalanine
<220> FEATURE:
<221> NAME/KEY: MOD_RES
<222> LOCATION: (39)
<223> OTHER INFORMATION: AMIDATION, Position 39 is Ser-NH2

<400> SEQUENCE: 38

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Xaa Ser
            20                  25                  30

Ser Gly Ala Xaa Xaa Xaa Ser
        35

<210> SEQ ID NO 39
<211> LENGTH: 39
<212> TYPE: PRT
<213> ORGANISM: Artificial Sequence

```
<220> FEATURE:
<223> OTHER INFORMATION: Description of Artificial Sequence: Synthetic
      Construct
<220> FEATURE:
<221> NAME/KEY: VARIANT
<222> LOCATION: (36)..(38)
<223> OTHER INFORMATION: Xaa at positions 36, 37, and 38 is
      N-methylalanine
<220> FEATURE:
<221> NAME/KEY: MOD_RES
<222> LOCATION: (39)
<223> OTHER INFORMATION: AMIDATION, Position 39 is Ser-NH2

<400> SEQUENCE: 39

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Xaa Xaa Xaa Ser
        35

<210> SEQ ID NO 40
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: VARIANT
<222> LOCATION: (31)
<223> OTHER INFORMATION: Xaa at position 31 is N-methylalanine
<220> FEATURE:
<221> NAME/KEY: VARIANT
<222> LOCATION: (36)..(38)
<223> OTHER INFORMATION: Xaa at positions 36, 37, and 38 is
      N-methylalanine
<220> FEATURE:
<221> NAME/KEY: MOD_RES
<222> LOCATION: (39)
<223> OTHER INFORMATION: AMIDATION, Position 39 is Ser-NH2

<400> SEQUENCE: 40

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly Xaa Ser
            20                  25                  30

Ser Gly Ala Xaa Xaa Xaa Ser
        35

<210> SEQ ID NO 41
<211> LENGTH: 29
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: VARIANT
<222> LOCATION: (1)
<223> OTHER INFORMATION: Xaa at position 1 is His, Arg or Tyr
<220> FEATURE:
<221> NAME/KEY: VARIANT
<222> LOCATION: (2)
<223> OTHER INFORMATION: Xaa at position 2 is Ser, Gly Ala, or Thr
<220> FEATURE:
<221> NAME/KEY: VARIANT
<222> LOCATION: (3)
<223> OTHER INFORMATION: Xaa at position 3 is Asp or Glu
<220> FEATURE:
<221> NAME/KEY: VARIANT
```

-continued

```
<222> LOCATION: (5)
<223> OTHER INFORMATION: Xaa at position 5 is Ala or Thr
<220> FEATURE:
<221> NAME/KEY: VARIANT
<222> LOCATION: (6)
<223> OTHER INFORMATION: Xaa at position 6 is Ala, Phe, Tyr or
      napthylalanine
<220> FEATURE:
<221> NAME/KEY: VARIANT
<222> LOCATION: (7)
<223> OTHER INFORMATION: Xaa at position 7 is Thr or Ser
<220> FEATURE:
<221> NAME/KEY: VARIANT
<222> LOCATION: (8)
<223> OTHER INFORMATION: Xaa at position 8 is Ala, Ser or Thr
<220> FEATURE:
<221> NAME/KEY: VARIANT
<222> LOCATION: (9)
<223> OTHER INFORMATION: Xaa at position 9 is Asp or Glu
<220> FEATURE:
<221> NAME/KEY: VARIANT
<222> LOCATION: (10)
<223> OTHER INFORMATION: Xaa at position 10 is Ala, Leu, Ile, Val,
      pentylglycine, or Met
<220> FEATURE:
<221> NAME/KEY: VARIANT
<222> LOCATION: (11)
<223> OTHER INFORMATION: Xaa at position 11 is Ala or Ser
<220> FEATURE:
<221> NAME/KEY: VARIANT
<222> LOCATION: (12)
<223> OTHER INFORMATION: Xaa at position 12 is Ala or Lys
<220> FEATURE:
<221> NAME/KEY: VARIANT
<222> LOCATION: (13)
<223> OTHER INFORMATION: Xaa at position 13 is Ala or Gln
<220> FEATURE:
<221> NAME/KEY: VARIANT
<222> LOCATION: (14)
<223> OTHER INFORMATION: Xaa at position 14 is Ala, Leu, Ile,
      pentylglycine, Val or Met
<220> FEATURE:
<221> NAME/KEY: VARIANT
<222> LOCATION: (15)
<223> OTHER INFORMATION: Xaa at position 15 is Ala or Glu
<220> FEATURE:
<221> NAME/KEY: VARIANT
<222> LOCATION: (16)..(17)
<223> OTHER INFORMATION: Xaa at position 16 and 17 is Ala or Glu
<220> FEATURE:
<221> NAME/KEY: VARIANT
<222> LOCATION: (19)
<223> OTHER INFORMATION: Xaa at position 19 is Ala or Val
<220> FEATURE:
<221> NAME/KEY: VARIANT
<222> LOCATION: (20)
<223> OTHER INFORMATION: Xaa at position 20 is Ala or Arg
<220> FEATURE:
<221> NAME/KEY: VARIANT
<222> LOCATION: (21)
<223> OTHER INFORMATION: Xaa at position 21 is Ala or Leu
<220> FEATURE:
<221> NAME/KEY: VARIANT
<222> LOCATION: (22)
<223> OTHER INFORMATION: Xaa at position 22 is Ala, Phe, Tyr, or
      naphthylalanine
<220> FEATURE:
<221> NAME/KEY: VARIANT
<222> LOCATION: (23)
<223> OTHER INFORMATION: Xaa at position 23 is Ile, Val, Leu,
      pentylglycine, tert-butylglycine, or Met
<220> FEATURE:
<221> NAME/KEY: VARIANT
<222> LOCATION: (24)
<223> OTHER INFORMATION: Xaa at position 24 is Ala, Glu, or Asp
<220> FEATURE:
<221> NAME/KEY: VARIANT
<222> LOCATION: (25)
<223> OTHER INFORMATION: Xaa at position 25 is Ala, Trp, Phe, Tyr or
```

```
      napthylalanine
<220> FEATURE:
<221> NAME/KEY: VARIANT
<222> LOCATION: (26)
<223> OTHER INFORMATION: Xaa at position 26 is Ala or Leu
<220> FEATURE:
<221> NAME/KEY: VARIANT
<222> LOCATION: (27)
<223> OTHER INFORMATION: Xaa at position 27 is Ala or Lys
<220> FEATURE:
<221> NAME/KEY: VARIANT
<222> LOCATION: (28)
<223> OTHER INFORMATION: Xaa at position 28 is Ala or Asn
<220> FEATURE:
<221> NAME/KEY: VARIANT
<222> LOCATION: (29)
<223> OTHER INFORMATION: Xaa at position 29 is OH, NH2, Gly-OH, Gly-NH2,
      Gly-Gly-OH, Gly-Gly-NH2 and further as in the
      specification

<400> SEQUENCE: 41

Xaa Xaa Xaa Gly Xaa Xaa Xaa Xaa Xaa Xaa Xaa Xaa Xaa Xaa Xaa Xaa
 1               5                   10                  15

Xaa Xaa Xaa Xaa Xaa Xaa Xaa Xaa Xaa Xaa Xaa Xaa Xaa
            20                  25

<210> SEQ ID NO 42
<211> LENGTH: 29
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: VARIANT
<222> LOCATION: (1)
<223> OTHER INFORMATION: Xaa at position 1 is His, Arg, Tyr, Ala,
      norvaline, Val, or norleucine
<220> FEATURE:
<221> NAME/KEY: VARIANT
<222> LOCATION: (2)
<223> OTHER INFORMATION: Xaa at position 2 is Ser, Gly, Ala, or Thr
<220> FEATURE:
<221> NAME/KEY: VARIANT
<222> LOCATION: (3)
<223> OTHER INFORMATION: Xaa at position 3 is Ala, Asp, or Glu
<220> FEATURE:
<221> NAME/KEY: VARIANT
<222> LOCATION: (4)
<223> OTHER INFORMATION: Xaa at position 4 is Ala, norvaline, Val,
      norleucine or Gly
<220> FEATURE:
<221> NAME/KEY: VARIANT
<222> LOCATION: (5)
<223> OTHER INFORMATION: Xaa at position 5 is Ala or Thr
<220> FEATURE:
<221> NAME/KEY: VARIANT
<222> LOCATION: (6)
<223> OTHER INFORMATION: Xaa at position 6 is Phe, Tyr, or
      napthylalanine
<220> FEATURE:
<221> NAME/KEY: VARIANT
<222> LOCATION: (7)
<223> OTHER INFORMATION: Xaa at position 7 is Thr or Ser
<220> FEATURE:
<221> NAME/KEY: VARIANT
<222> LOCATION: (8)
<223> OTHER INFORMATION: Xaa at position 8 is Ala, Ser, or Thr
<220> FEATURE:
<221> NAME/KEY: VARIANT
<222> LOCATION: (9)
<223> OTHER INFORMATION: Xaa at position 9 is Ala, norvaline,
      norleucine, Asp or Glu
<220> FEATURE:
<221> NAME/KEY: VARIANT
<222> LOCATION: (10)
```

```
<223> OTHER INFORMATION: Xaa at position 10 is Ala, Leu, Ile, Val,
      pentylglycine, or Met
<220> FEATURE:
<221> NAME/KEY: VARIANT
<222> LOCATION: (11)
<223> OTHER INFORMATION: Xaa at position 11 is Ala of Ser
<220> FEATURE:
<221> NAME/KEY: VARIANT
<222> LOCATION: (12)
<223> OTHER INFORMATION: Xaa at position 12 is Ala or Lys
<220> FEATURE:
<221> NAME/KEY: VARIANT
<222> LOCATION: (13)
<223> OTHER INFORMATION: Xaa at position 13 is Ala or Gln
<220> FEATURE:
<221> NAME/KEY: VARIANT
<222> LOCATION: (14)
<223> OTHER INFORMATION: Xaa at position 14 is Ala, Leu, Ile,
      pentylglycine, Val or Met
<220> FEATURE:
<221> NAME/KEY: VARIANT
<222> LOCATION: (15)..(17)
<223> OTHER INFORMATION: Xaa at positions 15, 16, and 17 is Ala or Glu
<220> FEATURE:
<221> NAME/KEY: VARIANT
<222> LOCATION: (19)
<223> OTHER INFORMATION: Xaa at position 19 is Ala or Val
<220> FEATURE:
<221> NAME/KEY: VARIANT
<222> LOCATION: (20)
<223> OTHER INFORMATION: Xaa at position 20 is Ala or Arg
<220> FEATURE:
<221> NAME/KEY: VARIANT
<222> LOCATION: (21)
<223> OTHER INFORMATION: Xaa at position 21 is Ala or Leu
<220> FEATURE:
<221> NAME/KEY: VARIANT
<222> LOCATION: (22)
<223> OTHER INFORMATION: Xaa at position 22 is Phe, Tyr or
      napthylalanine
<220> FEATURE:
<221> NAME/KEY: VARIANT
<222> LOCATION: (23)
<223> OTHER INFORMATION: Xaa at position 23 is Ile, Val, Leu,
      pentylglycine, tert-butylglycine or Met
<220> FEATURE:
<221> NAME/KEY: VARIANT
<222> LOCATION: (24)
<223> OTHER INFORMATION: Xaa at position 24 is Ala, Glu or Asp
<220> FEATURE:
<221> NAME/KEY: VARIANT
<222> LOCATION: (25)
<223> OTHER INFORMATION: Xaa at position 25 is Ala, Trp, Phe, Tyr or
      napthylalanine
<220> FEATURE:
<221> NAME/KEY: VARIANT
<222> LOCATION: (26)
<223> OTHER INFORMATION: Xaa at position 26 is Ala or Leu
<220> FEATURE:
<221> NAME/KEY: VARIANT
<222> LOCATION: (27)
<223> OTHER INFORMATION: Xaa at position 27 is Ala or Lys
<220> FEATURE:
<221> NAME/KEY: VARIANT
<222> LOCATION: (28)
<223> OTHER INFORMATION: Xaa at position 28 is Ala or Asn
<220> FEATURE:
<221> NAME/KEY: VARIANT
<222> LOCATION: (29)
<223> OTHER INFORMATION: Xaa at position 29 is OH, NH2, Gly-OH, Gly-NH2,
      Gly-Gly-OH, Gly-Gly-NH2 and further as indicated in the
      specification

<400> SEQUENCE: 42

Xaa Xaa Xaa Xaa Xaa Xaa Xaa Xaa Xaa Xaa Xaa Xaa Xaa Xaa Xaa Xaa
 1               5                  10                  15

Xaa Ala Xaa Xaa Xaa Xaa Xaa Xaa Xaa Xaa Xaa Xaa Xaa
```

```
                        20                  25

<210> SEQ ID NO 43
<211> LENGTH: 29
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: VARIANT
<222> LOCATION: (1)
<223> OTHER INFORMATION: Xaa at position1 is His or Arg
<220> FEATURE:
<221> NAME/KEY: VARIANT
<222> LOCATION: (2)
<223> OTHER INFORMATION: Xaa at position 2 is Gly or Ala
<220> FEATURE:
<221> NAME/KEY: VARIANT
<222> LOCATION: (3)
<223> OTHER INFORMATION: Xaa at position 3 is Asp or Glu
<220> FEATURE:
<221> NAME/KEY: VARIANT
<222> LOCATION: (5)
<223> OTHER INFORMATION: Xaa at position 5 is Ala or Thr
<220> FEATURE:
<221> NAME/KEY: VARIANT
<222> LOCATION: (6)
<223> OTHER INFORMATION: Xaa at position 6 is Ala, Phe, or
      napthylalanine
<220> FEATURE:
<221> NAME/KEY: VARIANT
<222> LOCATION: (7)
<223> OTHER INFORMATION: Xaa at position 7 is Ser, or Thr
<220> FEATURE:
<221> NAME/KEY: VARIANT
<222> LOCATION: (8)
<223> OTHER INFORMATION: Xaa at position 8 is Ala, Ser, or Thr
<220> FEATURE:
<221> NAME/KEY: VARIANT
<222> LOCATION: (9)
<223> OTHER INFORMATION: Xaa at position 9 is Asp or Glu
<220> FEATURE:
<221> NAME/KEY: VARIANT
<222> LOCATION: (10)
<223> OTHER INFORMATION: Xaa at position 10 is Ala, Leu, or
      pentylglycine
<220> FEATURE:
<221> NAME/KEY: VARIANT
<222> LOCATION: (11)
<223> OTHER INFORMATION: Xaa at position 11 is Ala or Ser
<220> FEATURE:
<221> NAME/KEY: VARIANT
<222> LOCATION: (12)
<223> OTHER INFORMATION: Xaa at position 12 is Ala or Lys
<220> FEATURE:
<221> NAME/KEY: VARIANT
<222> LOCATION: (13)
<223> OTHER INFORMATION: Xaa at position 13 Ala or Gln
<220> FEATURE:
<221> NAME/KEY: VARIANT
<222> LOCATION: (14)
<223> OTHER INFORMATION: Xaa at position 14 is Ala, Leu or
      pentylglycine
<220> FEATURE:
<221> NAME/KEY: VARIANT
<222> LOCATION: (15)..(17)
<223> OTHER INFORMATION: Xaa at positions 15, 16, and 17 is Ala or Glu
<220> FEATURE:
<221> NAME/KEY: VARIANT
<222> LOCATION: (19)
<223> OTHER INFORMATION: Xaa at position 19 is Ala or Val
<220> FEATURE:
<221> NAME/KEY: VARIANT
<222> LOCATION: (20)
<223> OTHER INFORMATION: Xaa at position 20 is Ala or Arg
<220> FEATURE:
<221> NAME/KEY: VARIANT
```

```
<222> LOCATION: (21)
<223> OTHER INFORMATION: Xaa at position 21 is Ala or Leu
<220> FEATURE:
<221> NAME/KEY: VARIANT
<222> LOCATION: (22)
<223> OTHER INFORMATION: Xaa at position 22 is Phe or napthylalanine
<220> FEATURE:
<221> NAME/KEY: VARIANT
<222> LOCATION: (23)
<223> OTHER INFORMATION: Xaa at position 23 is Ile, Val or
      tert-butylglycine
<220> FEATURE:
<221> NAME/KEY: VARIANT
<222> LOCATION: (24)
<223> OTHER INFORMATION: Xaa at position 24 is Ala, Glu or Asp
<220> FEATURE:
<221> NAME/KEY: VARIANT
<222> LOCATION: (25)
<223> OTHER INFORMATION: Xaa at position 25 is Ala, Trp or Phe
<220> FEATURE:
<221> NAME/KEY: VARIANT
<222> LOCATION: (26)
<223> OTHER INFORMATION: Xaa at position 26 is Ala or Leu
<220> FEATURE:
<221> NAME/KEY: VARIANT
<222> LOCATION: (27)
<223> OTHER INFORMATION: Xaa at position is Ala or Lys
<220> FEATURE:
<221> NAME/KEY: VARIANT
<222> LOCATION: (28)
<223> OTHER INFORMATION: Xaa at position 28 is Ala or Asn
<220> FEATURE:
<221> NAME/KEY: VARIANT
<222> LOCATION: (29)
<223> OTHER INFORMATION: Xaa at position 29 is -OH, -NH2, Gly-OH,
      Gly-NH2, Gly-Gly-Oh, Gly-Gly-NH2, and further as indicated in the
      specification

<400> SEQUENCE: 43

Xaa Xaa Xaa Gly Xaa Xaa Xaa Xaa Xaa Xaa Xaa Xaa Xaa Xaa Xaa Xaa
 1               5                   10                  15

Xaa Ala Xaa Xaa Xaa Xaa Xaa Xaa Xaa Xaa Xaa Xaa Xaa
            20                  25

<210> SEQ ID NO 44
<211> LENGTH: 29
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: VARIANT
<222> LOCATION: (1)
<223> OTHER INFORMATION: Xaa in position 1 is His or Ala
<220> FEATURE:
<221> NAME/KEY: VARIANT
<222> LOCATION: (2)
<223> OTHER INFORMATION: Xaa in position 2 is Gly or Ala
<220> FEATURE:
<221> NAME/KEY: VARIANT
<222> LOCATION: (3)
<223> OTHER INFORMATION: Xaa in position 3 is Ala, Asp or Glu
<220> FEATURE:
<221> NAME/KEY: VARIANT
<222> LOCATION: (4)
<223> OTHER INFORMATION: Xaa in position 4 is Ala or Gly
<220> FEATURE:
<221> NAME/KEY: VARIANT
<222> LOCATION: (5)
<223> OTHER INFORMATION: Xaa in position 5 is Ala or Thr
<220> FEATURE:
<221> NAME/KEY: VARIANT
<222> LOCATION: (6)
<223> OTHER INFORMATION: Xaa in position 6 is Phe or napthylalanine
<220> FEATURE:
```

-continued

```
<221> NAME/KEY: VARIANT
<222> LOCATION: (7)
<223> OTHER INFORMATION: Xaa in position 7 is Thr or Ser
<220> FEATURE:
<221> NAME/KEY: VARIANT
<222> LOCATION: (8)
<223> OTHER INFORMATION: Xaa in position 8 is Ala, Ser or Thr
<220> FEATURE:
<221> NAME/KEY: VARIANT
<222> LOCATION: (9)
<223> OTHER INFORMATION: Xaa in position 9 is Ala, Asp or Glu
<220> FEATURE:
<221> NAME/KEY: VARIANT
<222> LOCATION: (10)
<223> OTHER INFORMATION: Xaa in position 10 is Ala, Leu or pentylglycine
<220> FEATURE:
<221> NAME/KEY: VARIANT
<222> LOCATION: (11)
<223> OTHER INFORMATION: Xaa in position 11 is Ala or Ser
<220> FEATURE:
<221> NAME/KEY: VARIANT
<222> LOCATION: (12)
<223> OTHER INFORMATION: Xaa in position 12 is Ala or Lys
<220> FEATURE:
<221> NAME/KEY: VARIANT
<222> LOCATION: (13)
<223> OTHER INFORMATION: Xaain position 13 is Ala or Gln
<220> FEATURE:
<221> NAME/KEY: VARIANT
<222> LOCATION: (14)
<223> OTHER INFORMATION: Xaa in position 14 is Ala, Leu, Met or
      pentylglycine
<220> FEATURE:
<221> NAME/KEY: VARIANT
<222> LOCATION: (15)..(17)
<223> OTHER INFORMATION: Xaa in positions 15, 16 & 17 is Ala or Glu
<220> FEATURE:
<221> NAME/KEY: VARIANT
<222> LOCATION: (19)
<223> OTHER INFORMATION: Xaa in position 19 is Ala or Val
<220> FEATURE:
<221> NAME/KEY: VARIANT
<222> LOCATION: (20)
<223> OTHER INFORMATION: Xaa in position 20 is Ala or Arg
<220> FEATURE:
<221> NAME/KEY: VARIANT
<222> LOCATION: (21)
<223> OTHER INFORMATION: Xaa in position 21 is Ala or Leu
<220> FEATURE:
<221> NAME/KEY: VARIANT
<222> LOCATION: (22)
<223> OTHER INFORMATION: Xaa at position 22 is Phe or napthylalanine
<220> FEATURE:
<221> NAME/KEY: VARIANT
<222> LOCATION: (23)
<223> OTHER INFORMATION: Xaa at position 23 is Ile, Val or
      tert-butylglycine
<220> FEATURE:
<221> NAME/KEY: VARIANT
<222> LOCATION: (24)
<223> OTHER INFORMATION: Xaa at position 24 is Ala, Glu or Asp
<220> FEATURE:
<221> NAME/KEY: VARIANT
<222> LOCATION: (25)
<223> OTHER INFORMATION: Xaa at position 25 is Ala, Trp or Phe
<220> FEATURE:
<221> NAME/KEY: VARIANT
<222> LOCATION: (26)
<223> OTHER INFORMATION: Xaa at position 26 is Ala or Leu
<220> FEATURE:
<221> NAME/KEY: VARIANT
<222> LOCATION: (27)
<223> OTHER INFORMATION: Xaa at position 27 is Ala or Lys
<220> FEATURE:
<221> NAME/KEY: VARIANT
<222> LOCATION: (28)
<223> OTHER INFORMATION: Xaa at position 28 is Ala or Asn
<220> FEATURE:
<221> NAME/KEY: VARIANT
```

```
<222> LOCATION: (29)
<223> OTHER INFORMATION: Xaa at position 29 is OH, NH2, Gly-OH, Gly-NH2,
      Gly-Gly-OH, Gly-Gly-NH2 and further as indicated
      in the specification

<400> SEQUENCE: 44

Xaa Xaa Xaa Xaa Xaa Xaa Xaa Xaa Xaa Xaa Xaa Xaa Xaa Xaa Xaa Xaa
1               5                   10                  15

Xaa Ala Xaa Xaa Xaa Xaa Xaa Xaa Xaa Xaa Xaa Xaa Xaa
            20                  25

<210> SEQ ID NO 45
<211> LENGTH: 28
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: VARIANT
<222> LOCATION: (1)
<223> OTHER INFORMATION: Xaa in position 1 is His, Arg, Tyr or
      4-imidazopropionyl
<220> FEATURE:
<221> NAME/KEY: VARIANT
<222> LOCATION: (2)
<223> OTHER INFORMATION: Xaa in positon 2 is Ser, Gly, Ala or Thr
<220> FEATURE:
<221> NAME/KEY: VARIANT
<222> LOCATION: (3)
<223> OTHER INFORMATION: Xaa in position 3 is Asp or Glu
<220> FEATURE:
<221> NAME/KEY: VARIANT
<222> LOCATION: (5)
<223> OTHER INFORMATION: Xaa in position 5 is Ala or Thr
<220> FEATURE:
<221> NAME/KEY: VARIANT
<222> LOCATION: (6)
<223> OTHER INFORMATION: Xaa in position 6 is Ala, Phe, Tyr or
      napthylalanine
<220> FEATURE:
<221> NAME/KEY: VARIANT
<222> LOCATION: (7)
<223> OTHER INFORMATION: Xaa in position 8 is Thr or Ser
<220> FEATURE:
<221> NAME/KEY: VARIANT
<222> LOCATION: (8)
<223> OTHER INFORMATION: Xaa in position 8 is Ala, Ser or Thr
<220> FEATURE:
<221> NAME/KEY: VARIANT
<222> LOCATION: (9)
<223> OTHER INFORMATION: Xaa in position 9 is Asp or Glu
<220> FEATURE:
<221> NAME/KEY: VARIANT
<222> LOCATION: (10)
<223> OTHER INFORMATION: Xaa in position 10 is Ala, Leu, Ile, Val,
      pentylglycine or Met
<220> FEATURE:
<221> NAME/KEY: VARIANT
<222> LOCATION: (11)
<223> OTHER INFORMATION: Xaa in position 11 is Ala or Ser
<220> FEATURE:
<221> NAME/KEY: VARIANT
<222> LOCATION: (12)
<223> OTHER INFORMATION: Xaa in position 12 is Ala or Lys
<220> FEATURE:
<221> NAME/KEY: VARIANT
<222> LOCATION: (13)
<223> OTHER INFORMATION: Xaa in position 13 is Ala or Gln
<220> FEATURE:
<221> NAME/KEY: VARIANT
<222> LOCATION: (14)
<223> OTHER INFORMATION: Xaa in position 14 is Ala, Leu, Ile,
      pentylglycine, Val or Met
<220> FEATURE:
<221> NAME/KEY: VARIANT
```

```
<222> LOCATION: (15)..(17)
<223> OTHER INFORMATION: Xaa in positions 15, 16 & 17 is Ala or Glu
<220> FEATURE:
<221> NAME/KEY: VARIANT
<222> LOCATION: (19)
<223> OTHER INFORMATION: Xaa in position 19 is Ala or Val
<220> FEATURE:
<221> NAME/KEY: VARIANT
<222> LOCATION: (20)
<223> OTHER INFORMATION: Xaa in position 20 is Ala or Arg
<220> FEATURE:
<221> NAME/KEY: VARIANT
<222> LOCATION: (21)
<223> OTHER INFORMATION: Xaa in position 21 is Ala, Leu, Lys-NH3-R where
      R is Lys, Arg, C1-C10 straight chain or branched alkanoyl or
      cycloalkanoyl
<220> FEATURE:
<221> NAME/KEY: VARIANT
<222> LOCATION: (22)
<223> OTHER INFORMATION: Xaa in position 22 is Phe, Tyr, or
      naphthylalanine
<220> FEATURE:
<221> NAME/KEY: VARIANT
<222> LOCATION: (23)
<223> OTHER INFORMATION: Xaa at position 23 is Ile, Val, Leu,
      pentylglycine, tert-butylglycine or Met
<220> FEATURE:
<221> NAME/KEY: VARIANT
<222> LOCATION: (24)
<223> OTHER INFORMATION: Xaa at position 24 is Ala, Glu or Asp
<220> FEATURE:
<221> NAME/KEY: VARIANT
<222> LOCATION: (25)
<223> OTHER INFORMATION: Xaa at position 25 is Ala, Trp, Phe, Tyr or
      naphthylalanine
<220> FEATURE:
<221> NAME/KEY: VARIANT
<222> LOCATION: (26)
<223> OTHER INFORMATION: Xaa at position 26 is Ala or Leu
<220> FEATURE:
<221> NAME/KEY: VARIANT
<222> LOCATION: (27)
<223> OTHER INFORMATION: Xaa at position 27 is Lys-Asn, Asn-Lys,
      Lys-NH3-R-Asn, Asn-Lys-NH3-R, Lys-NH3-R-Ala,
      Ala-Lys-NH3-R, where R is Lys, Arg, C1-C10 straight
      chain or branched alkanoyl or cycloalkylalkanoyl
<220> FEATURE:
<221> NAME/KEY: VARIANT
<222> LOCATION: (28)
<223> OTHER INFORMATION: Xaa at position 28 is OH, NH2, Gly-OH, Gly-NH2,
      Gly-Gly-OH, Gly-Gly-NH2 and further as indicated in the
      specification

<400> SEQUENCE: 45

Xaa Xaa Xaa Gly Xaa Xaa Xaa Xaa Xaa Xaa Xaa Xaa Xaa Xaa Xaa Xaa
 1               5                  10                  15

Xaa Xaa Ala Xaa Xaa Xaa Xaa Xaa Xaa Xaa Xaa Xaa
            20                  25

<210> SEQ ID NO 46
<211> LENGTH: 28
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: VARIANT
<222> LOCATION: (1)
<223> OTHER INFORMATION: Xaa in position 1 is His, Arg, Tyr, Ala,
      norvaline, Val norleucine, or 4-imidazopropionyl
<220> FEATURE:
<221> NAME/KEY: VARIANT
<222> LOCATION: (2)
<223> OTHER INFORMATION: Xaa in position 2 is Ser, Gly, Ala, or Thr
<220> FEATURE:
```

```
<221> NAME/KEY: VARIANT
<222> LOCATION: (3)
<223> OTHER INFORMATION: Xaa in position 3 is Ala, Asp, or Glu
<220> FEATURE:
<221> NAME/KEY: VARIANT
<222> LOCATION: (4)
<223> OTHER INFORMATION: Xaa in position 4 is Ala, norvaline, Val,
      norleucine or Gly
<220> FEATURE:
<221> NAME/KEY: VARIANT
<222> LOCATION: (5)
<223> OTHER INFORMATION: Xaa in position 5 is Ala or Thr
<220> FEATURE:
<221> NAME/KEY: VARIANT
<222> LOCATION: (6)
<223> OTHER INFORMATION: Xaa in position 6 is Phe, Tyr or napthylalanine
<220> FEATURE:
<221> NAME/KEY: VARIANT
<222> LOCATION: (7)
<223> OTHER INFORMATION: Xaa in position 7 is Thr or Ser
<220> FEATURE:
<221> NAME/KEY: VARIANT
<222> LOCATION: (8)
<223> OTHER INFORMATION: Xaa in position 8 is Ala, Ser or Thr
<220> FEATURE:
<221> NAME/KEY: VARIANT
<222> LOCATION: (9)
<223> OTHER INFORMATION: Xaa in position 9 is Ala, Norvaline, Val,
      Norleucine, Asp or Glu
<220> FEATURE:
<221> NAME/KEY: VARIANT
<222> LOCATION: (10)
<223> OTHER INFORMATION: Xaa in position 10 is Ala, Leu, Ile, Val
      pentylglycine or Met
<220> FEATURE:
<221> NAME/KEY: VARIANT
<222> LOCATION: (11)
<223> OTHER INFORMATION: Xaa in position 11 is Ala or Ser
<220> FEATURE:
<221> NAME/KEY: VARIANT
<222> LOCATION: (12)
<223> OTHER INFORMATION: Xaa in position 12 is Ala or Lys
<220> FEATURE:
<221> NAME/KEY: VARIANT
<222> LOCATION: (13)
<223> OTHER INFORMATION: Xaa in position 13 is Ala or Gln
<220> FEATURE:
<221> NAME/KEY: VARIANT
<222> LOCATION: (14)
<223> OTHER INFORMATION: Xaa in position 14 is Ala, Leu, Ile,
      pentylglycine Val or Met
<220> FEATURE:
<221> NAME/KEY: VARIANT
<222> LOCATION: (15)..(17)
<223> OTHER INFORMATION: Xaa in positions 15, 16 & 17 stands for Ala
      or Glu
<220> FEATURE:
<221> NAME/KEY: VARIANT
<222> LOCATION: (19)
<223> OTHER INFORMATION: Xaa in position 19 is Ala or Val
<220> FEATURE:
<221> NAME/KEY: VARIANT
<222> LOCATION: (20)
<223> OTHER INFORMATION: Xaa in position 20 is Ala or Arg
<220> FEATURE:
<221> NAME/KEY: VARIANT
<222> LOCATION: (21)
<223> OTHER INFORMATION: Xaa in position 21 is Ala, Leu or Lys-NH3 where
      R is Lys, Arg, C1-C10 straight chain or branched alkanoyl or
      cycloalleyl-alkanoyl
<220> FEATURE:
<221> NAME/KEY: VARIANT
<222> LOCATION: (22)
<223> OTHER INFORMATION: Xaa at position 22 is Phe, Tyr or
      naphthylalanine
<220> FEATURE:
<221> NAME/KEY: VARIANT
<222> LOCATION: (23)
<223> OTHER INFORMATION: Xaa at position 23 is Ile, Val, Leu,
```

```
       pentylglycine, tert-butylglycine or Met
<220> FEATURE:
<221> NAME/KEY: VARIANT
<222> LOCATION: (24)
<223> OTHER INFORMATION: Xaa at position 24 is Ala, Glu or Asp
<220> FEATURE:
<221> NAME/KEY: VARIANT
<222> LOCATION: (25)
<223> OTHER INFORMATION: Xaa at position 25 is Ala, Trp, Phe, Tyr
       or naphthylalanine
<220> FEATURE:
<221> NAME/KEY: VARIANT
<222> LOCATION: (26)
<223> OTHER INFORMATION: Xaa at position 26 is Ala or Leu
<220> FEATURE:
<221> NAME/KEY: VARIANT
<222> LOCATION: (27)
<223> OTHER INFORMATION: Xaa at position 27 is Lys-Asn, Asn-Lys,
       Lys-NH3-R-Asn, Asn-Lys-NH3-R, Lys-NH3-R-Ala,
       Ala-Lys-NH3-R, where R is Lys, Arg, C1-C10 straight
       chain or branched alkanoyl or cycloalkylalkanoyl
<220> FEATURE:
<221> NAME/KEY: VARIANT
<222> LOCATION: (28)
<223> OTHER INFORMATION: Xaa at position 28 is OH, NH2, Gly-OH, Gly-NH2,
       Gly-Gly-OH, Gly-Gly-NH2 and further as indicated
       in the specification

<400> SEQUENCE: 46

Xaa Xaa Xaa Xaa Xaa Xaa Xaa Xaa Xaa Xaa Xaa Xaa Xaa Xaa Xaa Xaa
 1               5                  10                  15

Xaa Ala Xaa Xaa Xaa Xaa Xaa Xaa Xaa Xaa Xaa Xaa
            20                  25

<210> SEQ ID NO 47
<211> LENGTH: 40
<212> TYPE: PRT
<213> ORGANISM: Artificial Sequence
<220> FEATURE:
<223> OTHER INFORMATION: Description of Artificial Sequence: Synthetic
       Construct
<220> FEATURE:
<221> NAME/KEY: VARIANT
<222> LOCATION: (1)
<223> OTHER INFORMATION: Xaa in position 1 is His, Arg or Thr
<220> FEATURE:
<221> NAME/KEY: VARIANT
<222> LOCATION: (2)
<223> OTHER INFORMATION: Xaa in position 2 is Ser, Gly, Ala, or Thr
<220> FEATURE:
<221> NAME/KEY: VARIANT
<222> LOCATION: (3)
<223> OTHER INFORMATION: Xaa in position 3 is Asp or Glu
<220> FEATURE:
<221> NAME/KEY: VARIANT
<222> LOCATION: (6)
<223> OTHER INFORMATION: Xaa in position 6 is Phe, Tyr or naphthalanine
<220> FEATURE:
<221> NAME/KEY: VARIANT
<222> LOCATION: (7)
<223> OTHER INFORMATION: Xaa in position 7 is Thr or Ser
<220> FEATURE:
<221> NAME/KEY: VARIANT
<222> LOCATION: (8)
<223> OTHER INFORMATION: Xaa in position 8 is Ser or Thr
<220> FEATURE:
<221> NAME/KEY: VARIANT
<222> LOCATION: (9)
<223> OTHER INFORMATION: Xaa in position 9 is Asp or Glu
<220> FEATURE:
<221> NAME/KEY: VARIANT
<222> LOCATION: (10)
<223> OTHER INFORMATION: Xaa in position 10 is Leu, Ile, Val,
       pentylglycine or Met
<220> FEATURE:
<221> NAME/KEY: VARIANT
```

```
<222> LOCATION: (14)
<223> OTHER INFORMATION: Xaa at position 14 is Leu, Ile, pentylglycine,
      Val or Met
<220> FEATURE:
<221> NAME/KEY: VARIANT
<222> LOCATION: (22)
<223> OTHER INFORMATION: Xaa in position 22 is Phe, Tyr or
      naphthylalanine
<220> FEATURE:
<221> NAME/KEY: VARIANT
<222> LOCATION: (23)
<223> OTHER INFORMATION: Xaa in position 23 is Ile, Val, Leu,
      pentylglycine, tert-butylglycine or Met
<220> FEATURE:
<221> NAME/KEY: VARIANT
<222> LOCATION: (24)
<223> OTHER INFORMATION: Xaa in position 24 is Glu or Asp
<220> FEATURE:
<221> NAME/KEY: VARIANT
<222> LOCATION: (25)
<223> OTHER INFORMATION: Xaa in position 25 is Trp, Phe, Tyr or
      naphthylalanine
<220> FEATURE:
<221> NAME/KEY: VARIANT
<222> LOCATION: (31)
<223> OTHER INFORMATION: Xaa in position 31 is independently Pro,
      homoproline, 3-hydroxyproline, 4-hydroxyproline, thioproline,
      N-alkylglycine, N-alkylpentylglycine or N-alkylalanine
<220> FEATURE:
<221> NAME/KEY: VARIANT
<222> LOCATION: (36)..(38)
<223> OTHER INFORMATION: Xaa in positions 36, 37 & 38 is independently
      Pro, homoproline, 3-hydroxyproline, 4-hydroxproline, thioproline,
      N-alkylglycine, N-alkylpentylglycine or N-alkylalanine
<220> FEATURE:
<221> NAME/KEY: VARIANT
<222> LOCATION: (39)
<223> OTHER INFORMATION: Xaa in position 39 is Ser, Thr or Tyr
<220> FEATURE:
<221> NAME/KEY: VARIANT
<222> LOCATION: (40)
<223> OTHER INFORMATION: Xaa in position 40 is -OH or -NH3, with the
      proviso that the compound does not have the formula of either
      SEQ. ID. NOS. 1 or 2

<400> SEQUENCE: 47

Xaa Xaa Xaa Gly Thr Xaa Xaa Xaa Xaa Xaa Ser Lys Gln Xaa Glu Glu
 1               5                   10                  15

Glu Ala Val Arg Leu Xaa Xaa Xaa Xaa Leu Lys Asn Gly Gly Xaa Ser
            20                  25                  30

Ser Gly Ala Xaa Xaa Xaa Xaa Xaa
        35                  40

<210> SEQ ID NO 48
<211> LENGTH: 40
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: VARIANT
<222> LOCATION: (1)
<223> OTHER INFORMATION: Xaa in position 1 is His, Arg, Tyr or
      4-imidazopropionyl
<220> FEATURE:
<221> NAME/KEY: VARIANT
<222> LOCATION: (2)
<223> OTHER INFORMATION: Xaa in position 2 is Ser, Gly, Ala or Thr
<220> FEATURE:
<221> NAME/KEY: VARIANT
<222> LOCATION: (3)
<223> OTHER INFORMATION: Xaa in position 3 is Asp or Glu
<220> FEATURE:
<221> NAME/KEY: VARIANT
```

```
<222> LOCATION: (6)
<223> OTHER INFORMATION: Xaa in position 6 is Phe, Tyr or
      naphthylalanine
<220> FEATURE:
<221> NAME/KEY: VARIANT
<222> LOCATION: (7)..(8)
<223> OTHER INFORMATION: Xaa in positions 7 & 8 is Thr or Ser
<220> FEATURE:
<221> NAME/KEY: VARIANT
<222> LOCATION: (9)
<223> OTHER INFORMATION: Xaa in position 9 is Asp or Glu
<220> FEATURE:
<221> NAME/KEY: VARIANT
<222> LOCATION: (10)
<223> OTHER INFORMATION: Xaa in position 10 is Leu, Ile, Val,
      pentylglycine or Met
<220> FEATURE:
<221> NAME/KEY: VARIANT
<222> LOCATION: (14)
<223> OTHER INFORMATION: Xaa at position 14 is Leu, Ile, pentylglycine,
      Val or Met
<220> FEATURE:
<221> NAME/KEY: VARIANT
<222> LOCATION: (22)
<223> OTHER INFORMATION: Xaa in position 22 is Phe, Tyr or
      naphthylalanine
<220> FEATURE:
<221> NAME/KEY: VARIANT
<222> LOCATION: (23)
<223> OTHER INFORMATION: Xaa in position 23 is Ile, Val, Lu,
      pentylglycine, tert-butylglycine or Met
<220> FEATURE:
<221> NAME/KEY: VARIANT
<222> LOCATION: (24)
<223> OTHER INFORMATION: Xaa in position 24 is Glu or Asp
<220> FEATURE:
<221> NAME/KEY: VARIANT
<222> LOCATION: (25)
<223> OTHER INFORMATION: Xaa in position 25 is Trp, Phe, Tyr, or
      naphthylalanine
<220> FEATURE:
<221> NAME/KEY: VARIANT
<222> LOCATION: (27)
<223> OTHER INFORMATION: Xaa in position 27 is Lys-Asn-Lys,
      Lys-NH3-R-Asn, Asn-Lys-NH3-R where R is Lys, Arg, C1-C10 straight
      chain or branched alkanoyl or cycloalkylalkanoyl
<220> FEATURE:
<221> NAME/KEY: VARIANT
<222> LOCATION: (30)
<223> OTHER INFORMATION: Xaa in position is independently Pro,
      homoproline, 3-hydroxyproline, 4-hydroxyproline, thioproline,
      N-alkylglycine, N-alkylpentylglycine or N-alkylalanine
<220> FEATURE:
<221> NAME/KEY: VARIANT
<222> LOCATION: (35)..(39)
<223> OTHER INFORMATION: Xaa in positions 35-39 is independently Pro,
      homoproline, 3-hydroxproline, 4-hydroxyproline, thioproline,
      N-alkylglycine, N-alkylpentylglycine or N-alkylalanine
<220> FEATURE:
<221> NAME/KEY: VARIANT
<222> LOCATION: (40)
<223> OTHER INFORMATION: Xaa in position 40 is -OH or NH2, with the
      proviso that the compound does not have the formula of either
      SEQ. ID. NOS. 1 or 2

<400> SEQUENCE: 48

Xaa Xaa Xaa Gly Thr Xaa Xaa Xaa Xaa Xaa Ser Lys Gln Xaa Glu Glu
  1               5                  10                  15

Glu Ala Val Arg Leu Xaa Xaa Xaa Xaa Leu Xaa Gly Gly Xaa Ser Ser
                 20                  25                  30

Gly Ala Xaa Xaa Xaa Xaa Xaa Xaa
             35                  40

<210> SEQ ID NO 49
<211> LENGTH: 30
```

```
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (30)
<223> OTHER INFORMATION: Gly in position 30 is amidated

<400> SEQUENCE: 49

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly
             20                  25                  30

<210> SEQ ID NO 50
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 50

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn
             20                  25

<210> SEQ ID NO 51
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 51

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn
             20                  25

<210> SEQ ID NO 52
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 52

His Ala Glu Gly Thr Phe Thr Ser Asp Leu Ser Lys Gln Leu Glu Glu
 1               5                  10                  15

Glu Ala Val Arg Leu Phe Ile Glu Phe Leu Lys Asn
```

```
                    20                  25
```

```
<210> SEQ ID NO 53
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 53

His Gly Glu Gly Ala Phe Thr Ser Asp Leu Ser Lys Gln Leu Glu Glu
 1               5                  10                  15

Glu Ala Val Arg Leu Phe Ile Glu Phe Leu Lys Asn
            20                  25

<210> SEQ ID NO 54
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 54

His Gly Glu Gly Thr Ala Thr Ser Asp Leu Ser Lys Gln Leu Glu Glu
 1               5                  10                  15

Glu Ala Val Arg Leu Phe Ile Glu Phe Leu Lys Asn
            20                  25

<210> SEQ ID NO 55
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 55

His Gly Glu Gly Thr Phe Thr Ala Asp Leu Ser Lys Gln Leu Glu Glu
 1               5                  10                  15

Glu Ala Val Arg Leu Phe Ile Glu Phe Leu Lys Asn
            20                  25

<210> SEQ ID NO 56
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 56
```

His Gly Glu Gly Thr Phe Thr Ser Asp Ala Ser Lys Gln Leu Glu Glu
1               5                   10                  15

Glu Ala Val Arg Leu Phe Ile Glu Phe Leu Lys Asn
            20                  25

<210> SEQ ID NO 57
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 57

His Gly Glu Gly Thr Phe Thr Ser Asp Leu Ala Lys Gln Leu Glu Glu
1               5                   10                  15

Glu Ala Val Arg Leu Phe Ile Glu Phe Leu Lys Asn
            20                  25

<210> SEQ ID NO 58
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 58

His Gly Glu Gly Thr Phe Thr Ser Asp Leu Ser Ala Gln Leu Glu Glu
1               5                   10                  15

Glu Ala Val Arg Leu Phe Ile Glu Phe Leu Lys Asn
            20                  25

<210> SEQ ID NO 59
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 59

His Gly Glu Gly Thr Phe Thr Ser Asp Leu Ser Lys Ala Leu Glu Glu
1               5                   10                  15

Glu Ala Val Arg Leu Phe Ile Glu Phe Leu Lys Asn
            20                  25

<210> SEQ ID NO 60
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:

```
<221> NAME/KEY: AMIDATION
<222> LOCATION: (28)
<223> OTHER INFORMATION: Asn in position 28 is amidated

<400> SEQUENCE: 60

His Gly Glu Gly Thr Phe Thr Ser Asp Leu Ser Lys Gln Ala Glu Glu
 1               5                  10                  15

Glu Ala Val Arg Leu Phe Ile Glu Phe Leu Lys Asn
            20                  25

<210> SEQ ID NO 61
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 61

His Gly Glu Gly Thr Phe Thr Ser Asp Leu Ser Lys Gln Leu Ala Glu
 1               5                  10                  15

Glu Ala Val Arg Leu Phe Ile Glu Phe Leu Lys Asn
            20                  25

<210> SEQ ID NO 62
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 62

His Gly Glu Gly Thr Phe Thr Ser Asp Leu Ser Lys Gln Leu Glu Ala
 1               5                  10                  15

Glu Ala Val Arg Leu Phe Ile Glu Phe Leu Lys Asn
            20                  25

<210> SEQ ID NO 63
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 63

His Gly Glu Gly Thr Phe Thr Ser Asp Leu Ser Lys Gln Leu Glu Glu
 1               5                  10                  15

Ala Ala Val Arg Leu Phe Ile Glu Phe Leu Lys Asn
            20                  25

<210> SEQ ID NO 64
<211> LENGTH: 28
<212> TYPE: PRT
```

```
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 64

His Gly Glu Gly Thr Phe Thr Ser Asp Leu Ser Lys Gln Leu Glu Glu
 1               5                  10                  15

Glu Ala Ala Arg Leu Phe Ile Glu Phe Leu Lys Asn
            20                  25

<210> SEQ ID NO 65
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 65

His Gly Glu Gly Thr Phe Thr Ser Asp Leu Ser Lys Gln Leu Glu Glu
 1               5                  10                  15

Glu Ala Val Ala Leu Phe Ile Glu Phe Leu Lys Asn
            20                  25

<210> SEQ ID NO 66
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 66

His Gly Glu Gly Thr Phe Thr Ser Asp Leu Ser Lys Gln Leu Glu Glu
 1               5                  10                  15

Glu Ala Val Arg Ala Phe Ile Glu Phe Leu Lys Asn
            20                  25

<210> SEQ ID NO 67
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 67

His Gly Glu Gly Thr Phe Thr Ser Asp Leu Ser Lys Gln Leu Glu Glu
 1               5                  10                  15

Glu Ala Val Arg Leu Phe Ile Ala Phe Leu Lys Asn
            20                  25
```

```
<210> SEQ ID NO 68
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 68

His Gly Glu Gly Thr Phe Thr Ser Asp Leu Ser Lys Gln Leu Glu Glu
1               5                   10                  15

Glu Ala Val Arg Leu Phe Ile Glu Ala Leu Lys Asn
            20                  25

<210> SEQ ID NO 69
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 69

His Gly Glu Gly Thr Phe Thr Ser Asp Leu Ser Lys Gln Leu Glu Glu
1               5                   10                  15

Glu Ala Val Arg Leu Phe Ile Glu Phe Ala Lys Asn
            20                  25

<210> SEQ ID NO 70
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 70

His Gly Glu Gly Thr Phe Thr Ser Asp Leu Ser Lys Gln Leu Glu Glu
1               5                   10                  15

Glu Ala Val Arg Leu Phe Ile Glu Phe Leu Ala Asn
            20                  25

<210> SEQ ID NO 71
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Ala in position 28 is amidated

<400> SEQUENCE: 71
```

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Ala
            20                  25

<210> SEQ ID NO 72
<211> LENGTH: 38
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (38)
<223> OTHER INFORMATION: Pro in position 38 is amidated

<400> SEQUENCE: 72

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro
        35

<210> SEQ ID NO 73
<211> LENGTH: 38
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (38)
<223> OTHER INFORMATION: Pro in position 38 is amidated

<400> SEQUENCE: 73

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Pro
        35

<210> SEQ ID NO 74
<211> LENGTH: 37
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (37)
<223> OTHER INFORMATION: Pro in position 37 is amidated

<400> SEQUENCE: 74

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro
        35

```
<210> SEQ ID NO 75
<211> LENGTH: 37
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (37)
<223> OTHER INFORMATION: Pro in position 37 is amidated

<400> SEQUENCE: 75

His Gly Glu Gly Thr Phe Thr Ser Asp Leu Ser Lys Gln Leu Glu Glu
  1               5                  10                  15

Glu Ala Val Arg Leu Phe Ile Glu Phe Leu Lys Asn Gly Gly Pro Ser
             20                  25                  30

Ser Gly Ala Pro Pro
         35

<210> SEQ ID NO 76
<211> LENGTH: 36
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (36)
<223> OTHER INFORMATION: Pro in position 36 is amidated

<400> SEQUENCE: 76

His Gly Glu Gly Thr Phe Thr Ser Asp Leu Ser Lys Gln Met Glu Glu
  1               5                  10                  15

Glu Ala Val Arg Leu Phe Ile Glu Trp Leu Lys Asn Gly Gly Pro Ser
             20                  25                  30

Ser Gly Ala Pro
         35

<210> SEQ ID NO 77
<211> LENGTH: 36
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (36)
<223> OTHER INFORMATION: Pro in position 36 is amidated

<400> SEQUENCE: 77

His Gly Glu Gly Thr Phe Thr Ser Asp Leu Ser Lys Gln Leu Glu Glu
  1               5                  10                  15

Glu Ala Val Arg Leu Phe Ile Glu Phe Leu Lys Asn Gly Gly Pro Ser
             20                  25                  30

Ser Gly Ala Pro
         35

<210> SEQ ID NO 78
<211> LENGTH: 35
<212> TYPE: PRT
<213> ORGANISM: Artificial Sequence
<220> FEATURE:
<223> OTHER INFORMATION: Description of Artificial Sequence: Synthetic
      Amino Acid Sequence
```

```
<220> FEATURE:
<221> NAME/KEY: AMIDATION
<222> LOCATION: (35)
<223> OTHER INFORMATION: Ala in position 35 is amidated

<400> SEQUENCE: 78

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala
        35

<210> SEQ ID NO 79
<211> LENGTH: 35
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (35)
<223> OTHER INFORMATION: Ala in position 35 is amidated

<400> SEQUENCE: 79

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly Pro Ser
            20                  25                  30

Ser Gly Ala
        35

<210> SEQ ID NO 80
<211> LENGTH: 34
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (34)
<223> OTHER INFORMATION: Gly in position 34 is amidated

<400> SEQUENCE: 80

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly

<210> SEQ ID NO 81
<211> LENGTH: 34
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (34)
<223> OTHER INFORMATION: Gly in position 34 is amidated

<400> SEQUENCE: 81

His Gly Glu Gly Thr Phe Thr Ser Asp Leu Ser Lys Gln Leu Glu Glu
```

-continued

```
                1               5                  10                 15
Glu Ala Val Arg Leu Phe Ile Glu Phe Leu Lys Asn Gly Gly Pro Ser
                20                  25                 30

Ser Gly

<210> SEQ ID NO 82
<211> LENGTH: 33
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (33)
<223> OTHER INFORMATION: Ser in position 33 is amidated

<400> SEQUENCE: 82

His Gly Glu Gly Thr Phe Thr Ser Asp Leu Ser Lys Gln Met Glu Glu
  1               5                  10                 15
Glu Ala Val Arg Leu Phe Ile Glu Trp Leu Lys Asn Gly Gly Pro Ser
                20                  25                 30

Ser

<210> SEQ ID NO 83
<211> LENGTH: 33
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (33)
<223> OTHER INFORMATION: Ser in position 33 is amidated

<400> SEQUENCE: 83

His Gly Glu Gly Thr Phe Thr Ser Asp Leu Ser Lys Gln Leu Glu Glu
  1               5                  10                 15
Glu Ala Val Arg Leu Phe Ile Glu Phe Leu Lys Asn Gly Gly Pro Ser
                20                  25                 30

Ser

<210> SEQ ID NO 84
<211> LENGTH: 32
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (32)
<223> OTHER INFORMATION: Ser in position 32 is amidated

<400> SEQUENCE: 84

His Gly Glu Gly Thr Phe Thr Ser Asp Leu Ser Lys Gln Met Glu Glu
  1               5                  10                 15
Glu Ala Val Arg Leu Phe Ile Glu Trp Leu Lys Asn Gly Gly Pro Ser
                20                  25                 30

<210> SEQ ID NO 85
<211> LENGTH: 32
<212> TYPE: PRT
<213> ORGANISM: Artificial Sequence
```

```
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (32)
<223> OTHER INFORMATION: Ser in position 32 is amidated

<400> SEQUENCE: 85

His Gly Glu Gly Thr Phe Thr Ser Asp Leu Ser Lys Gln Leu Glu Glu
  1               5                  10                  15

Glu Ala Val Arg Leu Phe Ile Glu Phe Leu Lys Asn Gly Gly Pro Ser
             20                  25                  30

<210> SEQ ID NO 86
<211> LENGTH: 31
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (31)
<223> OTHER INFORMATION: Pro in position 31 is amidated

<400> SEQUENCE: 86

His Gly Glu Gly Thr Phe Thr Ser Asp Leu Ser Lys Gln Met Glu Glu
  1               5                  10                  15

Glu Ala Val Arg Leu Phe Ile Glu Trp Leu Lys Asn Gly Gly Pro
             20                  25                  30

<210> SEQ ID NO 87
<211> LENGTH: 31
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (31)
<223> OTHER INFORMATION: Pro in position 31 is amidated

<400> SEQUENCE: 87

His Gly Glu Gly Thr Phe Thr Ser Asp Leu Ser Lys Gln Leu Glu Glu
  1               5                  10                  15

Glu Ala Val Arg Leu Phe Ile Glu Phe Leu Lys Asn Gly Gly Pro
             20                  25                  30

<210> SEQ ID NO 88
<211> LENGTH: 30
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (30)
<223> OTHER INFORMATION: Gly in position 30 is amidated

<400> SEQUENCE: 88

His Gly Glu Gly Thr Phe Thr Ser Asp Leu Ser Lys Gln Leu Glu Glu
  1               5                  10                  15

Glu Ala Val Arg Leu Phe Ile Glu Phe Leu Lys Asn Gly Gly
             20                  25                  30
```

```
<210> SEQ ID NO 89
<211> LENGTH: 29
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (29)
<223> OTHER INFORMATION: Gly in position 29 is amidated

<400> SEQUENCE: 89

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly
            20                  25

<210> SEQ ID NO 90
<211> LENGTH: 29
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (29)
<223> OTHER INFORMATION: Gly in position 29 is amidated

<400> SEQUENCE: 90

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn Gly
            20                  25

<210> SEQ ID NO 91
<211> LENGTH: 38
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (31)
<223> OTHER INFORMATION: Xaa in position 31 is tPro
<220> FEATURE:
<221> NAME/KEY: VARIANT
<222> LOCATION: (36)..(38)
<223> OTHER INFORMATION: Xaa in positions 36-38 is tPro
<220> FEATURE:
<221> NAME/KEY: AMIDATION
<222> LOCATION: (38)
<223> OTHER INFORMATION: tPro in postion 38 is amidated

<400> SEQUENCE: 91

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Xaa Ser
            20                  25                  30

Ser Gly Ala Xaa Xaa Xaa
        35

<210> SEQ ID NO 92
<211> LENGTH: 38
<212> TYPE: PRT
<213> ORGANISM: Artificial Sequence
```

```
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (36)...(38)
<223> OTHER INFORMATION: Xaa in positions 36-38 is tPro
<220> FEATURE:
<221> NAME/KEY: AMIDATION
<222> LOCATION: (38)
<223> OTHER INFORMATION: tPro in position 38 is amidated

<400> SEQUENCE: 92

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Xaa Xaa Xaa
        35

<210> SEQ ID NO 93
<211> LENGTH: 37
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (31)
<223> OTHER INFORMATION: Xaa in position 31 stands for Nme
<220> FEATURE:
<221> NAME/KEY: AMIDATION
<222> LOCATION: (37)
<223> OTHER INFORMATION: Pro in position 37 is amidated

<400> SEQUENCE: 93

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Xaa Ser
            20                  25                  30

Ser Gly Ala Pro Pro
        35

<210> SEQ ID NO 94
<211> LENGTH: 37
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (31)
<223> OTHER INFORMATION: Xaa in position 31 is Nme
<220> FEATURE:
<221> NAME/KEY: VARIANT
<222> LOCATION: (36)..(37)
<223> OTHER INFORMATION: Xaa in positions 36-37 is Nme
<220> FEATURE:
<221> NAME/KEY: AMIDATION
<222> LOCATION: (37)
<223> OTHER INFORMATION: Nme in position 37 is amidated

<400> SEQUENCE: 94

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Xaa Ser
            20                  25                  30
```

Ser Gly Ala Xaa Xaa
        35

<210> SEQ ID NO 95
<211> LENGTH: 37
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (31)
<223> OTHER INFORMATION: Xaa in position 31 stands for hPro
<220> FEATURE:
<221> NAME/KEY: VARIANT
<222> LOCATION: (36)..(37)
<223> OTHER INFORMATION: Xaa in positions 36-37 stands for hPro
<220> FEATURE:
<221> NAME/KEY: AMIDATION
<222> LOCATION: (37)
<223> OTHER INFORMATION: hPro in position 37 is amidated

<400> SEQUENCE: 95

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Xaa Ser
            20                  25                  30

Ser Gly Ala Xaa Xaa
        35

<210> SEQ ID NO 96
<211> LENGTH: 36
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (31)
<223> OTHER INFORMATION: Xaa in position 31 stands for hPro
<220> FEATURE:
<221> NAME/KEY: VARIANT
<222> LOCATION: (36)
<223> OTHER INFORMATION: Xaa in position 36 stands for hPro
<220> FEATURE:
<221> NAME/KEY: AMIDATION
<222> LOCATION: (36)
<223> OTHER INFORMATION: hPro in position 36 is amidated

<400> SEQUENCE: 96

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Xaa Ser
            20                  25                  30

Ser Gly Ala Xaa
        35

<210> SEQ ID NO 97
<211> LENGTH: 35
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (35)

<223> OTHER INFORMATION: Ala in position 35 is amidated

<400> SEQUENCE: 97

Arg Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala
        35

<210> SEQ ID NO 98
<211> LENGTH: 30
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (30)
<223> OTHER INFORMATION: Gly in position 30 is amidated

<400> SEQUENCE: 98

His Gly Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly
            20                  25                  30

<210> SEQ ID NO 99
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (6)
<223> OTHER INFORMATION: Xaa in position 6 stands for naph
<220> FEATURE:
<221> NAME/KEY: AMIDATION
<222> LOCATION: (28)
<223> OTHER INFORMATION: Asn in position 28 is amidated

<400> SEQUENCE: 99

His Gly Glu Gly Thr Xaa Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 100
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 100

His Gly Glu Gly Thr Phe Ser Ser Asp Leu Ser Lys Gln Met Glu Glu
1               5                   10                  15

Glu Ala Val Arg Leu Phe Ile Glu Trp Leu Lys Asn
            20                  25

```
<210> SEQ ID NO 101
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 101

His Gly Glu Gly Thr Phe Ser Thr Asp Leu Ser Lys Gln Met Glu Glu
 1               5                  10                  15

Glu Ala Val Arg Leu Phe Ile Glu Trp Leu Lys Asn
            20                  25

<210> SEQ ID NO 102
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 102

His Gly Glu Gly Thr Phe Thr Ser Glu Leu Ser Lys Gln Met Ala Glu
 1               5                  10                  15

Glu Ala Val Arg Leu Phe Ile Glu Trp Leu Lys Asn
            20                  25

<210> SEQ ID NO 103
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (10)
<223> OTHER INFORMATION: Xaa in position 10 stands for pGly
<220> FEATURE:
<221> NAME/KEY: AMIDATION
<222> LOCATION: (28)
<223> OTHER INFORMATION: Asn in position 28 is amidated

<400> SEQUENCE: 103

His Gly Glu Gly Thr Phe Thr Ser Asp Xaa Ser Lys Gln Leu Glu Glu
 1               5                  10                  15

Glu Ala Val Arg Leu Phe Ile Glu Phe Leu Lys Asn
            20                  25

<210> SEQ ID NO 104
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (22)
```

```
<223> OTHER INFORMATION: Xaa in position 22 stands for naph
<220> FEATURE:
<221> NAME/KEY: AMIDATION
<222> LOCATION: (28)
<223> OTHER INFORMATION: Asn in position 28 is amidated

<400> SEQUENCE: 104

His Gly Glu Gly Thr Phe Thr Ser Asp Leu Ser Lys Gln Leu Glu Glu
 1               5                  10                  15

Glu Ala Val Arg Leu Xaa Ile Glu Phe Leu Lys Asn
            20                  25

<210> SEQ ID NO 105
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (23)
<223> OTHER INFORMATION: Xaa in position 23 stands for tBug
<220> FEATURE:
<221> NAME/KEY: AMIDATION
<222> LOCATION: (28)
<223> OTHER INFORMATION: Asn in position 28 is amidated

<400> SEQUENCE: 105

His Gly Glu Gly Thr Phe Thr Ser Asp Leu Ser Lys Gln Met Glu Glu
 1               5                  10                  15

Glu Ala Val Arg Leu Phe Xaa Glu Trp Leu Lys Asn
            20                  25

<210> SEQ ID NO 106
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 106

His Gly Glu Gly Thr Phe Thr Ser Asp Leu Ser Lys Gln Leu Glu Glu
 1               5                  10                  15

Glu Ala Val Arg Leu Phe Ile Asp Phe Leu Lys Asn
            20                  25

<210> SEQ ID NO 107
<211> LENGTH: 33
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (33)
<223> OTHER INFORMATION: Ser in position 33 is amidated

<400> SEQUENCE: 107

His Gly Glu Gly Thr Phe Thr Ser Asp Ala Ser Lys Gln Leu Glu Glu
 1               5                  10                  15

Glu Ala Val Arg Leu Phe Ile Glu Phe Leu Lys Asn Gly Gly Pro Ser
```

Ser

<210> SEQ ID NO 108
<211> LENGTH: 29
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (29)
<223> OTHER INFORMATION: Gly in position 29 is amidated

<400> SEQUENCE: 108

His Gly Glu Gly Thr Phe Thr Ser Asp Ala Ser Lys Gln Met Glu Glu
  1               5                  10                  15

Glu Ala Val Arg Leu Phe Ile Glu Trp Leu Lys Asn Gly
             20                  25

<210> SEQ ID NO 109
<211> LENGTH: 37
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (31)
<223> OTHER INFORMATION: Xaa in position 31 stands for hPro
<220> FEATURE:
<221> NAME/KEY: VARIANT
<222> LOCATION: (36)..(37)
<223> OTHER INFORMATION: Xaa in positions 36-37 stands for hPro
<220> FEATURE:
<221> NAME/KEY: AMIDATION
<222> LOCATION: (37)
<223> OTHER INFORMATION: hPro in position 37 is amidated

<400> SEQUENCE: 109

His Gly Glu Gly Thr Phe Thr Ser Asp Ala Ser Lys Gln Met Glu Glu
  1               5                  10                  15

Glu Ala Val Arg Leu Phe Ile Glu Trp Leu Lys Asn Gly Gly Xaa Ser
             20                  25                  30

Ser Gly Ala Xaa Xaa
         35

<210> SEQ ID NO 110
<211> LENGTH: 27
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (1)
<223> OTHER INFORMATION: Xaa in position 1 stands for
      4-Imidazolylpropionyl-Gly
<220> FEATURE:
<221> NAME/KEY: VARIANT
<222> LOCATION: (26)
<223> OTHER INFORMATION: Xaa in position 26 stands for Lys-NH(epsilon)
      octanoyl
<220> FEATURE:
<221> NAME/KEY: AMIDATION
<222> LOCATION: (27)
<223> OTHER INFORMATION: Asn in position 27 is amidated

```
<400> SEQUENCE: 110

Xaa Glu Gly Thr Phe Thr Ser Asp Leu Ser Lys Gln Met Glu Glu Glu
 1               5                  10                  15

Ala Val Arg Leu Phe Ile Glu Trp Leu Xaa Asn
            20                  25

<210> SEQ ID NO 111
<211> LENGTH: 27
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (1)
<223> OTHER INFORMATION: Xaa in position 1 stands for
      4-Imidazolylpropionyl-Gly
<220> FEATURE:
<221> NAME/KEY: VARIANT
<222> LOCATION: (26)
<223> OTHER INFORMATION: Xaa in position 26 stands for Lys-NH(epsilon)
      octanoyl
<220> FEATURE:
<221> NAME/KEY: AMIDATION
<222> LOCATION: (27)
<223> OTHER INFORMATION: Asn in position 27 is amidated

<400> SEQUENCE: 111

Xaa Glu Gly Thr Phe Thr Ser Asp Leu Ser Lys Gln Leu Glu Glu Glu
 1               5                  10                  15

Ala Val Arg Leu Phe Ile Glu Phe Leu Xaa Asn
            20                  25

<210> SEQ ID NO 112
<211> LENGTH: 29
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (1)
<223> OTHER INFORMATION: Xaa in position 1 stands for
      4-Imidazolylpropionyl-Gly
<220> FEATURE:
<221> NAME/KEY: VARIANT
<222> LOCATION: (26)
<223> OTHER INFORMATION: Xaa in position 26 stands for Lys-NH(epsilon)
      octanoyl
<220> FEATURE:
<221> NAME/KEY: AMIDATION
<222> LOCATION: (29)
<223> OTHER INFORMATION: Gly in position 29 is amidated

<400> SEQUENCE: 112

Xaa Glu Gly Thr Phe Thr Ser Asp Leu Ser Lys Gln Met Glu Glu Glu
 1               5                  10                  15

Ala Val Arg Leu Phe Ile Glu Trp Leu Xaa Asn Gly Gly
            20                  25

<210> SEQ ID NO 113
<211> LENGTH: 29
<212> TYPE: PRT
<213> ORGANISM: Artificial Sequence
<220> FEATURE:
<223> OTHER INFORMATION: Description of Artificial Sequence: Synthetic
      Amino Acid Sequence
```

```
<220> FEATURE:
<221> NAME/KEY: VARIANT
<222> LOCATION: (1)
<223> OTHER INFORMATION: Xaa in position 1 stands for
      4-Imidazolylpropionyl-Gly
<220> FEATURE:
<221> NAME/KEY: VARIANT
<222> LOCATION: (26)
<223> OTHER INFORMATION: Xaa in position 26 stands for Lys-NH(epsilon)
      octanoyl
<220> FEATURE:
<221> NAME/KEY: AMIDATION
<222> LOCATION: (29)
<223> OTHER INFORMATION: Gly in position 29 is amidated

<400> SEQUENCE: 113

Xaa Gln Gly Thr Phe Thr Ser Asp Leu Ser Lys Gln Leu Glu Glu Glu
 1               5                  10                  15

Ala Val Arg Leu Phe Ile Glu Phe Leu Xaa Asn Gly Gly
            20                  25

<210> SEQ ID NO 114
<211> LENGTH: 27
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (1)
<223> OTHER INFORMATION: Xaa in position 1 stands for
      4-Imidazolylpropionyl-Gly
<220> FEATURE:
<221> NAME/KEY: VARIANT
<222> LOCATION: (27)
<223> OTHER INFORMATION: Xaa in position 27 stands for Lys-NH(epsilon)
      octanoyl
<220> FEATURE:
<221> NAME/KEY: AMIDATION
<222> LOCATION: (27)
<223> OTHER INFORMATION: Lys-NH(epsilon) octanoyl in position 27 is
      amidated

<400> SEQUENCE: 114

Xaa Glu Gly Thr Phe Thr Ser Asp Leu Ser Lys Gln Met Glu Glu Glu
 1               5                  10                  15

Ala Val Arg Leu Phe Ile Glu Trp Leu Asn Xaa
            20                  25

<210> SEQ ID NO 115
<211> LENGTH: 27
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (1)
<223> OTHER INFORMATION: Xaa in position 1 stands for
      4-Imidazolylpropionyl-Gly
<220> FEATURE:
<221> NAME/KEY: VARIANT
<222> LOCATION: (27)
<223> OTHER INFORMATION: Xaa in position 27 stands for Lys-NH(epsilon)
      octanoyl
<220> FEATURE:
<221> NAME/KEY: AMIDATION
<222> LOCATION: (27)
<223> OTHER INFORMATION: Lys-NH(epsilon) octanoyl in position 27 is
      amidated
```

```
<400> SEQUENCE: 115

Xaa Glu Gly Thr Phe Thr Ser Asp Leu Ser Lys Gln Leu Glu Glu Glu
 1               5                  10                  15

Ala Val Arg Leu Phe Ile Glu Phe Leu Asn Xaa
            20                  25

<210> SEQ ID NO 116
<211> LENGTH: 29
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (1)
<223> OTHER INFORMATION: Xaa in position 1 stands for
      4-Imidazolylpropionyl-Gly
<220> FEATURE:
<221> NAME/KEY: VARIANT
<222> LOCATION: (27)
<223> OTHER INFORMATION: Xaa in position 27 stands for Lys-NH(epsilon)
      octanoyl
<220> FEATURE:
<221> NAME/KEY: AMIDATION
<222> LOCATION: (29)
<223> OTHER INFORMATION: Gly in position 29 is amidated

<400> SEQUENCE: 116

Xaa Glu Gly Thr Phe Thr Ser Asp Leu Ser Lys Gln Met Glu Glu Glu
 1               5                  10                  15

Ala Val Arg Leu Phe Ile Glu Trp Leu Asn Xaa Gly Gly
            20                  25

<210> SEQ ID NO 117
<211> LENGTH: 29
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (1)
<223> OTHER INFORMATION: Xaa in position 1 stands for
      4-Imidazolylpropionyl-Gly
<220> FEATURE:
<221> NAME/KEY: VARIANT
<222> LOCATION: (27)
<223> OTHER INFORMATION: Xaa in position 27 stands for Lys-NH(epsilon)
      octanoyl
<220> FEATURE:
<221> NAME/KEY: AMIDATION
<222> LOCATION: (29)
<223> OTHER INFORMATION: Gly in postion 29 is amidated

<400> SEQUENCE: 117

Xaa Glu Gly Thr Phe Thr Ser Asp Leu Ser Lys Gln Leu Glu Glu Glu
 1               5                  10                  15

Ala Val Arg Leu Phe Ile Glu Phe Leu Asn Xaa Gly Gly
            20                  25

<210> SEQ ID NO 118
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
```

<221> NAME/KEY: AMIDATION
<222> LOCATION: (28)
<223> OTHER INFORMATION: Asn in position 28 is amidated

<400> SEQUENCE: 118

Ala Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn
            20                  25

<210> SEQ ID NO 119
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 119

His Gly Ala Gly Thr Phe Thr Ser Asp Leu Ser Lys Gln Leu Glu Glu
 1               5                  10                  15

Glu Ala Val Arg Leu Phe Ile Glu Phe Leu Lys Asn
            20                  25

<210> SEQ ID NO 120
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 120

His Gly Glu Ala Thr Phe Thr Ser Asp Leu Ser Lys Gln Leu Glu Glu
 1               5                  10                  15

Glu Ala Val Arg Leu Phe Ile Glu Phe Leu Lys Asn
            20                  25

<210> SEQ ID NO 121
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 121

His Gly Glu Gly Thr Phe Thr Ser Ala Leu Ser Lys Gln Leu Glu Glu
 1               5                  10                  15

Glu Ala Val Arg Leu Phe Ile Glu Phe Leu Lys Asn
            20                  25

<210> SEQ ID NO 122
<211> LENGTH: 28
<212> TYPE: PRT

```
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 122

Ala Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn
            20                  25

<210> SEQ ID NO 123
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 123

His Gly Ala Gly Thr Phe Thr Ser Asp Leu Ser Lys Gln Met Glu Glu
 1               5                  10                  15

Glu Ala Val Arg Leu Phe Ile Glu Trp Leu Lys Asn
            20                  25

<210> SEQ ID NO 124
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 124

His Gly Glu Ala Thr Phe Thr Ser Asp Leu Ser Lys Gln Met Glu Glu
 1               5                  10                  15

Glu Ala Val Arg Leu Phe Ile Glu Trp Leu Lys Asn
            20                  25

<210> SEQ ID NO 125
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 125

His Gly Glu Gly Thr Phe Thr Ser Ala Leu Ser Lys Gln Met Glu Glu
 1               5                  10                  15

Glu Ala Val Arg Leu Phe Ile Glu Trp Leu Lys Asn
            20                  25
```

```
<210> SEQ ID NO 126
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 126

His Gly Glu Gly Thr Phe Thr Ser Asp Ala Ser Lys Gln Met Glu Glu
 1               5                  10                  15

Glu Ala Val Arg Leu Phe Ile Glu Trp Leu Lys Asn
            20                  25

<210> SEQ ID NO 127
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 127

Ala Ala Glu Gly Thr Phe Thr Ser Asp Leu Ser Lys Gln Met Glu Glu
 1               5                  10                  15

Glu Ala Val Arg Leu Phe Ile Glu Trp Leu Lys Asn
            20                  25

<210> SEQ ID NO 128
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 128

Ala Ala Glu Gly Thr Phe Thr Ser Asp Leu Ser Lys Gln Leu Glu Glu
 1               5                  10                  15

Glu Ala Val Arg Leu Phe Ile Glu Phe Leu Lys Asn
            20                  25

<210> SEQ ID NO 129
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 129
```

```
Ala Gly Asp Gly Thr Phe Thr Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 130
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 130

Ala Gly Asp Gly Thr Phe Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 131
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 131

Ala Gly Asp Gly Ala Phe Thr Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 132
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 132

Ala Gly Asp Gly Ala Phe Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 133
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
```

```
<222> LOCATION: (6)
<223> OTHER INFORMATION: Xaa in position 6 stands for Nala
<220> FEATURE:
<221> NAME/KEY: AMIDATION
<222> LOCATION: (28)
<223> OTHER INFORMATION: Asn in position 28 is amidated

<400> SEQUENCE: 133

Ala Gly Asp Gly Thr Xaa Thr Ser Asp Leu Ser Lys Gln Met Glu Glu
 1               5                  10                  15

Glu Ala Val Arg Leu Phe Ile Glu Trp Leu Lys Asn
            20                  25

<210> SEQ ID NO 134
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (6)
<223> OTHER INFORMATION: Xaa in position 6 stands for Nala
<220> FEATURE:
<221> NAME/KEY: AMIDATION
<222> LOCATION: (28)
<223> OTHER INFORMATION: Asn in position 28 is amidated

<400> SEQUENCE: 134

Ala Gly Asp Gly Thr Xaa Thr Ser Asp Leu Ser Lys Gln Leu Glu Glu
 1               5                  10                  15

Glu Ala Val Arg Leu Phe Ile Glu Phe Leu Lys Asn
            20                  25

<210> SEQ ID NO 135
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 135

Ala Gly Asp Gly Thr Phe Ser Ser Asp Leu Ser Lys Gln Met Glu Glu
 1               5                  10                  15

Glu Ala Val Arg Leu Phe Ile Glu Trp Leu Lys Asn
            20                  25

<210> SEQ ID NO 136
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 136

Ala Gly Asp Gly Thr Phe Ser Ser Asp Leu Ser Lys Gln Leu Glu Glu
 1               5                  10                  15
```

Glu Ala Val Arg Leu Phe Ile Glu Phe Leu Lys Asn
            20                  25

<210> SEQ ID NO 137
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 137

Ala Gly Asp Gly Thr Phe Thr Ala Asp Leu Ser Lys Gln Met Glu Glu
1               5                   10                  15

Glu Ala Val Arg Leu Phe Ile Glu Trp Leu Lys Asn
            20                  25

<210> SEQ ID NO 138
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 138

Ala Gly Asp Gly Thr Phe Thr Ala Asp Leu Ser Lys Gln Leu Glu Glu
1               5                   10                  15

Glu Ala Val Arg Leu Phe Ile Glu Phe Leu Lys Asn
            20                  25

<210> SEQ ID NO 139
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 139

Ala Gly Asp Gly Thr Phe Thr Ser Ala Leu Ser Lys Gln Met Glu Glu
1               5                   10                  15

Glu Ala Val Arg Leu Phe Ile Glu Trp Leu Lys Asn
            20                  25

<210> SEQ ID NO 140
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

```
<400> SEQUENCE: 140

Ala Gly Asp Gly Thr Phe Thr Ser Ala Leu Ser Lys Gln Leu Glu Glu
1               5                   10                  15

Glu Ala Val Arg Leu Phe Ile Glu Phe Leu Lys Asn
            20                  25

<210> SEQ ID NO 141
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 141

Ala Gly Asp Gly Thr Phe Thr Ser Glu Leu Ser Lys Gln Met Glu Glu
1               5                   10                  15

Glu Ala Val Arg Leu Phe Ile Glu Trp Leu Lys Asn
            20                  25

<210> SEQ ID NO 142
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 142

Ala Gly Asp Gly Thr Phe Thr Ser Glu Leu Ser Lys Gln Leu Glu Glu
1               5                   10                  15

Glu Ala Val Arg Leu Phe Ile Glu Phe Leu Lys Asn
            20                  25

<210> SEQ ID NO 143
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 143

Ala Gly Asp Gly Thr Phe Thr Ser Asp Ala Ser Lys Gln Met Glu Glu
1               5                   10                  15

Glu Ala Val Arg Leu Phe Ile Glu Trp Leu Lys Asn
            20                  25

<210> SEQ ID NO 144
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
```

```
<220> FEATURE:
<221> NAME/KEY: AMIDATION
<222> LOCATION: (28)
<223> OTHER INFORMATION: Asn in position 28 is amidated

<400> SEQUENCE: 144

Ala Gly Asp Gly Thr Phe Thr Ser Asp Ala Ser Lys Gln Leu Glu Glu
1               5                   10                  15

Glu Ala Val Arg Leu Phe Ile Glu Phe Leu Lys Asn
            20                  25

<210> SEQ ID NO 145
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (10)
<223> OTHER INFORMATION: Xaa in position 10 stands for Pgly
<220> FEATURE:
<221> NAME/KEY: AMIDATION
<222> LOCATION: (28)
<223> OTHER INFORMATION: Asn in position 28 is amidated

<400> SEQUENCE: 145

Ala Gly Asp Gly Thr Phe Thr Ser Asp Xaa Ser Lys Gln Met Glu Glu
1               5                   10                  15

Glu Ala Val Arg Leu Phe Ile Glu Trp Leu Lys Asn
            20                  25

<210> SEQ ID NO 146
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (10)
<223> OTHER INFORMATION: Xaa in position 10 stands for Pgly
<220> FEATURE:
<221> NAME/KEY: AMIDATION
<222> LOCATION: (28)
<223> OTHER INFORMATION: Asn in position 28 is amidated

<400> SEQUENCE: 146

Ala Gly Asp Gly Thr Phe Thr Ser Asp Xaa Ser Lys Gln Leu Glu Glu
1               5                   10                  15

Glu Ala Val Arg Leu Phe Ile Glu Phe Leu Lys Asn
            20                  25

<210> SEQ ID NO 147
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 147

Ala Gly Asp Gly Thr Phe Thr Ser Asp Leu Ala Lys Gln Met Glu Glu
```

```
                1               5              10              15
Glu Ala Val Arg Leu Phe Ile Glu Trp Leu Lys Asn
                20                              25

<210> SEQ ID NO 148
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 148

Ala Gly Asp Gly Thr Phe Thr Ser Asp Leu Ala Lys Gln Leu Glu Glu
1               5                   10                  15
Glu Ala Val Arg Leu Phe Ile Glu Phe Leu Lys Asn
                20                              25

<210> SEQ ID NO 149
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 149

Ala Gly Asp Gly Thr Phe Thr Ser Asp Leu Ser Ala Gln Met Glu Glu
1               5                   10                  15
Glu Ala Val Arg Leu Phe Ile Glu Trp Leu Lys Asn
                20                              25

<210> SEQ ID NO 150
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 150

Ala Gly Asp Gly Thr Phe Thr Ser Asp Leu Ser Ala Gln Leu Glu Glu
1               5                   10                  15
Glu Ala Val Arg Leu Phe Ile Glu Phe Leu Lys Asn
                20                              25

<210> SEQ ID NO 151
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
```

<223> OTHER INFORMATION: Asn in position 28 is amidated

<400> SEQUENCE: 151

Ala Gly Asp Gly Thr Phe Thr Ser Asp Leu Ser Lys Ala Met Glu Glu
1               5                   10                  15

Glu Ala Val Arg Leu Phe Ile Glu Trp Leu Lys Asn
            20                  25

<210> SEQ ID NO 152
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 152

Ala Gly Asp Gly Thr Phe Thr Ser Asp Leu Ser Lys Ala Leu Glu Glu
1               5                   10                  15

Glu Ala Val Arg Leu Phe Ile Glu Phe Leu Lys Asn
            20                  25

<210> SEQ ID NO 153
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 153

Ala Gly Asp Gly Thr Phe Thr Ser Asp Leu Ser Lys Gln Ala Glu Glu
1               5                   10                  15

Glu Ala Val Arg Leu Phe Ile Glu Trp Leu Lys Asn
            20                  25

<210> SEQ ID NO 154
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 154

Ala Gly Asp Gly Thr Phe Thr Ser Asp Leu Ser Lys Gln Ala Glu Glu
1               5                   10                  15

Glu Ala Val Arg Leu Phe Ile Glu Phe Leu Lys Asn
            20                  25

<210> SEQ ID NO 155
<211> LENGTH: 28
<212> TYPE: PRT
<213> ORGANISM: Artificial Sequence
<220> FEATURE:

```
<223> OTHER INFORMATION: Description of Artificial Sequence: Synthetic
      Amino Acid Sequence
<220> FEATURE:
<221> NAME/KEY: VARIANT
<222> LOCATION: (14)
<223> OTHER INFORMATION: Xaa in position 14 stands for pGly
<220> FEATURE:
<221> NAME/KEY: AMIDATION
<222> LOCATION: (28)
<223> OTHER INFORMATION: Asn in position 28 is amidated

<400> SEQUENCE: 155

Ala Gly Asp Gly Thr Phe Thr Ser Asp Leu Ser Lys Gln Xaa Glu Glu
 1               5                  10                  15

Glu Ala Val Arg Leu Phe Ile Glu Trp Leu Lys Asn
            20                  25

<210> SEQ ID NO 156
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (14)
<223> OTHER INFORMATION: Xaa in position 14 stands for pGly
<220> FEATURE:
<221> NAME/KEY: AMIDATION
<222> LOCATION: (28)
<223> OTHER INFORMATION: Asn in position 28 is amidated

<400> SEQUENCE: 156

Ala Gly Asp Gly Thr Phe Thr Ser Asp Leu Ser Lys Gln Xaa Glu Glu
 1               5                  10                  15

Glu Ala Val Arg Leu Phe Ile Glu Phe Leu Lys Asn
            20                  25

<210> SEQ ID NO 157
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 157

Ala Gly Asp Gly Thr Phe Thr Ser Asp Leu Ser Lys Gln Met Ala Glu
 1               5                  10                  15

Glu Ala Val Arg Leu Phe Ile Glu Trp Leu Lys Asn
            20                  25

<210> SEQ ID NO 158
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 158
```

```
Ala Gly Asp Gly Thr Phe Thr Ser Asp Leu Ser Lys Gln Leu Ala Glu
1               5                   10                  15

Glu Ala Val Arg Leu Phe Ile Glu Phe Leu Lys Asn
            20                  25

<210> SEQ ID NO 159
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 159

Ala Gly Asp Gly Thr Phe Thr Ser Asp Leu Ser Lys Gln Met Glu Ala
1               5                   10                  15

Glu Ala Val Arg Leu Phe Ile Glu Trp Leu Lys Asn
            20                  25

<210> SEQ ID NO 160
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 160

Ala Gly Asp Gly Thr Phe Thr Ser Asp Leu Ser Lys Gln Leu Glu Ala
1               5                   10                  15

Glu Ala Val Arg Leu Phe Ile Glu Phe Leu Lys Asn
            20                  25

<210> SEQ ID NO 161
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 161

Ala Gly Asp Gly Thr Phe Thr Ser Asp Leu Ser Lys Gln Met Glu Glu
1               5                   10                  15

Ala Ala Val Arg Leu Phe Ile Glu Trp Leu Lys Asn
            20                  25

<210> SEQ ID NO 162
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
```

```
<221> NAME/KEY: AMIDATION
<222> LOCATION: (28)
<223> OTHER INFORMATION: Asn in position 28 is amidated

<400> SEQUENCE: 162

Ala Gly Asp Gly Thr Phe Thr Ser Asp Leu Ser Lys Gln Leu Glu Glu
 1               5                  10                  15

Ala Ala Val Arg Leu Phe Ile Glu Phe Leu Lys Asn
            20                  25

<210> SEQ ID NO 163
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 163

Ala Gly Asp Gly Thr Phe Thr Ser Asp Leu Ser Lys Gln Met Glu Glu
 1               5                  10                  15

Glu Ala Ala Arg Leu Phe Ile Glu Trp Leu Lys Asn
            20                  25

<210> SEQ ID NO 164
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 164

Ala Gly Asp Gly Thr Phe Thr Ser Asp Leu Ser Lys Gln Leu Glu Glu
 1               5                  10                  15

Glu Ala Ala Arg Leu Phe Ile Glu Phe Leu Lys Asn
            20                  25

<210> SEQ ID NO 165
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 165

Ala Gly Asp Gly Thr Phe Thr Ser Asp Leu Ser Lys Gln Met Glu Glu
 1               5                  10                  15

Glu Ala Val Ala Leu Phe Ile Glu Trp Leu Lys Asn
            20                  25

<210> SEQ ID NO 166
<211> LENGTH: 28
<212> TYPE: PRT
```

```
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 166

Ala Gly Asp Gly Thr Phe Thr Ser Asp Leu Ser Lys Gln Leu Glu Glu
  1               5                  10                  15

Glu Ala Val Ala Leu Phe Ile Glu Phe Leu Lys Asn
            20                  25

<210> SEQ ID NO 167
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 167

Ala Gly Asp Gly Thr Phe Thr Ser Asp Leu Ser Lys Gln Met Glu Glu
  1               5                  10                  15

Glu Ala Val Arg Ala Phe Ile Glu Trp Leu Lys Asn
            20                  25

<210> SEQ ID NO 168
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 168

Ala Gly Asp Gly Thr Phe Thr Ser Asp Leu Ser Lys Gln Leu Glu Glu
  1               5                  10                  15

Glu Ala Val Arg Ala Phe Ile Glu Phe Leu Lys Asn
            20                  25

<210> SEQ ID NO 169
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (22)
<223> OTHER INFORMATION: Xaa in position 22 stands for Nala
<220> FEATURE:
<221> NAME/KEY: AMIDATION
<222> LOCATION: (28)
<223> OTHER INFORMATION: Asn in position 28 is amidated

<400> SEQUENCE: 169

Ala Gly Asp Gly Thr Phe Thr Ser Asp Leu Ser Lys Gln Met Glu Glu
```

```
                1               5                  10                 15
Glu Ala Val Arg Leu Xaa Ile Glu Trp Leu Lys Asn
                20                  25

<210> SEQ ID NO 170
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (22)
<223> OTHER INFORMATION: Xaa in position 22 stands for Nala
<220> FEATURE:
<221> NAME/KEY: AMIDATION
<222> LOCATION: (28)
<223> OTHER INFORMATION: Asn in position 28 is amidated

<400> SEQUENCE: 170

Ala Gly Asp Gly Thr Phe Thr Ser Asp Leu Ser Lys Gln Leu Glu Glu
1               5                  10                  15

Glu Ala Val Arg Leu Xaa Ile Glu Phe Leu Lys Asn
                20                  25

<210> SEQ ID NO 171
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 171

Ala Gly Asp Gly Thr Phe Thr Ser Asp Leu Ser Lys Gln Met Glu Glu
1               5                  10                  15

Glu Ala Val Arg Leu Phe Val Glu Trp Leu Lys Asn
                20                  25

<210> SEQ ID NO 172
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 172

Ala Gly Asp Gly Thr Phe Thr Ser Asp Leu Ser Lys Gln Leu Glu Glu
1               5                  10                  15

Glu Ala Val Arg Leu Phe Val Glu Phe Leu Lys Asn
                20                  25

<210> SEQ ID NO 173
<211> LENGTH: 28
<212> TYPE: PRT
<213> ORGANISM: Artificial Sequence
<220> FEATURE:
<223> OTHER INFORMATION: Description of Artificial Sequence: Synthetic
```

```
            Amino Acid Sequence
<220> FEATURE:
<221> NAME/KEY: VARIANT
<222> LOCATION: (23)
<223> OTHER INFORMATION: Xaa in position 23 stands for tGly
<220> FEATURE:
<221> NAME/KEY: AMIDATION
<222> LOCATION: (28)
<223> OTHER INFORMATION: Asn in position 28 is amidated

<400> SEQUENCE: 173

Ala Gly Asp Gly Thr Phe Thr Ser Asp Leu Ser Lys Gln Met Glu Glu
 1               5                  10                  15

Glu Ala Val Arg Leu Phe Xaa Glu Trp Leu Lys Asn
            20                  25

<210> SEQ ID NO 174
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (23)
<223> OTHER INFORMATION: Xaa in position 23 stands for tGly
<220> FEATURE:
<221> NAME/KEY: AMIDATION
<222> LOCATION: (28)
<223> OTHER INFORMATION: Asn in position 28 is amidated

<400> SEQUENCE: 174

Ala Gly Asp Gly Thr Phe Thr Ser Asp Leu Ser Lys Gln Leu Glu Glu
 1               5                  10                  15

Glu Ala Val Arg Leu Phe Xaa Glu Phe Leu Lys Asn
            20                  25

<210> SEQ ID NO 175
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 175

Ala Gly Asp Gly Thr Phe Thr Ser Asp Leu Ser Lys Gln Met Glu Glu
 1               5                  10                  15

Glu Ala Val Arg Leu Phe Ile Asp Trp Leu Lys Asn
            20                  25

<210> SEQ ID NO 176
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 176
```

```
Ala Gly Asp Gly Thr Phe Thr Ser Asp Leu Ser Lys Gln Leu Glu Glu
1               5                   10                  15

Glu Ala Val Arg Leu Phe Ile Asp Phe Leu Lys Asn
            20                  25
```

<210> SEQ ID NO 177
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 177

```
Ala Gly Asp Gly Thr Phe Thr Ser Asp Leu Ser Lys Gln Met Glu Glu
1               5                   10                  15

Glu Ala Val Arg Leu Phe Ile Glu Ala Leu Lys Asn
            20                  25
```

<210> SEQ ID NO 178
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 178

```
Ala Gly Asp Gly Thr Phe Thr Ser Asp Leu Ser Lys Gln Leu Glu Glu
1               5                   10                  15

Glu Ala Val Arg Leu Phe Ile Glu Ala Leu Lys Asn
            20                  25
```

<210> SEQ ID NO 179
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 179

```
Ala Gly Asp Gly Thr Phe Thr Ser Asp Leu Ser Lys Gln Met Glu Glu
1               5                   10                  15

Glu Ala Val Arg Leu Phe Ile Glu Trp Ala Lys Asn
            20                  25
```

<210> SEQ ID NO 180
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION

```
<222> LOCATION: (28)
<223> OTHER INFORMATION: Asn in position 28 is amidated

<400> SEQUENCE: 180

Ala Gly Asp Gly Thr Phe Thr Ser Asp Leu Ser Lys Gln Leu Glu Glu
1               5                   10                  15

Glu Ala Val Arg Leu Phe Ile Glu Phe Ala Lys Asn
            20                  25

<210> SEQ ID NO 181
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 181

Ala Gly Asp Gly Thr Phe Thr Ser Asp Leu Ser Lys Gln Met Glu Glu
1               5                   10                  15

Glu Ala Val Arg Leu Phe Ile Glu Trp Leu Ala Asn
            20                  25

<210> SEQ ID NO 182
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 182

Ala Gly Asp Gly Thr Phe Thr Ser Asp Leu Ser Lys Gln Leu Glu Glu
1               5                   10                  15

Glu Ala Val Arg Leu Phe Ile Glu Phe Leu Ala Asn
            20                  25

<210> SEQ ID NO 183
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Ala in position 28 is amidated

<400> SEQUENCE: 183

Ala Gly Asp Gly Thr Phe Thr Ser Asp Leu Ser Lys Gln Met Glu Glu
1               5                   10                  15

Glu Ala Val Arg Leu Phe Ile Glu Trp Leu Lys Ala
            20                  25

<210> SEQ ID NO 184
<211> LENGTH: 28
<212> TYPE: PRT
<213> ORGANISM: Artificial Sequence
```

```
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Ala in position 28 is amidated

<400> SEQUENCE: 184

Ala Gly Asp Gly Thr Phe Thr Ser Asp Leu Ser Lys Gln Leu Glu Glu
 1               5                  10                  15

Glu Ala Val Arg Leu Phe Ile Glu Phe Leu Lys Ala
            20                  25

<210> SEQ ID NO 185
<211> LENGTH: 38
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (38)
<223> OTHER INFORMATION: Pro in position 38 is amidated

<400> SEQUENCE: 185

Ala Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro
        35

<210> SEQ ID NO 186
<211> LENGTH: 38
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (38)
<223> OTHER INFORMATION: Pro in position 38 is amidated

<400> SEQUENCE: 186

His Gly Ala Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly Pro Ser
            20                  25                  30

Ser Gly Ala Pro Pro Pro
        35

<210> SEQ ID NO 187
<211> LENGTH: 37
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (37)
<223> OTHER INFORMATION: Pro in position 37 is amidated

<400> SEQUENCE: 187
```

```
His Gly Glu Ala Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro
        35

<210> SEQ ID NO 188
<211> LENGTH: 36
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (36)
<223> OTHER INFORMATION: Pro in position 36 is amidated

<400> SEQUENCE: 188

His Gly Glu Gly Thr Phe Thr Ser Ala Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro
        35

<210> SEQ ID NO 189
<211> LENGTH: 36
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (36)
<223> OTHER INFORMATION: Pro in position 36 is amidated

<400> SEQUENCE: 189

Ala Gly Glu Gly Thr Phe Thr Ser Asp Ala Ser Lys Gln Leu Glu Glu
 1               5                  10                  15

Glu Ala Val Arg Leu Phe Ile Glu Phe Leu Lys Asn Gly Gly Pro Ser
            20                  25                  30

Ser Gly Ala Pro
        35

<210> SEQ ID NO 190
<211> LENGTH: 35
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (35)
<223> OTHER INFORMATION: Ala in position 35 is amidated

<400> SEQUENCE: 190

Ala Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala
```

```
<210> SEQ ID NO 191
<211> LENGTH: 35
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (35)
<223> OTHER INFORMATION: Ala in position 35 is amidated

<400> SEQUENCE: 191

His Gly Ala Gly Thr Phe Thr Ser Asp Leu Ser Lys Gln Leu Glu Glu
  1               5                  10                  15

Glu Ala Val Arg Leu Phe Ile Glu Phe Leu Lys Asn Gly Gly Pro Ser
             20                  25                  30

Ser Gly Ala
        35

<210> SEQ ID NO 192
<211> LENGTH: 34
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (34)
<223> OTHER INFORMATION: Gly in position 34 is amidated

<400> SEQUENCE: 192

His Gly Glu Ala Thr Phe Thr Ser Asp Leu Ser Lys Gln Met Glu Glu
  1               5                  10                  15

Glu Ala Val Arg Leu Phe Ile Glu Trp Leu Lys Asn Gly Gly Pro Ser
             20                  25                  30

Ser Gly

<210> SEQ ID NO 193
<211> LENGTH: 33
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (33)
<223> OTHER INFORMATION: Ser in position 33 is amidated

<400> SEQUENCE: 193

His Gly Glu Gly Thr Phe Thr Ser Ala Leu Ser Lys Gln Met Glu Glu
  1               5                  10                  15

Glu Ala Val Arg Leu Phe Ile Glu Trp Leu Lys Asn Gly Gly Pro Ser
             20                  25                  30

Ser

<210> SEQ ID NO 194
<211> LENGTH: 32
<212> TYPE: PRT
<213> ORGANISM: Artificial Sequence
<220> FEATURE:
<223> OTHER INFORMATION: Description of Artificial Sequence: Synthetic
```

-continued

```
      Amino Acid Sequence
<220> FEATURE:
<221> NAME/KEY: AMIDATION
<222> LOCATION: (32)
<223> OTHER INFORMATION: Ser in position 32 is amidated

<400> SEQUENCE: 194

Ala Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

<210> SEQ ID NO 195
<211> LENGTH: 32
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (32)
<223> OTHER INFORMATION: Ser in position 32 is amidated

<400> SEQUENCE: 195

His Gly Ala Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly Pro Ser
            20                  25                  30

<210> SEQ ID NO 196
<211> LENGTH: 31
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (31)
<223> OTHER INFORMATION: Pro in position 31 is amidated

<400> SEQUENCE: 196

His Gly Glu Ala Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro
            20                  25                  30

<210> SEQ ID NO 197
<211> LENGTH: 30
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (30)
<223> OTHER INFORMATION: Gly in position 30 is amidated

<400> SEQUENCE: 197

His Gly Glu Gly Thr Phe Thr Ser Ala Leu Ser Lys Gln Leu Glu Glu
 1               5                  10                  15

Glu Ala Val Arg Leu Phe Ile Glu Phe Leu Lys Asn Gly Gly
            20                  25                  30

<210> SEQ ID NO 198
```

```
<211> LENGTH: 29
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (29)
<223> OTHER INFORMATION: Gly in position 29 is amidated

<400> SEQUENCE: 198

Ala Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn Gly
             20                  25

<210> SEQ ID NO 199
<211> LENGTH: 38
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (31)
<223> OTHER INFORMATION: Xaa in position 31 stands for tPro
<220> FEATURE:
<221> NAME/KEY: VARIANT
<222> LOCATION: (36)..(38)
<223> OTHER INFORMATION: Xaa in positions 36-38 stands for tPro
<220> FEATURE:
<221> NAME/KEY: AMIDATION
<222> LOCATION: (38)
<223> OTHER INFORMATION: tPro in position 38 is amidated

<400> SEQUENCE: 199

His Gly Ala Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Xaa Ser
             20                  25                  30

Ser Gly Ala Xaa Xaa Xaa
             35

<210> SEQ ID NO 200
<211> LENGTH: 38
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (36)..(38)
<223> OTHER INFORMATION: Xaa in positions 36-38 stands for tPro
<220> FEATURE:
<221> NAME/KEY: AMIDATION
<222> LOCATION: (38)
<223> OTHER INFORMATION: tPro in position 38 is amidated

<400> SEQUENCE: 200

His Gly Glu Ala Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
             20                  25                  30

Ser Gly Ala Xaa Xaa Xaa
             35
```

```
<210> SEQ ID NO 201
<211> LENGTH: 37
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (31)
<223> OTHER INFORMATION: Xaa in position 31 stands for Nme
<220> FEATURE:
<221> NAME/KEY: VARIANT
<222> LOCATION: (36)..(37)
<223> OTHER INFORMATION: Xaa in positions 36-37 stands for Nme
<220> FEATURE:
<221> NAME/KEY: AMIDATION
<222> LOCATION: (37)
<223> OTHER INFORMATION: Nme in position 37 is amidated

<400> SEQUENCE: 201

His Gly Glu Gly Thr Phe Thr Ser Ala Leu Ser Lys Gln Met Glu Glu
 1               5                  10                  15

Glu Ala Val Arg Leu Phe Ile Glu Trp Leu Lys Asn Gly Gly Xaa Ser
            20                  25                  30

Ser Gly Ala Xaa Xaa
        35

<210> SEQ ID NO 202
<211> LENGTH: 36
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (31)
<223> OTHER INFORMATION: Xaa in position 31 stands for hPro
<220> FEATURE:
<221> NAME/KEY: VARIANT
<222> LOCATION: (36)
<223> OTHER INFORMATION: Xaa in position 36 stands for hPro
<220> FEATURE:
<221> NAME/KEY: AMIDATION
<222> LOCATION: (36)
<223> OTHER INFORMATION: hPro in position 36 is amidated

<400> SEQUENCE: 202

Ala Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Xaa Ser
            20                  25                  30

Ser Gly Ala Xaa
        35

<210> SEQ ID NO 203
<211> LENGTH: 35
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (35)
<223> OTHER INFORMATION: Ala in position 35 is amidated

<400> SEQUENCE: 203
```

```
His Gly Ala Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala
        35
```

<210> SEQ ID NO 204
<211> LENGTH: 30
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (30)
<223> OTHER INFORMATION: Gly in position 30 is amidated

<400> SEQUENCE: 204

```
His Gly Asp Ala Thr Phe Thr Ser Asp Leu Ser Lys Gln Met Glu Glu
 1               5                  10                  15

Glu Ala Val Arg Leu Phe Ile Glu Trp Leu Lys Asn Gly Gly
            20                  25                  30
```

<210> SEQ ID NO 205
<211> LENGTH: 39
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (39)
<223> OTHER INFORMATION: Ser in position 39 is amidated

<400> SEQUENCE: 205

```
Ala Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35
```

<210> SEQ ID NO 206
<211> LENGTH: 39
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (39)
<223> OTHER INFORMATION: Ser in position 39 is amidated

<400> SEQUENCE: 206

```
Ala Gly Ala Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly Pro Ser
            20                  25                  30

Ser Gly Ala Pro Pro Pro Ser
        35
```

```
<210> SEQ ID NO 207
<211> LENGTH: 27
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (1)
<223> OTHER INFORMATION: Xaa in position 1 stands for
      4-Imidazolylpropionyl-Gly
<220> FEATURE:
<221> NAME/KEY: VARIANT
<222> LOCATION: (26)
<223> OTHER INFORMATION: Xaa in position 26 stands for Lys-NH(epsilon)
      octanoyl
<220> FEATURE:
<221> NAME/KEY: AMIDATION
<222> LOCATION: (27)
<223> OTHER INFORMATION: Asn in position 27 is amidated

<400> SEQUENCE: 207

Xaa Glu Gly Thr Phe Thr Ser Ala Leu Ser Lys Gln Met Glu Glu Glu
 1               5                  10                  15

Ala Val Arg Leu Phe Ile Glu Trp Leu Xaa Asn
             20                  25

<210> SEQ ID NO 208
<211> LENGTH: 27
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (1)
<223> OTHER INFORMATION: Xaa in position 1 stands for
      4-Imidazolylpropionyl-Gly
<220> FEATURE:
<221> NAME/KEY: VARIANT
<222> LOCATION: (26)
<223> OTHER INFORMATION: Xaa in position 26 stands for Lys-NH(epsilon)
      octanoyl
<220> FEATURE:
<221> NAME/KEY: AMIDATION
<222> LOCATION: (27)
<223> OTHER INFORMATION: Asn in position 27 is amidated

<400> SEQUENCE: 208

Xaa Glu Gly Thr Phe Thr Ser Ala Leu Ser Lys Gln Leu Glu Glu Glu
 1               5                  10                  15

Ala Val Arg Leu Phe Ile Glu Phe Leu Xaa Asn
             20                  25

<210> SEQ ID NO 209
<211> LENGTH: 29
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (1)
<223> OTHER INFORMATION: Xaa in position 1 stands for
      4-Imidazolylpropionyl-Gly
<220> FEATURE:
<221> NAME/KEY: VARIANT
<222> LOCATION: (26)
<223> OTHER INFORMATION: Xaa in position 26 stands for Lys-NH(epsilon)
      octanoyl
```

```
<220> FEATURE:
<221> NAME/KEY: AMIDATION
<222> LOCATION: (29)
<223> OTHER INFORMATION: Gly in position 29 is amidated

<400> SEQUENCE: 209

Xaa Glu Gly Thr Phe Thr Ser Ala Leu Ser Lys Gln Met Glu Glu Glu
 1               5                  10                  15

Ala Val Arg Leu Phe Ile Glu Trp Leu Xaa Asn Gly Gly
            20                  25

<210> SEQ ID NO 210
<211> LENGTH: 29
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (1)
<223> OTHER INFORMATION: Xaa in position 1 stands for
      4-Imidazolylpropionyl-Gly
<220> FEATURE:
<221> NAME/KEY: VARIANT
<222> LOCATION: (26)
<223> OTHER INFORMATION: Xaa in position 26 stands for Lys-NH(epsilon)
      octanoyl
<220> FEATURE:
<221> NAME/KEY: AMIDATION
<222> LOCATION: (29)
<223> OTHER INFORMATION: Gly in position 29 is amidated

<400> SEQUENCE: 210

Xaa Glu Gly Thr Phe Thr Ser Ala Leu Ser Lys Gln Leu Glu Glu Glu
 1               5                  10                  15

Ala Val Arg Leu Phe Ile Glu Phe Leu Xaa Asn Gly Gly
            20                  25

<210> SEQ ID NO 211
<211> LENGTH: 27
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (1)
<223> OTHER INFORMATION: Xaa in position 1 stands for
      4-Imidazolylpropionyl-Gly
<220> FEATURE:
<221> NAME/KEY: VARIANT
<222> LOCATION: (27)
<223> OTHER INFORMATION: Xaa in position 27 stands for Lys-NH(epsilon)
      octanoyl
<220> FEATURE:
<221> NAME/KEY: AMIDATION
<222> LOCATION: (27)
<223> OTHER INFORMATION: Lys-NH(epsilon) octanoyl in position 27 is
      amidated

<400> SEQUENCE: 211

Xaa Glu Gly Thr Phe Thr Ser Ala Leu Ser Lys Gln Met Glu Glu Glu
 1               5                  10                  15

Ala Val Arg Leu Phe Ile Glu Trp Leu Asn Xaa
            20                  25

<210> SEQ ID NO 212
<211> LENGTH: 27
```

```
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (1)
<223> OTHER INFORMATION: Xaa in position 1 stands for
      4-Imidazolylpropionyl-Gly
<220> FEATURE:
<221> NAME/KEY: VARIANT
<222> LOCATION: (27)
<223> OTHER INFORMATION: Xaa in position 27 stands for Lys-NH(epsilon)
      octanoyl
<220> FEATURE:
<221> NAME/KEY: AMIDATION
<222> LOCATION: (27)
<223> OTHER INFORMATION: Lys-NH(epsilon) octanoyl

<400> SEQUENCE: 212

Xaa Glu Gly Thr Phe Thr Ser Ala Leu Ser Lys Gln Leu Glu Glu
 1               5                  10                  15

Ala Val Arg Leu Phe Ile Glu Phe Leu Asn Xaa
            20                  25

<210> SEQ ID NO 213
<211> LENGTH: 29
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (1)
<223> OTHER INFORMATION: Xaa in positon 1 stands for
      4-Imidazolylpropionyl-Gly
<220> FEATURE:
<221> NAME/KEY: VARIANT
<222> LOCATION: (27)
<223> OTHER INFORMATION: Xaa in position 27 stands for Lys-NH(epsilon)
      octanoyl
<220> FEATURE:
<221> NAME/KEY: AMIDATION
<222> LOCATION: (29)
<223> OTHER INFORMATION: Gly in position 29 is amidated

<400> SEQUENCE: 213

Xaa Glu Gly Thr Phe Thr Ser Ala Leu Ser Lys Gln Met Glu Glu
 1               5                  10                  15

Ala Val Arg Leu Phe Ile Glu Trp Leu Asn Xaa Gly Gly
            20                  25

<210> SEQ ID NO 214
<211> LENGTH: 29
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (1)
<223> OTHER INFORMATION: Xaa in position 1 stands for
      4-Imidazolylpropionyl-Gly
<220> FEATURE:
<221> NAME/KEY: VARIANT
<222> LOCATION: (27)
<223> OTHER INFORMATION: Xaa in position 27 stands for Lys-NH(epsilon)
      octanoyl
<220> FEATURE:
<221> NAME/KEY: AMIDATION
```

```
<222> LOCATION: (29)
<223> OTHER INFORMATION: Gly in position 29 is amidated

<400> SEQUENCE: 214

Xaa Glu Gly Thr Phe Thr Ser Ala Leu Ser Lys Gln Leu Glu Glu
 1               5                  10                  15

Ala Val Arg Leu Phe Ile Glu Phe Leu Asn Xaa Gly Gly
            20                  25

<210> SEQ ID NO 215
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (27)
<223> OTHER INFORMATION: Xaa in position 27 stands for Lys-NH(epsilon)
      octanoyl
<220> FEATURE:
<221> NAME/KEY: AMIDATION
<222> LOCATION: (28)
<223> OTHER INFORMATION: Asn in position 28 is amidated

<400> SEQUENCE: 215

Ala Gly Glu Gly Thr Phe Thr Ser Asp Leu Ser Lys Gln Met Glu Glu
 1               5                  10                  15

Glu Ala Val Arg Leu Phe Ile Glu Trp Leu Xaa Asn
            20                  25

<210> SEQ ID NO 216
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (27)
<223> OTHER INFORMATION: Xaa in position 27 stands for Lys-NH(epsilon)
      octanoyl
<220> FEATURE:
<221> NAME/KEY: AMIDATION
<222> LOCATION: (28)
<223> OTHER INFORMATION: Asn in position 28 is amidated

<400> SEQUENCE: 216

Ala Gly Glu Gly Thr Phe Thr Ser Asp Leu Ser Lys Gln Leu Glu Glu
 1               5                  10                  15

Glu Ala Val Arg Leu Phe Ile Glu Phe Leu Xaa Asn
            20                  25

<210> SEQ ID NO 217
<211> LENGTH: 30
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (27)
<223> OTHER INFORMATION: Xaa in position 27 stands for Lys-NH(epsilon)
      octanoyl
<220> FEATURE:
<221> NAME/KEY: AMIDATION
<222> LOCATION: (30)
```

```
<223> OTHER INFORMATION: Gly in position 30 is amidated

<400> SEQUENCE: 217

Ala Gly Glu Gly Thr Phe Thr Ser Asp Leu Ser Lys Gln Met Glu Glu
 1               5                  10                  15

Glu Ala Val Arg Leu Phe Ile Glu Trp Leu Xaa Asn Gly Gly
            20                  25                  30

<210> SEQ ID NO 218
<211> LENGTH: 30
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (27)
<223> OTHER INFORMATION: Xaa in position 27 stands for Lys-NH(epsilon)
      octanoyl
<220> FEATURE:
<221> NAME/KEY: AMIDATION
<222> LOCATION: (30)
<223> OTHER INFORMATION: Gly in position 30 is amidated

<400> SEQUENCE: 218

Ala Gly Glu Gly Thr Phe Thr Ser Asp Leu Ser Lys Gln Leu Glu Glu
 1               5                  10                  15

Glu Ala Val Arg Leu Phe Ile Glu Phe Leu Xaa Asn Gly Gly
            20                  25                  30

<210> SEQ ID NO 219
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (28)
<223> OTHER INFORMATION: Xaa in position 28 stands for Lys-NH(epsilon)
      octanoyl
<220> FEATURE:
<221> NAME/KEY: AMIDATION
<222> LOCATION: (28)
<223> OTHER INFORMATION: Lys-NH(epsilon) octanoyl in position 28 is
      amidated

<400> SEQUENCE: 219

Ala Gly Glu Gly Thr Phe Thr Ser Asp Leu Ser Lys Gln Met Glu Glu
 1               5                  10                  15

Glu Ala Val Arg Leu Phe Ile Glu Trp Leu Asn Xaa
            20                  25

<210> SEQ ID NO 220
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (28)
<223> OTHER INFORMATION: Xaa in position 28 stands for Lys-NH(epsilon)
      octanoyl
<220> FEATURE:
<221> NAME/KEY: AMIDATION
<222> LOCATION: (28)
```

```
<223> OTHER INFORMATION: Lys-NH(epsilon) octanoyl in position 28 is
      amidated

<400> SEQUENCE: 220

Ala Gly Glu Gly Thr Phe Thr Ser Asp Leu Ser Lys Gln Leu Glu Glu
 1               5                  10                  15

Glu Ala Val Arg Leu Phe Ile Glu Phe Leu Asn Xaa
            20                  25

<210> SEQ ID NO 221
<211> LENGTH: 30
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (28)
<223> OTHER INFORMATION: Xaa in position 28 stands for Lys-NH(epsilon)
      octanoyl
<220> FEATURE:
<221> NAME/KEY: AMIDATION
<222> LOCATION: (30)
<223> OTHER INFORMATION: Gly in position 30 is amidated

<400> SEQUENCE: 221

Ala Gly Glu Gly Thr Phe Thr Ser Asp Leu Ser Lys Gln Met Glu Glu
 1               5                  10                  15

Glu Ala Val Arg Leu Phe Ile Glu Trp Leu Asn Xaa Gly Gly
            20                  25                  30

<210> SEQ ID NO 222
<211> LENGTH: 30
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (28)
<223> OTHER INFORMATION: Xaa in position 28 stands for Lys-NH(epsilon)
      octanoyl
<220> FEATURE:
<221> NAME/KEY: AMIDATION
<222> LOCATION: (30)
<223> OTHER INFORMATION: Gly in position 30 is amidated

<400> SEQUENCE: 222

Ala Gly Glu Gly Thr Phe Thr Ser Asp Leu Ser Lys Gln Leu Glu Glu
 1               5                  10                  15

Glu Ala Val Arg Leu Phe Ile Glu Phe Leu Asn Xaa Gly Gly
            20                  25                  30

<210> SEQ ID NO 223
<211> LENGTH: 39
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: MOD_RES
<222> LOCATION: (12)
<223> OTHER INFORMATION: Lys-PEG
<220> FEATURE:
<221> NAME/KEY: AMIDATION
<222> LOCATION: (39)
<223> OTHER INFORMATION: Ser in position 39 is amidated
```

<400> SEQUENCE: 223

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 224
<211> LENGTH: 39
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: MOD_RES
<222> LOCATION: (27)
<223> OTHER INFORMATION: Lys-PEG
<220> FEATURE:
<221> NAME/KEY: AMIDATION
<222> LOCATION: (39)
<223> OTHER INFORMATION: Ser in position 39 is amidated

<400> SEQUENCE: 224

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 225
<211> LENGTH: 39
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: MOD_RES
<222> LOCATION: (2)
<223> OTHER INFORMATION: Lys-PEG
<220> FEATURE:
<221> NAME/KEY: AMIDATION
<222> LOCATION: (39)
<223> OTHER INFORMATION: Ser in position 39 is amidated

<400> SEQUENCE: 225

His Lys Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 226
<211> LENGTH: 39
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: MOD_RES
<222> LOCATION: (5)

```
<223> OTHER INFORMATION: Lys-PEG
<220> FEATURE:
<221> NAME/KEY: AMIDATION
<222> LOCATION: (39)
<223> OTHER INFORMATION: Ser in position 39 is amidated

<400> SEQUENCE: 226

His Gly Glu Gly Lys Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 227
<211> LENGTH: 39
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: MOD_RES
<222> LOCATION: (8)
<223> OTHER INFORMATION: Lys-PEG
<220> FEATURE:
<221> NAME/KEY: AMIDATION
<222> LOCATION: (39)
<223> OTHER INFORMATION: Ser in position 39 is amidated

<400> SEQUENCE: 227

His Gly Glu Gly Thr Phe Thr Lys Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 228
<211> LENGTH: 39
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: MOD_RES
<222> LOCATION: (10)
<223> OTHER INFORMATION: Lys-PEG
<220> FEATURE:
<221> NAME/KEY: AMIDATION
<222> LOCATION: (39)
<223> OTHER INFORMATION: Ser in position 39 is amidated

<400> SEQUENCE: 228

His Gly Glu Gly Thr Phe Thr Ser Asp Lys Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 229
<211> LENGTH: 39
<212> TYPE: PRT
<213> ORGANISM: Artificial Sequence
<220> FEATURE:
```

```
<223> OTHER INFORMATION: Description of Artificial Sequence: Synthetic
      Amino Acid Sequence
<220> FEATURE:
<221> NAME/KEY: MOD_RES
<222> LOCATION: (11)
<223> OTHER INFORMATION: Lys-PEG
<220> FEATURE:
<221> NAME/KEY: AMIDATION
<222> LOCATION: (39)
<223> OTHER INFORMATION: Ser in position 39 is amidated

<400> SEQUENCE: 229

His Gly Glu Gly Thr Phe Thr Ser Asp Leu Lys Lys Gln Met Glu Glu
  1               5                  10                  15

Glu Ala Val Arg Leu Phe Ile Glu Trp Leu Lys Asn Gly Gly Pro Ser
             20                  25                  30

Ser Gly Ala Pro Pro Pro Ser
         35

<210> SEQ ID NO 230
<211> LENGTH: 39
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: MOD_RES
<222> LOCATION: (13)
<223> OTHER INFORMATION: Lys-PEG
<220> FEATURE:
<221> NAME/KEY: AMIDATION
<222> LOCATION: (39)
<223> OTHER INFORMATION: Ser in position 39 is amidated

<400> SEQUENCE: 230

His Gly Glu Gly Thr Phe Thr Ser Asp Leu Ser Lys Lys Met Glu Glu
  1               5                  10                  15

Glu Ala Val Arg Leu Phe Ile Glu Trp Leu Lys Asn Gly Gly Pro Ser
             20                  25                  30

Ser Gly Ala Pro Pro Pro Ser
         35

<210> SEQ ID NO 231
<211> LENGTH: 39
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: MOD_RES
<222> LOCATION: (16)
<223> OTHER INFORMATION: Lys-PEG
<220> FEATURE:
<221> NAME/KEY: AMIDATION
<222> LOCATION: (39)
<223> OTHER INFORMATION: Ser in position 39 is amidated

<400> SEQUENCE: 231

His Gly Glu Gly Thr Phe Thr Ser Asp Leu Ser Lys Gln Met Glu Lys
  1               5                  10                  15

Glu Ala Val Arg Leu Phe Ile Glu Trp Leu Lys Asn Gly Gly Pro Ser
             20                  25                  30

Ser Gly Ala Pro Pro Pro Ser
         35
```

```
<210> SEQ ID NO 232
<211> LENGTH: 39
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: MOD_RES
<222> LOCATION: (17)
<223> OTHER INFORMATION: Lys-PEG
<220> FEATURE:
<221> NAME/KEY: AMIDATION
<222> LOCATION: (39)
<223> OTHER INFORMATION: Ser in position 39 is amidated

<400> SEQUENCE: 232

His Gly Glu Gly Thr Phe Thr Ser Asp Leu Ser Lys Gln Met Glu Glu
 1               5                  10                  15

Lys Ala Val Arg Leu Phe Ile Glu Trp Leu Lys Asn Gly Gly Pro Ser
             20                  25                  30

Ser Gly Ala Pro Pro Pro Ser
         35

<210> SEQ ID NO 233
<211> LENGTH: 39
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: MOD_RES
<222> LOCATION: (19)
<223> OTHER INFORMATION: Lys-PEG
<220> FEATURE:
<221> NAME/KEY: AMIDATION
<222> LOCATION: (39)
<223> OTHER INFORMATION: Ser in position 39 is amidated

<400> SEQUENCE: 233

His Gly Glu Gly Thr Phe Thr Ser Asp Leu Ser Lys Gln Met Glu Glu
 1               5                  10                  15

Glu Ala Lys Arg Leu Phe Ile Glu Trp Leu Lys Asn Gly Gly Pro Ser
             20                  25                  30

Ser Gly Ala Pro Pro Pro Ser
         35

<210> SEQ ID NO 234
<211> LENGTH: 39
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: MOD_RES
<222> LOCATION: (21)
<223> OTHER INFORMATION: Lys-PEG
<220> FEATURE:
<221> NAME/KEY: AMIDATION
<222> LOCATION: (39)
<223> OTHER INFORMATION: Ser in position 39 is amidated

<400> SEQUENCE: 234

His Gly Glu Gly Thr Phe Thr Ser Asp Leu Ser Lys Gln Met Glu Glu
 1               5                  10                  15

Glu Ala Val Arg Lys Phe Ile Glu Trp Leu Lys Asn Gly Gly Pro Ser
             20                  25                  30
```

Ser Gly Ala Pro Pro Pro Ser
        35

<210> SEQ ID NO 235
<211> LENGTH: 39
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: MOD_RES
<222> LOCATION: (24)
<223> OTHER INFORMATION: Lys-PEG
<220> FEATURE:
<221> NAME/KEY: AMIDATION
<222> LOCATION: (39)
<223> OTHER INFORMATION: Ser in position 39 is amidated

<400> SEQUENCE: 235

His Gly Glu Gly Thr Phe Thr Ser Asp Leu Ser Lys Gln Met Glu Glu
 1               5                  10                  15

Glu Ala Val Arg Leu Phe Ile Lys Trp Leu Lys Asn Gly Gly Pro Ser
            20                  25                  30

Ser Gly Ala Pro Pro Pro Ser
        35

<210> SEQ ID NO 236
<211> LENGTH: 39
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: MOD_RES
<222> LOCATION: (25)
<223> OTHER INFORMATION: Lys-PEG
<220> FEATURE:
<221> NAME/KEY: AMIDATION
<222> LOCATION: (39)
<223> OTHER INFORMATION: Ser in position 39 is amidated

<400> SEQUENCE: 236

His Gly Glu Gly Thr Phe Thr Ser Asp Leu Ser Lys Gln Met Glu Glu
 1               5                  10                  15

Glu Ala Val Arg Leu Phe Ile Glu Lys Leu Lys Asn Gly Gly Pro Ser
            20                  25                  30

Ser Gly Ala Pro Pro Pro Ser
        35

<210> SEQ ID NO 237
<211> LENGTH: 39
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: MOD_RES
<222> LOCATION: (28)
<223> OTHER INFORMATION: Lys-PEG
<220> FEATURE:
<221> NAME/KEY: AMIDATION
<222> LOCATION: (39)
<223> OTHER INFORMATION: Ser in position 39 is amidated

<400> SEQUENCE: 237

-continued

```
His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Lys Gly Gly Pro Ser
            20                  25                  30

Ser Gly Ala Pro Pro Ser
        35
```

<210> SEQ ID NO 238
<211> LENGTH: 39
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: MOD_RES
<222> LOCATION: (29)
<223> OTHER INFORMATION: Lys-PEG
<220> FEATURE:
<221> NAME/KEY: AMIDATION
<222> LOCATION: (39)
<223> OTHER INFORMATION: Ser in position 39 is amidated

<400> SEQUENCE: 238

```
His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Lys Gly Pro Ser
            20                  25                  30

Ser Gly Ala Pro Pro Ser
        35
```

<210> SEQ ID NO 239
<211> LENGTH: 39
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: MOD_RES
<222> LOCATION: (30)
<223> OTHER INFORMATION: Lys-PEG
<220> FEATURE:
<221> NAME/KEY: AMIDATION
<222> LOCATION: (39)
<223> OTHER INFORMATION: Ser in position 39 is amidated

<400> SEQUENCE: 239

```
His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Lys Pro Ser
            20                  25                  30

Ser Gly Ala Pro Pro Ser
        35
```